United States Patent
Ueda et al.

(10) Patent No.: US 7,714,157 B2
(45) Date of Patent: May 11, 2010

(54) PROCESS FOR PREPARING A BIARYL COMPOUND

(75) Inventors: Hiroshi Ueda, Ibaraki (JP); Isao Kurimoto, Suita (JP)

(73) Assignee: Sumitomo Chemical Company, Limited, Osaka (JP)

( * ) Notice: Subject to any disclaimer, the term of this patent is extended or adjusted under 35 U.S.C. 154(b) by 127 days.

(21) Appl. No.: 11/878,820

(22) Filed: Jul. 27, 2007

(65) Prior Publication Data

US 2007/0270603 A1 Nov. 22, 2007

Related U.S. Application Data

(62) Division of application No. 10/774,498, filed as application No. PCT/JP03/02460 on Mar. 4, 2003, now Pat. No. 7,271,280.

(30) Foreign Application Priority Data

Mar. 5, 2002 (JP) .............................. 2002-058624
Mar. 18, 2002 (JP) .............................. 2002-073833

(51) Int. Cl.
*C07C 309/72* (2006.01)
(52) U.S. Cl. .......................................... 558/56; 558/58
(58) Field of Classification Search ........................ None
See application file for complete search history.

(56) References Cited

U.S. PATENT DOCUMENTS

| | | | |
|---|---|---|---|
| 5,693,650 A | 12/1997 | Muller et al. | |
| 6,194,599 B1 | 2/2001 | Miller et al. | |
| 6,403,584 B1 | 6/2002 | de Laszlo et al. | |
| 2002/0010199 A1 | 1/2002 | Hagmann et al. | |

FOREIGN PATENT DOCUMENTS

| | | | |
|---|---|---|---|
| DE | 44 43 892 A1 | 6/1996 | |
| DE | 444892 A | 6/1996 | |
| EP | 339549 A2 | 11/1989 | |
| EP | 1043309 A1 | 10/2000 | |
| JP | 53-103440 | 9/1978 | |
| JP | 2000-212185 A | 8/2000 | |
| JP | 2001-89368 A | 4/2001 | |
| NL | 300552 | * 11/1963 | |
| WO | WO 95/30673 A | 11/1995 | |
| WO | WO 97/24342 | 7/1997 | |
| WO | WO 99/26921 A1 | 6/1999 | |
| WO | WO 99/36393 A1 | 6/1999 | |
| WO | WO 99/55324 A | 11/1999 | |
| WO | WO 99/55726 A1 | 11/1999 | |
| WO | WO 00/43372 | 7/2000 | |
| WO | WO 00/71572 | 11/2000 | |
| WO | WO 00/76970 | 12/2000 | |
| WO | WO 00/76971 | 12/2000 | |
| WO | WO 00/77027 | 12/2000 | |
| WO | WO 01/12183 | 2/2001 | |
| WO | WO 01/14328 | 3/2001 | |
| WO | WO 01/36376 | 5/2001 | |
| WO | WO 01/44226 | 6/2001 | |
| WO | WO 01/47867 | 7/2001 | |
| WO | WO 01/47874 A | 7/2001 | |
| WO | WO 01/77113 A | 10/2001 | |
| WO | WO 01/96303 A | 12/2001 | |
| WO | WO 01/96304 A | 12/2001 | |
| WO | 02/06222 A1 | 1/2002 | |
| WO | WO 02/39997 A2 | 5/2002 | |

OTHER PUBLICATIONS

Collection of Czechoslovak Chemical Communications (1960); 26, 2496-2510.

(Continued)

*Primary Examiner*—Kamal A Saeed
(74) *Attorney, Agent, or Firm*—Sughrue Mion, PLLC

(57) ABSTRACT

A process for preparing an optically active biaryl compound the formula (4):

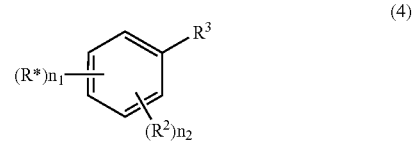

which comprises reacting an aromatic sulfonic acid ester compound of the formula (1):

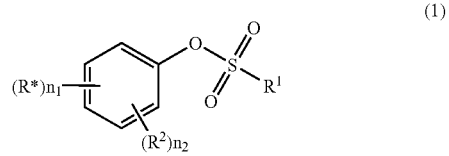

with an organic boron compound of the formula (2):

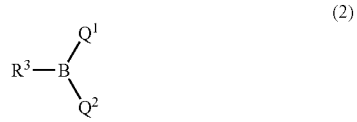

at 70° C. or below in the presence of a nickel catalyst and a base. The biaryl compounds produced using this process possess a high optical purity and are useful as intermediates for medicaments, agrochemicals, etc.

6 Claims, No Drawings

OTHER PUBLICATIONS

Justus Liebigs Annalen der Chemie (1962), 651, 172-184.
Bioorganicheskaya Khimiya (1987); 13(3), 320-337.
P. Karrer et al.; "Überführung optisch aktiver α-Aminocarbonsäuren in optisch active Amine mit gleichem Kohlenstoffskelett"; Helvetic Chimica Acta, vol. 34, 1951, pp. 2202-2210; XP002412039.
Journal of Organic Chemistry (1995), 60(4), pp. 1060-1065.
A. Sentissi et al., "Pentafluorobenzenesulfonyl Chloride: A New Electrophoric Derivatizing Reagent with Application to Tyrosyl Peptide Determination by Gas Chromatography with Electron Capture Detection", Analytical Chemistry (1984), 56 (13), pp. 25-12-2517.
J.W. Janetka et al., "Total Synthesis of the Cyclic Biphenyl Ether Peptides K-13 and OF4949-III via $S_NAr$ Macrocyclization of Peptidyl Ruthenium π-Arene Complexes", J. Am. Chem. Soc., (1997), 119, pp. 6488-6495.
S. Boisnard et al., A high throughput synthesis of aryl triflate and aryl nonaflate promoted by a polymer supported base (PTBD), Tetrahedron Letters (1999), 40(42), pp. 7469-7472.
Bulletin of the Journal of Chemical Society of Japan, (2000), 73(1), pp. 231-235.
Australian Journal of Chemistry, (1966), 19(12), pp. 2361-2372.
Journal of Medicinal Chemistry, (1977), 20(12), pp. 1584-1588.
Tetrahedron (2002), 58(15), pp. 3101-3110.
Tetrahedron Letters (2002), 43(12), pp. 2211-2214.
Journal of Organic Chemistry (1996), 61(9), pp. 2922-2923.
Journal of Medicinal Chemistry (1991), 34(3), pp. 1125-1136.
Journal of Organic Chemistry (2001), 66(1), pp. 348-350.

* cited by examiner

US 7,714,157 B2

PROCESS FOR PREPARING A BIARYL COMPOUND

This is a divisional of application Ser. No. 10/774,498 filed Feb. 10, 2004 now U.S. Pat. No. 7,271,280, which is a National Stage Application of PCT Application No. PCT/JP03/02460 filed Mar. 4, 2003. The entire disclosures of the prior application, application Ser. No. 10/774,498 is hereby incorporated by reference.

TECHNICAL FIELD

The present invention relates to a process for preparing an optically active biaryl compound, which is useful as intermediates for medicaments, agrochemicals, etc.

BACKGROUND ART

As conventional processes for preparing an optically active biaryl compound, for example, cross-coupling of N-(t-butyloxycarbonyl)-O-(trifluoromethanesulfonyl)-tyrosine methyl ester which is a derivative of a natural amino acid tyrosine, with phenylboronic acid in the presence of a palladium catalyst (WO 2001-36376); cross-coupling of N-FMOC-4-(trimethylstannyl)phenylalanine t-butyl ester with a halobenzene in the presence of a palladium catalyst (WO 2001-12183); cross-coupling of N-(t-butyloxycarbonyl)-4-iodophenylalanine methyl ester with phenylboronic acid in the presence of a palladium catalyst (WO 2000-43372), etc. are known.

However, the above-mentioned cross-coupling methods have problems in the process. For example, a problem is that these methods use expensive palladium catalysts and therefore the catalysts are required to be collected after the reaction. Furthermore, syntheses of reaction substrates are complicated because the leaving groups of the reaction substrates, aromatic compounds are a trifluoromethanesulfonyloxy group, which is synthesized using expensive and high caustic trifluoromethanesulfonic anhydride; a halogen, which has problematic position selectivity for introduction onto an aromatic ring; a trimethylstannyl group, which is derived from the halogen, and the like. Therefore, these methods are not necessarily satisfactory in industry.

DISCLOSURE OF THE INVENTION

The present inventors intensively studied and found that an optically active biaryl compound can be prepared with fine optical purity, by cross-coupling an aromatic sulfonic acid ester compound of a phenol compound having an optically active substituent on the aromatic ring without the above-mentioned trifluoromethanesulfonyloxy group, halogen or trimethylstannyl group, with an organic boron compound using a nickel catalyst that is more inexpensive than palladium catalysts at 70° C. or below, which resulted in the completion of the present invention.

That is, the present invention provides a process for preparing an optically active biaryl compound of the formula (4):

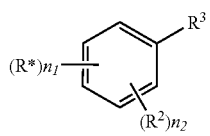

wherein

R* is the same or different and represents a substituent having at least one asymmetric carbon, $R^2$ is the same or different and represents a fluorine atom, a cyano group, a nitro group, a substituted or unsubstituted linear or branched alkyl group, a substituted or unsubstituted cycloalkyl group, a substituted or unsubstituted aryl or heterocyclic group, a hydroxyl group, an alkoxyl group, an aryloxy group, an alkylthio group, an arylthio group, a protected amino group, a substituted or unsubstituted carbamoyl group, a substituted or unsubstituted sulfonamide group, a formyl group, an alkylcarbonyl group, an arylcarbonyl group, a carboxyl group, an alkoxycarbonyl group, or an aryloxycarbonyl group, or the substituents on the adjacent carbon atoms of the benzene ring may be bound each other and taken together with the benzene ring to form a fused polycyclic aromatic ring, $R^3$ is a substituted or unsubstituted aryl or heteroaryl group, $n_1$ is an integer of 1 to 5, $n_2$ is an integer of 0 to 4, and

* is as defined hereinafter, which comprises reacting an aromatic sulfonic acid ester compound of the formula (1):

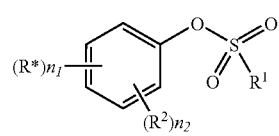

wherein $R^1$ is a substituted or unsubstituted alkyl or aryl group, and $R^2$, $R^*$, $n_1$, $n_2$ and * are as defined hereinabove, provided that $R^1$ is not a trifluoromethyl group, a nonafluorobutyl group or a pentafluorophenyl group, with an organic boron compound of the formula (2):

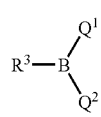

wherein $R^3$ is as defined above, and $Q^1$ and $Q^2$ are the same or different and each is a hydroxyl group, or an alkoxy group having 1 to 4 carbon atoms; or $Q^1$ and $Q^2$ are taken together to form an alkylenedioxy group having 1 to 4 carbon atoms or 1,2-phenylenedioxy group, which is optionally substituted with an alkyl group having 1 to 4 carbon atoms, or a boroxine ring compound of the formula (3):

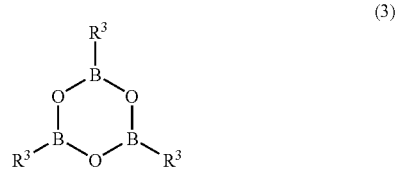

(3)

wherein $R^3$ is as defined hereinabove, or a mixture of compounds of the formula (2) and the formula (3), at 70° C. or below in the presence of a nickel catalyst and a base.

MODE FOR CARRYING OUT THE INVENTION

Hereinafter the present invention is explained in detail.

For the optically active aromatic sulfonic acid ester compound (1), the substituted or unsubstituted alkyl group represented by $R^1$ includes a methyl group and an ethyl group. The unsubstituted aryl group represented by $R^1$ includes a tolyl group such as a p-tolyl group and a phenyl group. The substituted aryl group represented by $R^1$ includes a nitrophenyl group such as a p-nitrophenyl group. Preferred are a methyl group, a p-tolyl group and a phenyl group. As $R^1$, in addition to a trifluoromethyl group, a nonafluorobutyl group of N-acetyl-O-(nonafluorobutanesulfonyl)tyrosine methyl ester and a pentafluorophenyl group of N-acetyl-O-[(pentafluorophenyl)sulfonyl]tyrosine ethyl ester, which are respectively disclosed in Tetrahedron Lett. 1999, 40, 7469-7472 and Anal. Chem., 1984, 56, 2512-2517 are known, but for the present invention, it is not necessary that $R^1$ is such an expensive fluorine-substituted group.

For the optically active aromatic sulfonic acid ester compound (1) and the optically active biaryl compound (4), the substituents represented by $R^2$ are explained hereinafter.

The unsubstituted alkyl group includes linear or branched alkyl groups such as a methyl group, an ethyl group, a propyl group, a butyl group and an isopropyl group, and cycloalkyl groups such as a cyclopropyl group, a cyclobutyl group, a cyclopentyl group and a cyclohexyl group. The substituted alkyl group includes haloalkyl groups such as a trifluoromethyl group.

The substituted or unsubstituted heterocyclic group includes a pyridyl group, a quinazolinyl group, a pyrimidyl group, a furyl group, a thienyl group, a pyrrolyl group and a imidazolyl group. The substituted or unsubstituted aryl group includes a phenyl group and a naphthyl group.

The alkoxy group includes a methoxy group and an ethoxy group.

The aryloxy group includes a phenoxy group.

The alkylthio group includes a methylthio group and an ethylthio group.

The arylthio group includes a phenylthio group.

The protected amino group includes a t-butyloxycarbonylamino group projected with a t-butyloxycarbonyl group, etc.

The substituted or unsubstituted sulfonamide group includes a benzenesulfonamide group and a methanesulfonamide group.

The substituted or unsubstituted alkoxycarbonyl group includes a methoxycarbonyl group, an ethoxycarbonyl group and a benzyloxycarbonyl group.

The substituted or unsubstituted carbamoyl group includes a carbamoyl group and a N-phenylcarbamoyl group.

The substituted or unsubstituted aryloxycarbonyl group includes a phenoxycarbonyl group and a p-methoxyphenoxycarbonyl group.

In the optically active aromatic sulfonic acid ester compound (1) and optically active biaryl compound (4), the optically active substituent R* is a substituent having at least one asymmetric carbon, and the specific example includes a group of the formula (5):

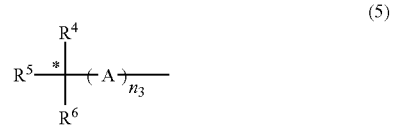

(5)

wherein $R^4$, $R^5$ and $R^6$ are different and each is a hydrogen atom, a fluorine atom, a substituted or unsubstituted linear or branched alkyl group, a substituted or unsubstituted cycloalkyl group, a hydroxyl group, a substituted or unsubstituted alkoxyl group, a substituted or unsubstituted aryloxy group, a cyano group, a protected amino group, a formyl group, a carboxyl group, a substituted or unsubstituted alkoxycarbonyl group, a substituted or unsubstituted aryloxycarbonyl group, a substituted or unsubstituted carbamoyl group, a substituted or unsubstituted heterocyclic group, or a substituted or unsubstituted aryl group, A is a substituted or unsubstituted alkylene group, a substituted or unsubstituted nitrogen atom, oxygen atom or sulfur atom, $n_3$ is an integer of 0 or 1, and the carbon atom marked with * is an asymmetric carbon atom.

Hereinafter $R^4$, $R^5$ and $R^6$ of the formula (5) are explained in detail. The substituted or unsubstituted linear or branched alkyl group and substituted or unsubstituted cycloalkyl group include linear or branched alkyl groups such as a methyl group, an ethyl group, a propyl group, a butyl group and an isopropyl group, and cycloalkyl groups such as a cyclopropyl group, a cyclobutyl group, a cyclopentyl group and a cyclohexyl group, and further include halogen-substituted alkyl groups such as a trifluoromethyl group.

The substituted or unsubstituted alkoxy group includes a methoxy group and an ethoxy group.

The substituted or unsubstituted aryloxy group includes a phenoxy group.

The protected amino group includes a t-butyloxycarbonylamino group, and an amino group protected by a protecting group for an amino group as described below.

The substituted or unsubstituted alkoxycarbonyl group includes a methoxycarbonyl group, an ethoxycarbonyl group and a benzyloxycarbonyl group.

The substituted or unsubstituted aryloxycarbonyl group includes a phenoxycarbonyl group and a p-methoxyphenoxycarbonyl group.

The substituted or unsubstituted carbamoyl group includes a carbamoyl group and an N-phenylcarbamoyl group.

The substituted or unsubstituted heterocyclic group includes a pyridyl group, a quinazolinyl group, a pyrimidyl group, a furyl group, a thienyl group, a pyrrolyl group and an imidazolyl group.

The substituted or unsubstituted aryl group includes a phenyl group, a tolyl group and a naphthyl group.

The substituted or unsubstituted alkylene group represented by A includes alkylene groups having 1 to 4 carbon atoms, more specifically —CH$_2$—, —CH$_2$CH$_2$—, —C(CH$_3$)$_2$—, etc.

The substituted or unsubstituted nitrogen atom represented by A includes —NH—, —N(CH$_3$)—, etc.

The optically active substituent of the formula (5) includes a substituent of the formula (5'):

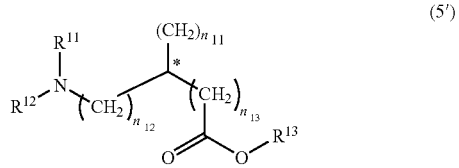

(5')

wherein

R$^{11}$ is a protecting group for an amino group,

R$^{12}$ is a protecting group for an amino group or a hydrogen atom,

R$^{13}$ is a substituted or unsubstituted alkyl group, or either R$^{11}$ or R$^{12}$ and R$^{13}$ are taken together to represent a protecting group for amino acid, n$_{11}$, n$_{12}$ and n$_{13}$ are each independently an integer of 0 or 1, and the carbon atom marked with * is an asymmetric carbon atom.

More specifically, a compound of the formula (1a)

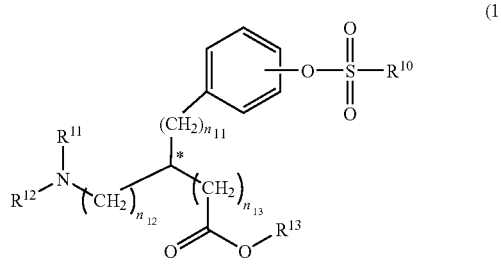

(1a)

wherein R$^{11}$, R$^{12}$, R$^{13}$ and n$_{11}$, n$_{12}$, n$_{13}$ and * are as defined hereinabove, and R$^{10}$ is as defined for R$^1$, which corresponds to a compound of the formula (1) wherein n$_1$=1 and n$_2$=0, is exemplified.

For the amino acid compound of the formula (1a), R$^{11}$ and R$^{12}$, the protecting groups for an amino group, include carbamate type amino-protecting groups such as a substituted or unsubstituted alkyloxycarbonyl group (wherein the substituent includes an alkylsilyl group, a substituted or unsubstituted aryl group, a halogen atom, a substituted or unsubstituted heterocyclic group, a bridged cyclic hydrocarbon group, an acyl group, an alkylthio group, a dicyclohexylcarboxyamide group, a substituted or unsubstituted benzenesulfonyl group, an alkylsulfonyl group, a substituted or unsubstituted phosphonio group, a cyano group, etc.), a substituted or unsubstituted alkenyloxycarbonyl group (wherein the substituent includes an aryl group, a nitro group, etc.), a substituted or unsubstituted aryloxycarbonyl group, a substituted or unsubstituted heterocyclic oxycarbonyl group and a substituted or unsubstituted alkyl dithiocarbonyl group, amide type amino-protecting groups, and N-alkyl type amino-protecting groups.

The substituted or unsubstituted alkyloxycarbonyl group specifically includes a methyloxycarbonyl group, an ethyloxycarbonyl group, an isobutyloxycarbonyl group, a t-butyloxycarbonyl group, a t-amyloxycarbonyl group, a 2,2,2-trichloroethyloxycarbonyl group, a 2-trimethylsilylethyloxycarbonyl group, a phenylethyloxycarbonyl group, a 1-(1-adamantyl)-1-methylethyloxycarbonyl group, a 1,1-dimethyl-2-haloethyloxycarbonyl group, a 1,1-dimethyl-2,2-dibromoethyloxycarbonyl group, a 1,1-dimethyl-2,2,2-trichloroethyloxycarbonyl group, a 1-methyl-1-(4-biphenylyl)ethyloxycarbonyl group, a 1-(3,5-di-t-butylphenyl)-1-methylethyloxycarbonyl group, a 2-(2'-pyridyl)ethyloxycarbonyl group, a 2-(4'-pyridyl)ethyloxycarbonyl group, a 2-(N,N-dicyclohexylcarboxyamide)ethyloxycarbonyl group, a 1-adamantyloxycarbonyl group, a benzyloxycarbonyl group, a p-methoxybenzyloxycarbonyl group, a p-nitrobenzyloxycarbonyl group, a p-bromobenzyloxycarbonyl group, a p-chlorobenzyloxycarbonyl group, a 2,4-dichlorobenzyloxycarbonyl group, a 4-methylsulfinylbenzyloxycarbonyl group, a 9-anthrylmethyloxycarbonyl group, a diphenylmethyloxycarbonyl group, a 9-fluorenylmethyloxycarbonyl group, a 9-(2,7-dibromo)fluorenylmethyloxycarbonyl group, a 2,7-di-t-butyl-[9-(10,10-dioxo-thioxanthyl)]methyloxycarbonyl group, a 4-methoxyphenacyloxycarbonyl group, a 2-methylthioethyloxycarbonyl group, a 2-methylsulfonylethyloxycarbonyl group, a 2-(p-toluenesulfonyl)ethyloxycarbonyl group, a [2-(1,3-dithianyl)]methyloxycarbonyl group, a 4-methylthiophenyloxycarbonyl group, a 2,4-dimethylthiophenyloxycarbonyl group, a 2-phosphonioethyloxycarbonyl group, a 2-triphenylphosphonioisopropyloxycarbonyl group, a 1,1-dimethyl-2-cyanoethyloxycarbonyl group, a m-chloro-p-acyloxybenzyloxycarbonyl group, a p-(dihydroxyboryl)benzyloxycarbonyl group, a 5-benzoisoxazolylmethyloxycarbonyl group, a 2-(trifluoromethyl)-6-chromonylmethyloxycarbonyl group, a 3,5-dimethoxybenzyloxycarbonyl group, a o-nitrobenzyloxycarbonyl group, a 3,4-dimethoxy-6-nitrobenzyloxycarbonyl group, and a phenyl(o-nitrophenyl)methyloxycarbonyl group.

The substituted or unsubstituted alkenyloxycarbonyl group includes a vinyloxycarbonyl group, an allyloxycarbonyl group, a 1-isopropylallyloxycarbonyl group, a cinnamyloxycarbonyl group and a 4-nitrocinnamyloxycarbonyl group.

The substituted or unsubstituted heterocyclic oxycarbonyl group includes an 8-quinolyloxycarbonyl group and an N-piperidinyloxycarbonyl group.

The substituted or unsubstituted aryloxycarbonyl group includes a phenyloxycarbonyl group and an m-nitrophenyloxycarbonyl group.

The amide type amino-protecting group includes a formyl group, an acetyl group, a chloroacetyl group, a trichloroacetyl group, a trifluoroacetyl group, a phenylacetyl group and a benzoyl group.

The N-alkyl type amino-protecting group includes a benzyl group, an N-di(4-methoxyphenyl)methyl group, an N-5-dibenzosuberyl group, an N-triphenylmethyl group, a (4-methoxyphenyl)diphenylmethyl group, an N-9-phenylfluorenyl group, an allyl group, an N-[2-(trimethylsilyl)ethoxy]methyl group and an N-3-acetoxypropyl group.

The substituted or unsubstituted alkyl group represented by R$^{13}$ includes a methyl group, an ethyl group, an n-propyl group, an isopropyl group, an n-butyl group, an isobutyl group, an s-butyl group, a t-butyl group, a cyclohexyl group, a 9-fluorenylmethyl group, a methoxymethyl group, a benzyloxymethyl group, a pivaloyloxymethyl group, a phenylacetoxymethyl group and an N-phthalimidomethyl group, preferably a C1 to C4 alkyl group, and further includes aralkyl groups such as a benzyl group, an α-phenethyl group, a triphenylmethyl group, a diphenylmethyl group, an o-nitrobenzyl group, a p-nitrobenzyl group, a p-methoxybenzyl group and a 2,6-dimethoxybenzyl group, preferably a benzyl group.

The protection of the amino acid formed by either $R^{11}$ or $R^{12}$ taken together with $R^{13}$ includes formation of a cyclic structure such as 4-substituted-5-oxo-1,3-oxazolidine, 4-substituted-2-methyl-5(4H)-oxazolone, 4-substituted-2,5-oxazolidinedione or 5-substituted-2,4-imidazolidinedione by reaction of an amino group and carboxyl group of the amino acid compound of the formula (1a) with a protecting agent.

$R^{10}$ is a substituted or unsubstituted alkyl or aryl group other than a fluorine-substituted alkyl or aryl group. The unsubstituted alkyl group includes a methyl group, an ethyl group, an n-propyl group, an isopropyl group, an n-butyl group, an isobutyl group, a s-butyl group and a t-butyl group, and preferably includes a methyl group. The substituted or unsubstituted aryl group includes a phenyl group, a p-methylphenyl group, a p-ethylphenyl group, a 3-nitrophenyl group, a 1-naphthyl group and a 2-naphthyl group, and preferably includes a phenyl group, a p-nitrophenyl group and p-methylphenyl group.

The compound of the formula (1a) wherein $R^{11}$ is a carbamate type amino-protecting group, an amide type amino-protecting group or an N-alkyl amino-protecting group and $R^{12}$ is a hydrogen atom is preferred. The compound of the formula (1a) wherein $R^{11}$ is an acetyl group, a trifluoroacetyl group, a benzyl group, a t-butyloxycarbonyl group, a 9-fluorenylmethoxycarbonyl group or a benzyloxycarbonyl group and $R^{12}$ is a hydrogen atom is more preferred.

The compound of the formula (1) can be prepared by, for example, reacting a phenol compound of the formula (6):

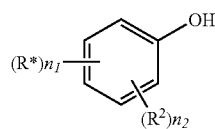

(6)

wherein $R^*$, $R^2$, $n_1$ and $n_2$ are as defined hereinabove, with a sulfonic acid halide or the corresponding sulfonic acid anhydride, which is a reactive derivative of $R^1SO_3H$, in the presence of a base (for example, a method described in the Chemical Society of Japan, ed., "Shinjikken Kagaku Koza 14, Synthesis and Reaction of Organic Compounds (III)", Maruzen Co., Ltd., 1978.) More specifically, it can be produced by the sulfonation step (C) as described below using the phenol compound of the formula (6) as a starting material. Although a method of preparing the compound of the formula (6) is not specifically limited, many of the compounds are available as a commercial product. Alternatively, the compound can be prepared by optically activating the corresponding racemate available as a commercial product by optical resolution, etc.

Furthermore, the compound of the formula (1a) can be prepared, for example, by subjecting the optically active compound of the formula (6a):

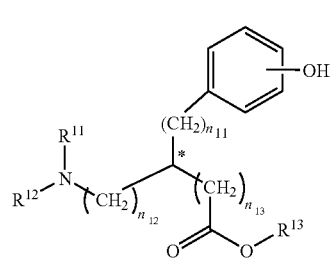

(6a)

wherein $R^{11}$, $R^{12}$, $R^{13}$, $n_{11}$, $n_{12}$, $n_{13}$ and * are as defined hereinabove, to a reaction similar to the reaction described above for the compound of the formula (6).

The compound of the formula (6a) can be prepared by carrying out by the carboxyl group-protecting step (A), the amino group-protecting step (B) and the sulfonic acid esterification step (C) as described below, using an aromatic amino acid having a hydroxyl group on the aromatic ring of the formula (12):

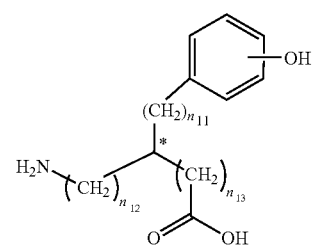

(12)

wherein $n_{11}$, $n_{12}$, $n_{13}$ and * are as defined hereinabove, as a starting material. Many of the compounds of the formula (12) are available as a commercial product. Alternatively, the compound can be prepared by optically activating the corresponding racemate available as a commercial product by optical resolution, etc. Moreover, the compound can be also prepared from the corresponding aldehyde compound and halide according to a method described in, for example, Chemical Society of Japan, ed., "Jikken Kagaku Koza 22, Organic Synthesis IV, Acid, Amino Acid and Peptide", 4$^{th}$ edition, Maruzen Co., Ltd., 1992, pp. 193-214.

The steps (A), (B) and (C) can be carried out in any order. Alternatively, two or three of these steps can be carried out simultaneously depending on reagents to be used.

(A) Carboxyl Group-Protecting Step

An amino acid ester compound is obtained by, for example, reacting an aromatic amino acid having a hydroxyl group on the aromatic ring or a salt thereof with an alcohol compound of the formula (13): $R^{13}OH$ wherein $R^{13}$ is a substituted or unsubstituted alkyl group, in the presence of an esterifying agent. The amino group portion of the amino acid ester compound may be free or may be in the form of an acid salt such as hydrochloride, methanesulfonate, p-toluenesulfonate or benzenesulfonate. The alcohol compound (13) used herein includes methanol, ethanol, n-propanol, isopropanol, n-butanol, sec-butanol, t-butanol and benzylalcohol. The amount used of the alcohol compound is usually from about 1 mol to 40 mol, preferably from about 10 mol to 30 mol relative to 1 mol of the substrate. The esterifying agent includes chlorinating agents such as thionyl chloride and phosphorus oxychloride. The amount used of the esterifying agent is usually from about 1 mol to 5 mol, preferably from about 1 mol to 2 mol relative to 1 mol of the substrate. In addition, an organic solvent may be added to the reaction, if necessary. The reaction temperature is usually in the range from −20° C. to the reflux temperature of the reaction mixture, preferably in the range of about 0° C. to 60° C. After the reaction is completed, the reaction mass is optionally concentrated, and an organic solvent such as toluene is optionally added to the reaction mass to give an acid salt of the desired amino acid ester compound.

(B) Amino Group-Protecting Step

An amino acid ester compound in which a protecting group for an amino group represented by $R^{11}$ or $R^{12}$ has been introduced is obtained by, for example, reacting the amino acid ester compound or an acid salt thereof with a protecting agent for an amino group in the presence of a base. The protecting agent used herein may be any protecting agent that provides the above-mentioned groups exemplified as a protecting group for an amino group. For introduction of the representative protecting group $R^{11}$ or $R^{12}$, specific examples of a protecting agent include acyl halides such as acetyl chloride and di-t-butylcarbonate.

The amount used of the protecting agent is usually from 1 mol to 10 mol, preferably from about 1 mol to 3 mol relative to 1 mol of the substrate.

The base used in the above reaction includes organic bases such as triethylamine and pyridine, and inorganic bases such as sodium hydroxide. The amount used of the base is usually from about 0.1 mol to 2 mol relative to 1 mol of the substrate.

In the above reaction, an organic solvent is usually used. Such a solvent includes hydrocarbon solvents such as n-hexane, cyclohexane, n-pentane, toluene and xylene, ether solvents such as diethylether, tetrahydrofuran and dioxane, ester solvents such as ethyl acetate and butyl acetate, halogen solvents such as chloroform, dichloromethane, monochlorobenzene and o-dichlorobenzene, and aprotic polar solvents such as N,N-dimethylformamide, dimethylsulfoxide and N,N-dimethylacetamide.

The reaction temperature is usually in the range from the freezing point of the reaction system to the boiling point of a solvent used, preferably in the range of −20° C. to 40° C.

After the reaction, the desired amino group-protected amino acid ester compound can be obtained by a conventional post-treatment.

Alternatively, a carboxyl group and an amino group of an aromatic amino acid having a hydroxyl group on the aromatic ring can be protected simultaneously. For example, the carboxyl group and amino group of an aromatic α-amino acid having a hydroxyl group on the aromatic ring can be protected simultaneously by a reaction with formaldehyde, acetic anhydride and thionyl chloride to give a 4-substituted-5-oxo-1,3-oxazolidine compound. A reagent for simultaneously protecting a carboxyl group and an amino group includes phosgene and urea. The amount used of the reagent is usually from about 1 mol to 10 mol, preferably about 1 mol to 3 mol relative to 1 mol of the substrate.

In the above reaction, an organic solvent is usually used. Such a solvent includes hydrocarbon solvents such as n-hexane, cyclohexane, n-pentane, toluene and xylene, ether solvents such as diethylether, tetrahydrofuran and dioxane, ester solvents such as ethyl acetate and butyl acetate, halogen solvents such as chloroform, dichloromethane, monochlorobenzene and o-dichlorobenzene, and aprotic polar solvents such as N,N-dimethylformamide, dimethylsulfoxide and N,N-dimethylacetamide.

The reaction temperature is usually in the range from the freezing point of the reaction system to the boiling point of a solvent used, preferably in the range of about −20° C. to 40° C.

After the reaction, the desired amino acid compound in which the carboxyl group and amino group have been simultaneously protected can be obtained by a conventional post-treatment.

(C) Sulfonic Esterification Step

The aromatic sulfonic acid ester compound of the formula (1) is obtained by, for example, reacting the phenol compound of the formula (6) or an amino group-protected amino acid ester compound with a sulfonic acid esterifying agent in the presence of a base. The sulfonic acid esterifying agent used herein includes sulfonic acid halide of the formula $R^1SO_2X$ or $R^{10}SO_2X$ wherein X is a halogen atom or $R^1SO_3$ or $R^{10}SO_3$, for example, sulfonic acid chloride such as p-toluenesulfonyl chloride and methanesulfonyl chloride, and sulfonic anhydrides such as p-toluenesulfonic anhydride and methanesulfonic anhydride. The amount used of the sulfonic acid esterifying agent is usually from about 1 mol to 3 mol relative to 1 mol of the substrate. The base used includes organic bases such as triethylamine and pyridine, and inorganic bases such as sodium hydroxide. The amount used of the base is usually from about 1 mol to 3 mol per 1 mol of the substrate.

In the above reaction, an organic solvent is usually used. Such a solvent includes hydrocarbon solvents such as n-hexane, cyclohexane, n-pentane, toluene and xylene, ether solvents such as diethyl ether, tetrahydrofuran and dioxane, ester solvents such as ethyl acetate and butyl acetate, halogen solvents such as chloroform, dichloromethane, monochlorobenzene and o-dichlorobenzene, and aprotic polar solvents such as N,N-dimethylformamide, dimethylsulfoxide and N,N-dimethylacetamide.

The reaction temperature is usually in the range from the freezing point of the reaction system to the boiling point of a solvent used, preferably in the range of about −20° C. to 40° C.

After the reaction, the desired aromatic sulfonic acid ester compound of the formula (1) can be obtained by conventional post-treatment.

Specific examples of the aromatic sulfonic acid ester compound of the formula (1) of the present invention include the optically active forms of the following compounds.

2-(4-(p-toluenesulfonyloxy)phenyl)butane, 2-(4-methanesulfonyloxyphenyl)butane, 2-(4-benzenesulfonyloxyphenyl)butane, 2-(4-(p-toluenesulfonyloxy)phenyl)pentane, 2-(4-methanesulfonyloxyphenyl)pentane, 2-(4-benzenesulfonyloxyphenyl)pentane, 2-methyl-3-(4-(p-toluenesulfonyloxy)phenyl)butane, 2-methyl-3-(4-methanesulfonyloxyphenyl)butane, 2-methyl-3-(4-benzenesulfonyloxyphenyl)butane, 2-(3-(p-toluenesulfonyloxy)phenyl)butane, 2-(3-methanesulfonyloxyphenyl)butane, 2-(3-benzenesulfonyloxyphenyl)butane, 2-(3-(p-toluenesulfonyloxy)phenyl)pentane, 2-(3-methanesulfonyloxyphenyl)pentane, 2-(3-benzenesulfonyloxyphenyl)pentane, 2-(2-(p-toluenesulfonyloxy)phenyl)butane, 2-(2-methanesulfonyloxyphenyl)butane, 2-(2-benzenesulfonyloxyphenyl)butane, 2-(2-(p-toluenesulfonyloxy)phenyl)pentane, 2-(2-methanesulfonyloxyphenyl)pentane, 2-(2-benzenesulfonyloxyphenyl)pentane, 2-methyl-3-(2-(p-toluenesulfonyloxy)phenyl)butane, 2-methyl-3-(2-methanesulfonyloxyphenyl)butane, 2-methyl-3-(2-benzenesulfonyloxyphenyl)butane,
1-phenyl-1-(4-(p-toluenesulfonyloxy)phenyl)ethane, 1-phenyl-1-(4-methanesulfonyloxyphenyl)ethane, 1-phenyl-1-(4-benzenesulfonyloxyphenyl)ethane,
1-phenyl-1-(4-(p-toluenesulfonyloxy)phenyl)propane, 1-phenyl-1-(4-methanesulfonyloxyphenyl)propane, 1-phenyl-1-(4-benzenesulfonyloxyphenyl)propane,
2-methyl-1-phenyl-1-(4-(p-toluenesulfonyloxy)phenyl)propane, 2-methyl-1-phenyl-1-(4-methanesulfonyloxyphenyl)propane, 2-methyl-1-phenyl-1-(4-benzenesulfonyloxyphenyl)propane,
2,2-dimethyl-1-phenyl-1-(4-(p-toluenesulfonyloxy)phenyl)propane, 2,2-dimethyl-1-phenyl-1-(4-methanesulfonyloxyphenyl)propane, 2,2-dimethyl-1-phenyl-1-(4-benzenesulfonyloxyphenyl)propane,
1-phenyl-1-(2-(p-toluenesulfonyloxy)phenyl)ethane, 1-phenyl-1-(2-methanesulfonyloxyphenyl)ethane, 1-phenyl-1-(2-benzenesulfonyloxyphenyl)ethane,
1-phenyl-1-(2-(p-toluenesulfonyloxy)phenyl)propane, 1-phenyl-1-(2-methanesulfonyloxyphenyl)propane, 1-phenyl-1-(2-benzenesulfonyloxyphenyl)propane,
2-methyl-1-phenyl-1-(2-(p-toluenesulfonyloxy)phenyl)propane, 2-methyl-1-phenyl-1-(2-methanesulfonyloxyphenyl)propane, 2-methyl-1-phenyl-1-(2-benzenesulfonyloxyphenyl)propane,
2,2-dimethyl-1-phenyl-1-(2-(p-toluenesulfonyloxy)phenyl)propane, 2,2-dimethyl-1-phenyl-1-(2-methanesulfonyloxyphenyl)propane, 2,2-dimethyl-1-phenyl-1-(2-benzenesulfonyloxyphenyl)propane,
2-methyl-2-(4-(p-toluenesulfonyloxy)phenyl)acetaldehyde, 2-methyl-2-(3-(p-toluenesulfonyloxy)phenyl)acetaldehyde, 2-methyl-2-(2-(p-toluenesulfonyloxy)phenyl)acetaldehyde, 2-methyl-2-(4-methanesulfonyloxyphenyl)acetaldehyde, 2-methyl-2-(3-methanesulfonyloxyphenyl)acetaldehyde, 2-methyl-2-(2-methanesulfonyloxyphenyl)acetaldehyde, 2-methyl-2-(4-benzenesulfonyloxyphenyl)acetaldehyde, 2-methyl-2-(3-benzenesulfonyloxyphenyl)acetaldehyde, 2-methyl-2-(2-benzenesulfonyloxyphenyl)acetaldehyde,
3-(4-(p-toluenesulfonyloxy)phenyl)-2-butanone, 3-(3-(p-toluenesulfonyloxy)phenyl)-2-butanone, 3-(4-methanesulfonyloxyphenyl)-2-butanone, 3-(3-methanesulfonyloxyphenyl)-2-butanone, 3-(4-benzenesulfonyloxyphenyl)-2-butanone, 3-(3-benzenesulfonyloxyphenyl)-2-butanone,
2-methyl-2-(4-(p-toluenesulfonyloxy)phenyl)acetonitrile, 2-methyl-2-(2-(p-toluenesulfonyloxy)phenyl)acetonitrile, 2-methyl-2-(4-methanesulfonyloxyphenyl)acetonitrile, 2-methyl-2-(2-methanesulfonyloxyphenyl)acetonitrile, 2-methyl-2-(4-benzenesulfonyloxyphenyl)acetonitrile, 2-methyl-2-(2-benzenesulfonyloxyphenyl)acetonitrile,
2-(4-(p-toluenesulfonyloxy)phenyl)propanoic acid methyl ester, 2-(3-(p-toluenesulfonyloxy)phenyl)propanoic acid methyl ester, 2-(2-(p-toluenesulfonyloxy)phenyl)propanoic acid methyl ester, 2-(4-methanesulfonyloxyphenyl)propanoic acid methyl ester, 2-(3-methanesulfonyloxyphenyl)propanoic acid methyl ester, 2-(2-methanesulfonyloxyphenyl)propanoic acid methyl ester, 2-(4-benzenesulfonyloxyphenyl)propanoic acid methyl ester, 2-(3-benzenesulfonyloxyphenyl)propanoic acid methyl ester, 2-(2-benzenesulfonyloxyphenyl)propanoic acid methyl ester,
2-(4-(p-toluenesulfonyloxy)phenyl)propanoic acid ethyl ester, 2-(3-(p-toluenesulfonyloxy)phenyl)propanoic acid ethyl ester, 2-(2-(p-toluenesulfonyloxy)phenyl)propanoic acid ethyl ester, 2-(4-methanesulfonyloxyphenyl)propanoic acid ethyl ester, 2-(3-methanesulfonyloxyphenyl)propanoic acid ethyl ester, 2-(2-methanesulfonyloxyphenyl)propanoic acid ethyl ester, 2-(4-benzenesulfonyloxyphenyl)propanoic acid ethyl ester, 2-(3-benzenesulfonyloxyphenyl)propanoic acid ethyl ester, 2-(2-benzenesulfonyloxyphenyl)propanoic acid ethyl ester,
2-(4-(p-toluenesulfonyloxy)phenyl)propanoic acid (t-butyl)ester, 2-(3-(p-toluenesulfonyloxy)phenyl)propanoic acid (t-butyl)ester, 2-(2-(p-toluenesulfonyloxy)phenyl)propanoic acid (t-butyl)ester, 2-(4-methanesulfonyloxyphenyl)propanoic acid (t-butyl)ester, 2-(3-methanesulfonyloxyphenyl)propanoic acid (t-butyl)ester,
2-(2-methanesulfonyloxyphenyl)propanoic acid (t-butyl)ester, 2-(4-benzenesulfonyloxyphenyl)propanoic acid (t-butyl)ester,
2-(3-benzenesulfonyloxyphenyl)propanoic acid (t-butyl)ester, 2-(2-benzenesulfonyloxyphenyl)propanoic acid (t-butyl)ester,
2-(4-(p-toluenesulfonyloxy)phenyl)propanoic acid benzyl ester, 2-(3-(p-toluenesulfonyloxy)phenyl)propanoic acid benzyl ester, 2-(2-(p-toluenesulfonyloxy)phenyl)propanoic acid benzyl ester, 2-(4-methanesulfonyloxyphenyl)propanoic acid benzyl ester, 2-(3-methanesulfonyloxyphenyl)propanoic acid benzyl ester, 2-(2-methanesulfonyloxyphenyl)propanoic acid benzyl ester, 2-(4-benzenesulfonyloxyphenyl)propanoic acid benzyl ester, 2-(3-benzenesulfonyloxyphenyl)propanoic acid benzyl ester, 2-(2-benzenesulfonyloxyphenyl)propanoic acid benzyl ester,
2-(4-(p-toluenesulfonyloxy)phenyl)butanoic acid methyl ester, 2-(2-(p-toluenesulfonyloxy)phenyl)butanoic acid methyl ester, 2-(4-methanesulfonyloxyphenyl)butanoic acid methyl ester, 2-(2-methanesulfonyloxyphenyl)butanoic acid methyl ester, 2-(4-benzenesulfonyloxyphenyl)butanoic acid methyl ester, 2-(2-benzenesulfonyloxyphenyl)butanoic acid methyl ester,
3-methyl-2-(4-(p-toluenesulfonyloxy)phenyl)butanoic acid methyl ester, 3-methyl-2-(3-(p-toluenesulfonyloxy)phenyl)butanoic acid methyl ester, 3-methyl-2-(4-methanesulfonyloxyphenyl)butanoic acid methyl ester, 3-methyl-2-(3-methanesulfonyloxyphenyl)butanoic acid methyl ester, 3-methyl-2-(4-benzenesulfonyloxyphenyl)butanoic acid methyl ester, 3-methyl-2-(3-benzenesulfonyloxyphenyl)butanoic acid methyl ester,
2-methyl-2-(4-(p-toluenesulfonyloxy)phenyl)acetamide, 2-methyl-2-(3-(p-toluenesulfonyloxy)phenyl)acetamide, 2-methyl-2-(4-methanesulfonyloxyphenyl)acetamide, 2-methyl-2-(3-methanesulfonyloxyphenyl)acetamide, 2-methyl-2-(4-benzenesulfonyloxyphenyl)acetamide,
2-methyl-2-(3-benzenesulfonyloxyphenyl)acetamide, 4-(p-toluenesulfonyloxy)-α-methylbenzylalcohol, 4-methanesulfonyloxy-α-methylbenzylalcohol, 4-benzenesulfonyloxy-α-methylbenzylalcohol,
4-(p-toluenesulfonyloxy)-α-methylbenzylalcohol methyl ether,
4-methanesulfonyloxy-α-methylbenzylalcohol methyl ether, 4-benzenesulfonyloxy-α-methylbenzylalcohol methyl ether, 4-(p-toluenesulfonyloxy)-α-methylbenzylalcohol benzyl ether,
4-methanesulfonyloxy-α-methylbenzylalcohol benzyl ether, 4-benzenesulfonyloxy-α-methylbenzylalcohol benzyl ether,
4-(p-toluenesulfonyloxy)-α-methylbenzylalcohol trimethylsilyl ether, 4-methanesulfonyloxy-α-methylbenzylalcohol trimethylsilyl ether, 4-benzenesulfonyloxy-α-methylbenzylalcohol trimethylsilyl ether, 4-(p-toluenesulfonyloxy)-α-methylbenzyl acetate, 4-methanesulfonyloxy-α-methylbenzyl acetate, 4-benzenesulfonyloxy-α-methylbenzyl acetate, 3-(p-toluenesulfonyloxy)-α-methylbenzylalcohol, 3-methanesulfonyloxy-α-methylbenzylalcohol, 3-benzenesulfonyloxy-α-methylbenzylalcohol, 3-(p-toluenesulfonyloxy)-α-methylbenzylalcohol methyl ether, 3-methanesulfonyloxy-α-methylbenzylalcohol methyl ether, 3-benzenesulfonyloxy-α-methylbenzylalcohol methyl ether, 3-(p-toluenesulfonyloxy)-α-methylbenzylalcohol benzyl ether, 3-methanesulfonyloxy-α-methylbenzylalcohol benzyl ether, 3-benzenesulfonyloxy-α-methylbenzylalcohol benzyl ether, 3-(p-toluenesulfonyloxy)-α-methylbenzylalcohol trimethylsilyl ether, 3-methanesulfonyloxy-α-methylbenzylalcohol trimethylsilyl ether, 3-benzenesulfonyloxy-α-methylbenzylalcohol trimethylsilyl ether, 3-(p-toluenesulfonyloxy)-α-methylbenzyl acetate, 3-methanesulfonyloxy-α-methylbenzyl acetate, 3-benzenesulfonyloxy-α-methylbenzyl acetate, 2-(p-toluenesulfonyloxy)-α-methylbenzylalcohol, 2-methanesulfonyloxy-α-methylbenzylalcohol, 2-benzenesulfonyloxy-α-methylbenzylalcohol, 2-(p-toluenesulfonyloxy)-α-methylbenzylalcohol methyl ether, 2-methanesulfonyloxy-α-methylbenzylalcohol methyl ether, 2-benzenesulfonyloxy-α-methylbenzylalcohol methyl ether, 2-(p-toluenesulfonyloxy)-α-methylbenzylalcohol benzyl ether, 2-methanesulfonyloxy-α-methylbenzylalcohol benzyl ether, 2-benzenesulfonyloxy-α-methylbenzylalcohol benzyl ether, 2-(p-toluenesulfonyloxy)-α-methylbenzylalcohol trimethylsilyl ether, 2-methanesulfonyloxy-α-methylbenzylalcohol trimethylsilyl ether, 2-benzenesulfonyloxy-α-methylbenzylalcohol trimethylsilyl ether, 2-(p-toluenesulfonyloxy)-α-methylbenzyl acetate, 2-methanesulfonyloxy-α-methylbenzyl acetate, 2-benzenesulfonyloxy-α-methylbenzyl acetate, 4-(p-toluenesulfonyloxy)-α-isopropylbenzylalcohol, 4-methanesulfonyloxy-α-isopropylbenzylalcohol, 4-benzenesulfonyloxy-α-isopropylbenzylalcohol, 4-(p-toluenesulfonyloxy)-α-isopropylbenzylalcohol methyl ether, 4-methanesulfonyloxy-α-isopropylbenzylalcohol methyl ether, 4-benzenesulfonyloxy-α-isopropylbenzylalcohol methyl ether, 4-(p-toluenesulfonyloxy)-α-isopropylbenzylalcohol benzyl ether, 4-methanesulfonyloxy-α-isopropylbenzylalcohol benzyl ether, 4-benzenesulfonyloxy-α-isopropylbenzylalcohol benzyl ether, 4-(p-toluenesulfonyloxy)-α-isopropylbenzylalcohol trimethylsilyl ether, 4-methanesulfonyloxy-α-isopropylbenzylalcohol trimethylsilyl ether, 4-benzenesulfonyloxy-α-isopropylbenzylalcohol trimethylsilyl ether, 4-(p-toluenesulfonyloxy)-α-isopropylbenzyl acetate, 4-methanesulfonyloxy-α-isopropylbenzyl acetate, 4-benzenesulfonyloxy-α-isopropylbenzyl acetate, 4-(p-toluenesulfonyloxy)-α-(t-butyl)benzylalcohol, 4-methanesulfonyloxy-α-(t-butyl)benzylalcohol, 4-benzenesulfonyloxy-α-(t-butyl)benzylalcohol, 4-(p-toluenesulfonyloxy)-α-(t-butyl)benzylalcohol methyl ether, 4-methanesulfonyloxy-α-(t-butyl)benzylalcohol methyl ether, 4-benzenesulfonyloxy-α-(t-butyl)benzylalcohol methyl ether, 4-(p-toluenesulfonyloxy)-α-(t-butyl)benzylalcohol benzyl ether, 4-methanesulfonyloxy-α-(t-butyl)benzylalcohol benzyl ether, 4-benzenesulfonyloxy-α-(t-butyl)benzylalcohol benzyl ether, 4-(p-toluenesulfonyloxy)-α-(t-butyl)benzylalcohol trimethylsilyl ether, 4-methanesulfonyloxy-α-(t-butyl)benzylalcohol trimethylsilyl ether, 4-benzenesulfonyloxy-α-(t-butyl)benzylalcohol trimethylsilyl ether, 4-(p-toluenesulfonyloxy)-α-(t-butyl)benzyl acetate, 4-methanesulfonyloxy-α-(t-butyl)benzyl acetate, 4-benzenesulfonyloxy-α-(t-butyl)benzyl acetate, 4-(p-toluenesulfonyloxy)-α-ethyl-α-methylbenzylalcohol, 4-methanesulfonyloxy-α-ethyl-α-methylbenzylalcohol, 4-benzenesulfonyloxy-α-ethyl-α-methylbenzylalcohol, 4-(p-toluenesulfonyloxy)-α-ethyl-α-methylbenzylalcohol methyl ether, 4-methanesulfonyloxy-α-ethyl-α-methylbenzylalcohol methyl ether, 4-benzenesulfonyloxy-α-ethyl-α-methylbenzylalcohol methyl ether, 4-(p-toluenesulfonyloxy)-α-ethyl-α-methylbenzylalcohol benzyl ether, 4-methanesulfonyloxy-α-ethyl-α-methylbenzylalcohol benzyl ether, 4-benzenesulfonyloxy-α-ethyl-α-methylbenzylalcohol benzyl ether, 4-(p-toluenesulfonyloxy)-α-ethyl-α-methylbenzylalcohol trimethylsilyl ether, 4-methanesulfonyloxy-α-ethyl-α-methylbenzylalcohol trimethylsilyl ether, 4-benzenesulfonyloxy-α-ethyl-α-methylbenzylalcohol trimethylsilyl ether, 4-(p-toluenesulfonyloxy)-α-ethyl-α-methylbenzyl acetate, 4-methanesulfonyloxy-α-ethyl-α-methylbenzyl acetate, 4-benzenesulfonyloxy-α-ethyl-α-methylbenzyl acetate, 4-(p-toluenesulfonyloxy)-α-cyanobenzylalcohol, 4-methanesulfonyloxy-α-cyanobenzylalcohol, 4-benzenesulfonyloxy-α-cyanobenzylalcohol, 4-(p-toluenesulfonyloxy)-α-cyanobenzylalcohol methyl ether, 4-methanesulfonyloxy-α-cyanobenzylalcohol methyl ether, 4-benzenesulfonyloxy-α-cyanobenzylalcohol methyl ether, 4-(p-toluenesulfonyloxy)-α-cyanobenzylalcohol benzyl ether, 4-methanesulfonyloxy-α-cyanobenzylalcohol benzyl ether, 4-benzenesulfonyloxy-α-cyanobenzylalcohol benzyl ether, 4-(p-toluenesulfonyloxy)-α-cyanobenzylalcohol trimethylsilyl ether, 4-methanesulfonyloxy-α-cyanobenzylalcohol trimethylsilyl ether, 4-benzenesulfonyloxy-α-cyanobenzylalcohol trimethylsilyl ether, 4-(p-toluenesulfonyloxy)-α-cyanobenzyl acetate, 4-methanesulfonyloxy-α-cyanobenzyl acetate, 4-benzenesulfonyloxy-α-cyanobenzyl acetate, 3-(p-toluenesulfonyloxy)-α-cyanobenzylalcohol, 3-methanesulfonyloxy-α-cyanobenzylalcohol, 3-benzenesulfonyloxy-α-cyanobenzylalcohol, 3-(p-toluenesulfonyloxy)-α-cyanobenzylalcohol methyl ether, 3-methanesulfonyloxy-α-cyanobenzylalcohol methyl ether, 3-benzenesulfonyloxy-α-cyanobenzylalcohol methyl ether, 3-(p-toluenesulfonyloxy)-α-cyanobenzylalcohol benzyl ether, 3-methanesulfonyloxy-α-cyanobenzylalcohol benzyl ether, 3-benzenesulfonyloxy-α-cyanobenzylalcohol benzyl ether, 3-(p-toluenesulfonyloxy)-α-cyanobenzylalcohol trimethylsilyl ether, 3-methanesulfonyloxy-α-cyanobenzylalcohol trimethylsilyl ether, 3-benzenesulfonyloxy-α-cyanobenzylalcohol trimethylsilyl ether, 3-(p-toluenesulfonyloxy)-α-cyanobenzyl acetate, 3-methanesulfonyloxy-α-cyanobenzyl acetate, 3-benzenesulfonyloxy-α-cyanobenzyl acetate, 2-(p-toluenesulfonyloxy)-α-cyanobenzylalcohol, 2-methanesulfonyloxy-α-cyanobenzylalcohol, 2-benzenesulfonyloxy-α-cyanobenzylalcohol, 2-(p-toluenesulfonyloxy)-α-cyanobenzylalcohol methyl ether, 2-methanesulfonyloxy-α-cyanobenzylalcohol methyl ether, 2-benzenesulfonyloxy-α-cyanobenzylalcohol methyl ether, 2-(p-toluenesulfonyloxy)-α-cyanobenzylalcohol benzyl ether, 2-methanesulfonyloxy-α-cyanobenzylalcohol benzyl ether, 2-benzenesulfonyloxy-α-cyanobenzylalcohol benzyl ether, 2-(p-toluenesulfonyloxy)-α-cyanobenzylalcohol trimethylsilyl ether, 2-methanesulfonyloxy-α-cyanobenzylalcohol trimethylsilyl ether, 2-benzenesulfonyloxy-α-cyanobenzylalcohol trimethylsilyl ether, 2-(p-toluenesulfonyloxy)-α-cyanobenzyl acetate, 2-methanesulfonyloxy-α-cyanobenzyl acetate, 2-benzenesulfonyloxy-α-cyanobenzyl acetate, 1-hydroxy-1-(4-(p-toluenesulfonyloxy)phenyl)propanone, 1-methoxy-1-(4-(p-toluenesulfonyloxy)phenyl)propanone, 1-benzyloxy-1-(4-(p-toluenesulfonyloxy)phenyl)propanone, 1-acetyloxy-1-(4-(p-toluenesulfonyloxy)phenyl)propanone, 1-trimethylsilyloxy-1-(4-(p-toluenesulfonyloxy)phenyl)propanone, 1-hydroxy-1-(3-(p-toluenesulfonyloxy)phenyl)propanone, 1-methoxy-1-(3-(p-toluenesulfonyloxy)phenyl)propanone, 1-benzyloxy-1-(3-(p-toluenesulfonyloxy)phenyl)propanone, 1-acetyloxy-1-(3-(p-toluenesulfonyloxy)phenyl)propanone, 1-trimethylsilyloxy-1-(3-(p-toluenesulfonyloxy)phenyl)propanone, 1-hydroxy-1-(2-(p-toluenesulfonyloxy)phenyl)propanone, 1-methoxy-1-(2-(p-toluenesulfonyloxy)phenyl)propanone, 1-benzyloxy-1-(2-(p-toluenesulfonyloxy)phenyl)propanone, 1-acetyloxy-1-(2-(p-toluenesulfonyloxy)phenyl)propanone, 1-trimethylsilyloxy-1-(2-(p-toluenesulfonyloxy)phenyl)propanone, 1-hydroxy-1-(4-methanesulfonyloxyphenyl)propanone, 1-methoxy-1-(4-methanesulfonyloxyphenyl)propanone, 1-benzyloxy-1-(4-methanesulfonyloxyphenyl)propanone, 1-acetyloxy-1-(4-methanesulfonyloxyphenyl)propanone, 1-trimethylsilyloxy-1-(4-methanesulfonyloxyphenyl)propanone, 1-hydroxy-1-(3-methanesulfonyloxyphenyl)propanone, 1-methoxy-1-(3-methanesulfonyloxyphenyl)propanone, 1-benzyloxy-1-(3-methanesulfonyloxyphenyl)propanone, 1-acetyloxy-1-(3-methanesulfonyloxyphenyl)propanone, 1-trimethylsilyloxy-1-(3-methanesulfonyloxyphenyl)propanone, 1-hydroxy-1-(2-methanesulfonyloxyphenyl)propanone, 1-methoxy-1-(2-methanesulfonyloxyphenyl)propanone, 1-benzyloxy-1-(2-methanesulfonyloxyphenyl)propanone, 1-acetyloxy-1-(2-methanesulfonyloxyphenyl)propanone, 1-trimethylsilyloxy-1-(2-methanesulfonyloxyphenyl)propanone, 1-hydroxy-1-(4-benzenesulfonyloxyphenyl)propanone, 1-methoxy-1-(4-benzenesulfonyloxyphenyl)propanone, 1-benzyloxy-1-(4-benzenesulfonyloxyphenyl)propanone, 1-acetyloxy-1-(4-benzenesulfonyloxyphenyl)propanone, 1-trimethylsilyloxy-1-(4-benzenesulfonyloxyphenyl)propanone, 1-hydroxy-1-(3-benzenesulfonyloxyphenyl)propanone, 1-methoxy-1-(3-benzenesulfonyloxyphenyl)propanone, 1-benzyloxy-1-(3-benzenesulfonyloxyphenyl)propanone, 1-acetyloxy-1-(3-benzenesulfonyloxyphenyl)propanone, 1-trimethylsilyloxy-1-(3-benzenesulfonyloxyphenyl)propanone, 1-hydroxy-1-(2-benzenesulfonyloxyphenyl)propanone, 1-methoxy-1-(2-benzenesulfonyloxyphenyl)propanone, 1-benzyloxy-1-(2-benzenesulfonyloxyphenyl)propanone, 1-acetyloxy-1-(2-benzenesulfonyloxyphenyl)propanone, 1-trimethylsilyloxy-1-(2-benzenesulfonyloxyphenyl)propanone 2-hydroxy-2-(4-(p-toluenesulfonyloxy)phenyl)acetic acid methyl ester, 2-methoxy-2-(4-(p-toluenesulfonyloxy)phenyl)acetic acid methyl ester, 2-benzyloxy-2-(4-(p-toluenesulfonyloxy)phenyl)acetic acid methyl ester, 2-acetyloxy-2-(4-(p-toluenesulfonyloxy)phenyl)acetic acid methyl ester, 2-trimethylsilyloxy-2-(4-(p-toluenesulfonyloxy)phenyl)acetic acid methyl ester, 2-hydroxy-2-(3-(p-toluenesulfonyloxy)phenyl)acetic acid methyl ester, 2-methoxy-2-(3-(p-toluenesulfonyloxy)phenyl)acetic acid methyl ester, 2-benzyloxy-2-(3-(p-toluenesulfonyloxy)phenyl)acetic acid methyl ester, 2-acetyloxy-2-(3-(p-toluenesulfonyloxy)phenyl)acetic acid methyl ester, 2-trimethylsilyloxy-2-(3-(p-toluenesulfonyloxy)phenyl)acetic acid methyl ester, 2-hydroxy-2-(2-(p-toluenesulfonyloxy)phenyl)acetic acid methyl ester, 2-methoxy-2-(2-(p-toluenesulfonyloxy)phenyl)acetic acid methyl ester, 2-benzyloxy-2-(2-(p-toluenesulfonyloxy)phenyl)acetic acid methyl ester, 2-acetyloxy-2-(2-(p-toluenesulfonyloxy)phenyl)acetic acid methyl ester, 2-trimethylsilyloxy-2-(2-(p-toluenesulfonyloxy)phenyl)acetic acid methyl ester, 2-hydroxy-2-(4-methanesulfonyloxyphenyl)acetic acid methyl ester, 2-methoxy-2-(4-methanesulfonyloxyphenyl)acetic acid methyl ester, 2-benzyloxy-2-(4-methanesulfonyloxyphenyl)acetic acid methyl ester, 2-acetyloxy-2-(4-methanesulfonyloxyphenyl)acetic acid methyl ester, 2-trimethylsilyloxy-2-(4-methanesulfonyloxyphenyl)acetic acid methyl ester, 2-hydroxy-2-(3-methanesulfonyloxyphenyl)acetic acid methyl ester, 2-methoxy-2-(3-methanesulfonyloxyphenyl)acetic acid methyl ester, 2-benzyloxy-2-(3-methanesulfonyloxyphenyl)acetic acid methyl ester, 2-acetyloxy-2-(3-methanesulfonyloxyphenyl)acetic acid methyl ester, 2-trimethylsilyloxy-2-(3-methanesulfonyloxyphenyl)acetic acid methyl ester, 2-hydroxy-2-(2-methanesulfonyloxyphenyl)acetic acid methyl ester, 2-methoxy-2-(2-methanesulfonyloxyphenyl)acetic acid methyl ester, 2-benzyloxy-2-(2-methanesulfonyloxyphenyl)acetic acid methyl ester, 2-acetyloxy-2-(2-methanesulfonyloxyphenyl)acetic acid methyl ester, 2-trimethylsilyloxy-2-(2-methanesulfonyloxyphenyl)acetic acid methyl ester, 2-hydroxy-2-(4-benzenesulfonyloxyphenyl)acetic acid methyl ester, 2-methoxy-2-(4-benzenesulfonyloxyphenyl)acetic acid methyl ester, 2-benzyloxy-2-(4-benzenesulfonyloxyphenyl)acetic acid methyl ester, 2-acetyloxy-2-(4-benzenesulfonyloxyphenyl)acetic acid methyl ester, 2-trimethylsilyloxy-2-(4-benzenesulfonyloxyphenyl)acetic acid methyl ester, 2-hydroxy-2-(3-benzenesulfonyloxyphenyl)acetic acid methyl ester, 2-methoxy-2-(3-benzenesulfonyloxyphenyl)acetic acid methyl ester, 2-benzyloxy-2-(3-benzenesulfonyloxyphenyl)acetic acid methyl ester, 2-acetyloxy-2-(3-benzenesulfonyloxyphenyl)acetic acid methyl ester, 2-trimethylsilyloxy-2-(3-benzenesulfonyloxyphenyl)acetic acid methyl ester, 2-hydroxy-2-(2-benzenesulfonyloxyphenyl)acetic acid methyl ester, 2-methoxy-2-(2-benzenesulfonyloxyphenyl)

acetic acid methyl ester, 2-benzyloxy-2-(2-benzenesulfonyloxyphenyl)acetic acid methyl ester, 2-acetyloxy-2-(2-benzenesulfonyloxyphenyl)acetic acid methyl ester, 2-trimethylsilyloxy-2-(2-benzenesulfonyloxyphenyl)acetic acid methyl ester, <formyl, alcohol>

2-hydroxy-2-(4-(p-toluenesulfonyloxy)phenyl)acetaldehyde,
2-methoxy-2-(4-(p-toluenesulfonyloxy)phenyl)acetaldehyde,
2-benzyloxy-2-(4-(p-toluenesulfonyloxy)phenyl)acetaldehyde,
2-acetyloxy-2-(4-(p-toluenesulfonyloxy)phenyl)acetaldehyde,
2-trimethylsilyloxy-2-(4-(p-toluenesulfonyloxy)phenyl)acetaldehyde, 2-hydroxy-2-(4-methanesulfonyloxyphenyl)acetaldehyde, 2-methoxy-2-(4-methanesulfonyloxyphenyl)acetaldehyde, 2-benzyloxy-2-(4-methanesulfonyloxyphenyl)acetaldehyde, 2-acetyloxy-2-(4-methanesulfonyloxyphenyl)acetaldehyde, 2-trimethylsilyloxy-2-(4-methanesulfonyloxyphenyl)acetaldehyde, 2-hydroxy-2-(4-benzenesulfonyloxyphenyl)acetaldehyde, 2-methoxy-2-(4-benzenesulfonyloxyphenyl)acetaldehyde, 2-benzyloxy-2-(4-benzenesulfonyloxyphenyl)acetaldehyde, 2-acetyloxy-2-(4-benzenesulfonyloxyphenyl)acetaldehyde, 2-trimethylsilyloxy-2-(4-benzenesulfonyloxyphenyl)acetaldehyde,
2-hydroxy-2-(4-(p-toluenesulfonyloxy)phenyl)acetamide,
2-methoxy-2-(4-(p-toluenesulfonyloxy)phenyl)acetamide, 2-benzyloxy-2-(4-(p-toluenesulfonyloxy)phenyl)acetamide, 2-acetyloxy-2-(4-(p-toluenesulfonyloxy)phenyl)acetamide, 2-trimethylsilyloxy-2-(4-(p-toluenesulfonyloxy)phenyl)acetamide, 2-hydroxy-2-(4-methanesulfonyloxyphenyl)acetamide, 2-methoxy-2-(4-methanesulfonyloxyphenyl)acetamide, 2-benzyloxy-2-(4-methanesulfonyloxyphenyl)acetamide, 2-acetyloxy-2-(4-methanesulfonyloxyphenyl)acetamide, 2-trimethylsilyloxy-2-(4-methanesulfonyloxyphenyl)acetamide, 2-hydroxy-2-(4-benzenesulfonyloxyphenyl)acetamide, 2-methoxy-2-(4-benzenesulfonyloxyphenyl)acetamide, 2-benzyloxy-2-(4-benzenesulfonyloxyphenyl)acetamide, 2-acetyloxy-2-(4-benzenesulfonyloxyphenyl)acetamide, 2-trimethylsilyloxy-2-(4-benzenesulfonyloxyphenyl)acetamide, N-(t-butyloxycarbonyl)-1-amino-1-(4-(p-toluenesulfonyloxy)phenyl)ethane, N-benzyloxycarbonyl-1-amino-1-(4-(p-toluenesulfonyloxy)phenyl)ethane, N-(9-fluorenylmethyloxycarbonyl)-1-amino-1-(4-(p-toluenesulfonyloxy)phenyl)ethane, N-acetyl-1-amino-1-(4-(p-toluenesulfonyloxy)phenyl)ethane, N-benzoyl-1-amino-1-(4-(p-toluenesulfonyloxy)phenyl)ethane, N-benzyl-1-amino-1-(4-(p-toluenesulfonyloxy)phenyl)ethane, N,N-dimethyl-1-amino-1-(4-(p-toluenesulfonyloxy)phenyl)ethane, N-(t-butyloxycarbonyl)-1-amino-1-(3-(p-toluenesulfonyloxy)phenyl)ethane, N-benzyloxycarbonyl-1-amino-1-(3-(p-toluenesulfonyloxy)phenyl)ethane, N-(9-fluorenylmethyloxycarbonyl)-1-amino-1-(3-(p-toluenesulfonyloxy)phenyl)ethane, N-acetyl-1-amino-1-(3-(p-toluenesulfonyloxy)phenyl)ethane, N-benzoyl-1-amino-1-(3-(p-toluenesulfonyloxy)phenyl)ethane, N-benzyl-1-amino-1-(3-(p-toluenesulfonyloxy)phenyl)ethane, N,N-dimethyl-1-amino-1-(3-(p-toluenesulfonyloxy)phenyl)ethane, N-(t-butyloxycarbonyl)-1-amino-1-(2-(p-toluenesulfonyloxy)phenyl)ethane, N-benzyloxycarbonyl-1-amino-1-(2-(p-toluenesulfonyloxy)phenyl)ethane, N-(9-fluorenylmethyloxycarbonyl)-1-amino-1-(2-(p-toluenesulfonyloxy)phenyl)ethane, N-acetyl-1-amino-1-(2-(p-toluenesulfonyloxy)phenyl)ethane, N-benzoyl-1-amino-1-(2-(p-toluenesulfonyloxy)phenyl)ethane, N-benzyl-1-amino-1-(2-(p-toluenesulfonyloxy)phenyl)ethane, N,N-dimethyl-1-amino-1-(2-(p-toluenesulfonyloxy)phenyl)ethane, N-(t-butyloxycarbonyl)-1-amino-1-(4-(p-toluenesulfonyloxy)phenyl)propane, N-benzyloxycarbonyl-1-amino-1-(4-(p-toluenesulfonyloxy)phenyl)propane, N-(9-fluorenylmethyloxycarbonyl)-1-amino-1-(4-(p-toluenesulfonyloxy)phenyl)propane, N-acetyl-1-amino-1-(4-(p-toluenesulfonyloxy)phenyl)propane, N-benzoyl-1-amino-1-(4-(p-toluenesulfonyloxy)phenyl)propane, N-benzyl-1-amino-1-(4-(p-toluenesulfonyloxy)phenyl)propane, N,N-dimethyl-1-amino-1-(4-(p-toluenesulfonyloxy)phenyl)propane, N-(t-butyloxycarbonyl)-1-amino-1-(2-(p-toluenesulfonyloxy)phenyl)propane, N-benzyloxycarbonyl-1-amino-1-(2-(p-toluenesulfonyloxy)phenyl)propane, N-(9-fluorenylmethyloxycarbonyl)-1-amino-1-(2-(p-toluenesulfonyloxy)phenyl)propane, N-acetyl-1-amino-1-(2-(p-toluenesulfonyloxy)phenyl)propane, N-benzoyl-1-amino-1-(2-(p-toluenesulfonyloxy)phenyl)propane, N-benzyl-1-amino-1-(2-(p-toluenesulfonyloxy)phenyl)propane, N,N-dimethyl-1-amino-1-(2-(p-toluenesulfonyloxy)phenyl)propane, N-(t-butyloxycarbonyl)-2-amino-1-(4-(p-toluenesulfonyloxy)phenyl)propane, N-benzyloxycarbonyl-2-amino-1-(4-(p-toluenesulfonyloxy)phenyl)propane, N-(9-fluorenylmethyloxycarbonyl)-2-amino-1-(4-(p-toluenesulfonyloxy)phenyl)propane, N-acetyl-2-amino-1-(4-(p-toluenesulfonyloxy)phenyl)propane, N-benzoyl-2-amino-1-(4-(p-toluenesulfonyloxy)phenyl)propane, N-benzyl-2-amino-1-(4-(p-toluenesulfonyloxy)phenyl)propane, N,N-dimethyl-2-amino-1-(4-(p-toluenesulfonyloxy)phenyl)propane, N-(t-butyloxycarbonyl)-2-amino-1-(3-(p-toluenesulfonyloxy)phenyl)propane, N-benzyloxycarbonyl-2-amino-1-(3-(p-toluenesulfonyloxy)phenyl)propane, N-(9-fluorenylmethyloxycarbonyl)-2-amino-1-(3-(p-toluenesulfonyloxy)phenyl)propane, N-acetyl-2-amino-1-(3-(p-toluenesulfonyloxy)phenyl)propane, N-benzoyl-2-amino-1-(3-(p-toluenesulfonyloxy)phenyl)propane, N-benzyl-2-amino-1-(3-(p-toluenesulfonyloxy)phenyl)propane, N,N-dimethyl-2-amino-1-(3-(p-toluenesulfonyloxy)phenyl)propane, N-(t-butyloxycarbonyl)-2-amino-1-(2-(p-toluenesulfonyloxy)phenyl)propane, N-benzyloxycarbonyl-2-amino-1-(4-(p-toluenesulfonyloxy)phenyl)propane, N-(9-fluorenylmethyloxycarbonyl)-2-amino-1-(2-(p-toluenesulfonyloxy)phenyl)propane, N-acetyl-2-amino-1-(2-(p-toluenesulfonyloxy)phenyl)propane, N-benzoyl-2-amino-1-(2-(p-toluenesulfonyloxy)phenyl)propane, N-benzyl-2-amino-1-(2-(p-toluenesulfonyloxy)phenyl)propane, N,N-dimethyl-2-amino-1-(2-(p-toluenesulfonyloxy)phenyl)propane, N-(t-butyloxycarbonyl)-2-amino-1-(4-(p-toluenesulfonyloxy)phenyl)butane, N-benzyloxycarbonyl-2-amino-1-(4-(p-toluenesulfonyloxy)phenyl)butane, N-(9-fluorenylmethyloxycarbonyl)-2-amino-1-(4-(p-toluenesulfonyloxy)phenyl)butane, N-acetyl-2-amino-1-(4-(p-toluenesulfonyloxy)phenyl)butane, N-benzoyl-2-amino-1-(4-(p-toluenesulfonyloxy)phenyl)butane, N-benzyl-2-amino-1-(4-(p-toluenesulfonyloxy)phenyl)butane, N,N- dimethyl-2-amino-1-(4-(p-toluenesulfonyloxy)phenyl)butane, N-(t-butyloxycarbonyl)-2-amino-1-(3-(p-toluenesulfonyloxy)phenyl)butane,
N-benzyloxycarbonyl-2-amino-1-(3-(p-toluenesulfonyloxy)phenyl)butane, N-(9-fluorenylmethyloxycarbonyl)-2-amino-1-(3-(p-toluenesulfonyloxy)phenyl)butane, N-acetyl-2-amino-1-(3-(p-toluenesulfonyloxy)phenyl)butane, N-benzoyl-2-amino-1-(3-(p-toluenesulfonyloxy)phenyl)butane, N-benzyl-2-amino-1-(3-(p-toluenesulfonyloxy)phenyl)butane, N,N-dimethyl-2-amino-1-(3-(p-toluenesulfonyloxy)phenyl)butane, <amino, alcohol>

N-(t-butyloxycarbonyl)-4-(p-toluenesulfonyloxy)-α-aminobenzylalcohol, N-(t-butyloxycarbonyl)-4-methanesulfonyloxy-α-aminobenzylalcohol, N-(t-butyloxycarbonyl)-4-benzenesulfonyloxy-α-aminobenzylalcohol, N-(t-butyloxycarbonyl)-4-(p-toluenesulfonyloxy)-α-aminobenzylalcohol methyl ether, N-(t-butyloxycarbonyl)-4-methanesulfonyloxy-α-aminobenzylalcohol methyl ether, N-(t-butyloxycarbonyl)-4-benzenesulfonyloxy-α-aminobenzylalcohol methyl ether, N-(t-butyloxycarbonyl)-4-(p-toluenesulfonyloxy)-α-aminobenzylalcohol benzyl ether, N-(t-butyloxycarbonyl)-4-methanesulfonyloxy-α-aminobenzylalcohol benzyl ether, N-(t-butyloxycarbonyl)-4-benzenesulfonyloxy-α-aminobenzylalcohol benzyl ether, N-(t-butyloxycarbonyl)-4-(p-toluenesulfonyloxy)-α-aminobenzyl acetate, N-(t-butyloxycarbonyl)-4-methanesulfonyloxy-α-aminobenzyl acetate, 4-benzenesulfonyloxy-α-aminobenzyl acetate, N-(t-butyloxycarbonyl)-4-(p-toluenesulfonyloxy)-α-aminomethylbenzylalcohol, N-(t-butyloxycarbonyl)-4-methanesulfonyloxy-α-aminomethylbenzylalcohol, N-(t-butyloxycarbonyl)-4-benzenesulfonyloxy-α-aminomethylbenzylalcohol, N-(t-butyloxycarbonyl)-4-(p-toluenesulfonyloxy)-α-aminomethylbenzylalcohol methyl ether, N-(t-butyloxycarbonyl)-4-methanesulfonyloxy-α-aminomethylbenzylalcohol methyl ether, N-(t-butyloxycarbonyl)-4-benzenesulfonyloxy-α-aminomethylbenzylalcohol methyl ether, N-(t-butyloxycarbonyl)-4-(p-toluenesulfonyloxy)-α-aminomethylbenzylalcohol benzyl ether, N-(t-butyloxycarbonyl)-4-methanesulfonyloxy-α-aminomethylbenzylalcohol benzyl ether, N-(t-butyloxycarbonyl)-4-benzenesulfonyloxy-α-aminomethylbenzylalcohol benzyl ether, N-(t-butyloxycarbonyl)-4-(p-toluenesulfonyloxy)-α-aminomethylbenzyl acetate, N-(t-butyloxycarbonyl)-4-methanesulfonyloxy-α-aminomethylbenzyl acetate, 4-benzenesulfonyloxy-α-aminomethylbenzyl acetate, N-(t-butyloxycarbonyl)-3-(p-toluenesulfonyloxy)-α-aminomethylbenzylalcohol, N-(t-butyloxycarbonyl)-3-methanesulfonyloxy-α-aminomethylbenzylalcohol, N-(t-butyloxycarbonyl)-3-benzenesulfonyloxy-α-aminomethylbenzylalcohol, N-(t-butyloxycarbonyl)-3-(p-toluenesulfonyloxy)-α-aminomethylbenzylalcohol methyl ether, N-(t-butyloxycarbonyl)-3-methanesulfonyloxy-α-aminomethylbenzylalcohol methyl ether, N-(t-butyloxycarbonyl)-3-benzenesulfonyloxy-α-aminomethylbenzylalcohol methyl ether, N-(t-butyloxycarbonyl)-3-(p-toluenesulfonyloxy)-α-aminomethylbenzylalcohol benzyl ether, N-(t-butyloxycarbonyl)-3-methanesulfonyloxy-α-aminomethylbenzylalcohol benzyl ether, N-(t-butyloxycarbonyl)-3-benzenesulfonyloxy-α-aminomethylbenzylalcohol benzyl ether, N-(t-butyloxycarbonyl)-3-(p-toluenesulfonyloxy)-α-aminomethylbenzyl acetate, N-(t-butyloxycarbonyl)-3-methanesulfonyloxy-α-aminomethylbenzyl acetate 3-benzenesulfonyloxy-α-aminomethylbenzyl acetate, N-(t-butyloxycarbonyl)-2-(p-toluenesulfonyloxy)-α-aminomethylbenzylalcohol, N-(t-butyloxycarbonyl)-2-methanesulfonyloxy-α-aminomethylbenzylalcohol, N-(t-butyloxycarbonyl)-2-benzenesulfonyloxy-α-aminomethylbenzylalcohol, N-(t-butyloxycarbonyl)-2-(p-toluenesulfonyloxy)-α-aminomethylbenzylalcohol methyl ether, N-(t-butyloxycarbonyl)-2-methanesulfonyloxy-α-aminomethylbenzylalcohol methyl ether, N-(t-butyloxycarbonyl)-2-benzenesulfonyloxy-α-aminomethylbenzylalcohol methyl ether, N-(t-butyloxycarbonyl)-2-(p-toluenesulfonyloxy)-α-aminomethylbenzylalcohol benzyl ether, N-(t-butyloxycarbonyl)-2-methanesulfonyloxy-α-aminomethylbenzylalcohol benzyl ether, N-(t-butyloxycarbonyl)-2-benzenesulfonyloxy-α-aminomethylbenzylalcohol benzyl ether, N-(t-butyloxycarbonyl)-2-(p-toluenesulfonyloxy)-α-aminomethylbenzyl acetate, N-(t-butyloxycarbonyl)-2-methanesulfonyloxy-α-aminomethylbenzyl acetate, N-(t-butyloxycarbonyl)-2-benzenesulfonyloxy-α-aminomethylbenzyl acetate, 1-(2,2-dimethyl-5-oxazolidinyl-3-(p-toluenesulfonyloxy)benzene, N-(t-butyloxycarbonyl)-4-(p-toluenesulfonyloxy)-α-methyl-α-aminomethylbenzylalcohol, N-(t-butyloxycarbonyl)-4-methanesulfonyloxy-α-methyl-α-aminomethylbenzylalcohol, N-(t-butyloxycarbonyl)-4-benzenesulfonyloxy-α-methyl-α-aminomethylbenzylalcohol, N-(t-butyloxycarbonyl)-4-(p-toluenesulfonyloxy)-α-methyl-α-aminomethylbenzylalcohol methyl ether, N-(t-butyloxycarbonyl)-4-methanesulfonyloxy-α-methyl-α-aminomethylbenzylalcohol methyl ether, N-(t-butyloxycarbonyl)-4-benzenesulfonyloxy-α-methyl-α-aminomethylbenzylalcohol methyl ether, N-(t-butyloxycarbonyl)-4-(p-toluenesulfonyloxy)-α-methyl-α-aminomethylbenzylalcohol benzyl ether, N-(t-butyloxycarbonyl)-4-methanesulfonyloxy-α-methyl-α-aminomethylbenzylalcohol benzyl ether, N-(t-butyloxycarbonyl)-4-benzenesulfonyloxy-α-methyl-α-aminomethylbenzylalcohol benzyl ether, N-(t-butyloxycarbonyl)-4-(p-toluenesulfonyloxy)-α-methyl-α-aminomethylbenzyl acetate, N-(t-butyloxycarbonyl)-4-methanesulfonyloxy-α-methyl-α-aminomethylbenzyl acetate, N-(t-butyloxycarbonyl)-4-benzenesulfonyloxy-α-methyl-α-aminomethylbenzyl acetate, N-(t-butyloxycarbonyl)-3-(p-toluenesulfonyloxy)-α-methyl-α-aminomethylbenzylalcohol, N-(t-butyloxycarbonyl)-3-methanesulfonyloxy-α-methyl-α-aminomethylbenzylalcohol, N-(t-butyloxycarbonyl)-3-benzenesulfonyloxy-α-methyl-α-aminomethylbenzylalcohol, N-(t-butyloxycarbonyl)-3-(p-toluenesulfonyloxy)-α-methyl-α-aminomethylbenzylalcohol methyl ether, N-(t-butyloxycarbonyl)-3-methanesulfonyloxy-α-methyl-α-aminomethylbenzylalcohol methyl ether, N-(t-butyloxycarbonyl)-3-benzenesulfonyloxy-α-methyl-α-aminomethylbenzylalcohol methyl ether, N-(t-butyloxycarbonyl)-3-(p-toluenesulfonyloxy)-α-methyl-α-aminomethylbenzylalcohol benzyl ether, N-(t-butyloxycarbonyl)-3-methanesulfonyloxy-α-methyl-α-aminomethylbenzylalcohol benzyl ether, N-(t-butyloxycarbonyl)-3-benzenesulfonyloxy-α-methyl-α-aminomethylbenzylalcohol benzyl ether, N-(t-butyloxycarbonyl)-3-(p-toluenesulfonyloxy)-α-methyl-α-aminomethylbenzyl acetate, N-(t-butyloxycarbonyl)-3-methanesulfonyloxy-α-methyl-α-aminomethylbenzyl acetate, N-(t-butyloxycarbonyl)-3-benzenesulfonyloxy-α-methyl-α-aminomethylbenzyl acetate, N-(t-butyloxycarbonyl)-1-amino-2-(4-(p-toluenesulfonyloxy)phenyl)ethylalcohol, N-(t-butyloxycarbonyl)-1-amino-2-(4-methanesulfonyloxyphenyl)ethylalcohol, N-(t-butyloxycarbonyl)-1-amino-2-(4-benzenesulfonyloxyphenyl)ethylalcohol, N-(t-butyloxycarbonyl)-1-amino-2-(4-(p-toluenesulfonyloxy)phenyl)ethylalcohol methyl ether, N-(t-butyloxycarbonyl)-1-amino-2-(4-methanesulfonyloxyphenyl)ethylalcohol methyl ether, N-(t-butyloxycarbonyl)-1-amino-2-(4-benzenesulfonyloxyphenyl)ethylalcohol methyl ether, N-(t-butyloxycarbonyl)-1-amino-2-(4-(p-toluenesulfonyloxy)phenyl)ethylalcohol benzyl ether, N-(t-butyloxycarbonyl)-1-amino-2-(4-methanesulfonyloxyphenyl)ethylalcohol benzyl ether, N-(t-butyloxycarbonyl)-1-amino-2-(4-benzenesulfonyloxyphenyl)ethylalcohol benzyl ether, N-(t-butyloxycarbonyl)-1-amino-2-(4-(p-toluenesulfonyloxy)phenyl)ethyl acetate, N-(t-butyloxycarbonyl)-1-amino-2-(4-methanesulfonyloxyphenyl)ethyl acetate, N-(t-butyloxycarbonyl)-1-amino-2-(4-benzenesulfonyloxyphenyl)ethyl acetate, N-(t-butyloxycarbonyl)-2-amino-3-(4-(p-toluenesulfonyloxy)phenyl)propylalcohol, N-(t-butyloxycarbonyl)-2-amino-3-(4-methanesulfonyloxyphenyl)propylalcohol, N-(t-butyloxycarbonyl)-2-amino-3-(4-benzenesulfonyloxyphenyl)propylalcohol, N-(t-butyloxycarbonyl)-2-amino-3-(4-(p-toluenesulfonyloxy)phenyl)propylalcohol methyl ether, N-(t-butyloxycarbonyl)-2-amino-3-(4-methanesulfonyloxyphenyl)propylalcohol methyl ether, N-(t-butyloxycarbonyl)-2-amino-3-(4-benzenesulfonyloxyphenyl)propylalcohol methyl ether, N-(t-butyloxycarbonyl)-2-amino-3-(4-(p-toluenesulfonyloxy)phenyl)propylalcohol benzyl ether, N-(t-butyloxycarbonyl)-2-amino-3-(4-methanesulfonyloxyphenyl)propylalcohol benzyl ether, N-(t-butyloxycarbonyl)-2-amino-3-(4-benzenesulfonyloxyphenyl)propylalcohol benzyl ether, N-(t-butyloxycarbonyl)-2-amino-3-(4-(p-toluenesulfonyloxy)phenyl)propyl acetate, N-(t-butyloxycarbonyl)-2-amino-3-(4-methanesulfonyloxyphenyl)propyl acetate, N-(t-butyloxycarbonyl)-2-amino-3-(4-benzenesulfonyloxyphenyl)propyl acetate, N-(t-butyloxycarbonyl)-O-(p-toluenesulfonyl)tyrosine methyl ester, N-(t-butyloxycarbonyl)-O-(p-toluenesulfonyl)tyrosine ethyl ester, N-(t-butyloxycarbonyl)-O-(p-toluenesulfonyl)tyrosine isopropyl ester, N-(t-butyloxycarbonyl)-O-(p-toluenesulfonyl)tyrosine t-butyl ester, N-(t-butyloxycarbonyl)-O-(p-toluenesulfonyl)tyrosine benzyl ester, N-(t-butyloxycarbonyl)-O-methanesulfonyltyrosine methyl ester, N-(t-butyloxycarbonyl)-O-methanesulfonyltyrosine ethyl ester, N-(t-butyloxycarbonyl)-O-methanesulfonyltyrosine isopropyl ester, N-(t-butyloxycarbonyl)-O-methanesulfonyltyrosine t-butyl ester, N-(t-butyloxycarbonyl)-O-methanesulfonyltyrosine benzyl ester, N-(t-butyloxycarbonyl)-O-benzenesulfonyltyrosine methyl ester, N-(t-butyloxycarbonyl)-O-benzenesulfonyltyrosine ethyl ester, N-(t-butyloxycarbonyl)-O-benzenesulfonyltyrosine isopropyl ester, N-(t-butyloxycarbonyl)-O-benzenesulfonyltyrosine t-butyl ester, N-(t-butyloxycarbonyl)-O-benzenesulfonyltyrosine benzyl ester, N-acetyl-O-(p-toluenesulfonyl)tyrosine methyl ester, N-acetyl-O-(p-toluenesulfonyl)tyrosine ethyl ester, N-acetyl-O-(p-toluenesulfonyl)tyrosine isopropyl ester, N-acetyl-O-(p-toluenesulfonyl)tyrosine t-butyl ester, N-acetyl-O-(p-toluenesulfonyl)tyrosine benzyl ester, N-acetyl-O-methanesulfonyltyrosine methyl ester, N-acetyl-O-methanesulfonyltyrosine ethyl ester, N-acetyl-O-methanesulfonyltyrosine isopropyl ester, N-acetyl-O-methanesulfonyltyrosine t-butyl ester, N-acetyl-O-methanesulfonyltyrosine benzyl ester, N-acetyl-O-benzenesulfonyltyrosine methyl ester, N-acetyl-O-benzenesulfonyltyrosine ethyl ester, N-acetyl-O-benzenesulfonyltyrosine isopropyl ester, N-acetyl-O-benzenesulfonyltyrosine t-butyl ester, N-acetyl-O-benzenesulfonyltyrosine benzyl ester, N-benzyl-O-(p-toluenesulfonyl)tyrosine methyl ester, N-benzyl-O-(p-toluenesulfonyl)tyrosine ethyl ester, N-benzyl-O-(p-toluenesulfonyl)tyrosine isopropyl ester, N-benzyl-O-(p-toluenesulfonyl)tyrosine t-butyl ester, N-benzyl-O-(p-toluenesulfonyl)tyrosine benzyl ester, N-benzyl-O-methanesulfonyltyrosine methyl ester, N-benzyl-O-methanesulfonyltyrosine ethyl ester, N-benzyl-O-methanesulfonyltyrosine isopropyl ester, N-benzyl-O-methanesulfonyltyrosine t-butyl ester, N-benzyl-O-methanesulfonyltyrosine benzyl ester, N-benzyl-O-benzenesulfonyltyrosine methyl ester, N-benzyl-O-benzenesulfonyltyrosine ethyl ester, N-benzyl-O-benzenesulfonyltyrosine isopropyl ester, N-benzyl-O-benzenesulfonyltyrosine t-butyl ester, N-benzyl-O-benzenesulfonyltyrosine benzyl ester, N-(9-fluorenylmethoxycarbonyl)-O-(p-toluenesulfonyl)tyrosine methyl ester, N-(9-fluorenylmethoxycarbonyl)-O-(p-toluenesulfonyl)tyrosine ethyl ester, N-(9-fluorenylmethoxycarbonyl)-O-(p-toluenesulfonyl)tyrosine isopropyl ester, N-(9-fluorenylmethoxycarbonyl)-O-(p-toluenesulfonyl)tyrosine t-butyl ester, N-(9-fluorenylmethoxycarbonyl)-O-(p-toluenesulfonyl)tyrosine benzyl ester, N-(9-fluorenylmethoxycarbonyl)-O-methanesulfonyltyrosine methyl ester, N-(9-fluorenylmethoxycarbonyl)-O-methanesulfonyltyrosine ethyl ester, N-(9-fluorenylmethoxycarbonyl)-O-methanesulfonyltyrosine isopropyl ester, N-(9-fluorenylmethoxycarbonyl)-O-methanesulfonyltyrosine t-butyl ester, N-(9-fluorenylmethoxycarbonyl)-O-methanesulfonyltyrosine benzyl ester, N-(9-fluorenylmethoxycarbonyl)-O-benzenesulfonyltyrosine methyl ester, N-(9-fluorenylmethoxycarbonyl)-O-benzenesulfonyltyrosine ethyl ester, N-(9-fluorenylmethoxycarbonyl)-O-benzenesulfonyltyrosine isopropyl ester, N-(9-fluorenylmethoxycarbonyl)-O-benzenesulfonyltyrosine t-butyl ester, N-(9-fluorenylmethoxycarbonyl)-O-benzenesulfonyltyrosine benzyl ester, N-benzyloxycarbonyl-O-(p-toluenesulfonyl)tyrosine methyl ester, N-benzyloxycarbonyl-O-(p-toluenesulfonyl)tyrosine ethyl ester, N-benzyloxycarbonyl-O-(p-toluenesulfonyl)tyrosine isopropyl ester, N-benzyloxycarbonyl-O-(p-toluenesulfonyl)tyrosine t-butyl ester, N-benzyloxycarbonyl-O-(p-toluenesulfonyl)tyrosine benzyl ester, N-benzyloxycarbonyl-O-methanesulfonyltyrosine methyl ester,
N-benzyloxycarbonyl-O-methanesulfonyltyrosine ethyl ester,
N-benzyloxycarbonyl-O-methanesulfonyltyrosine isopropyl ester, N-benzyloxycarbonyl-O-methanesulfonyltyrosine t-butyl ester, N-benzyloxycarbonyl-4-mesylphenylglycine benzyl ester,
N-benzyloxycarbonyl-O-benzenesulfonyltyrosine methyl ester,
N-benzyloxycarbonyl-O-benzenesulfonyltyrosine ethyl ester,
N-benzyloxycarbonyl-O-benzenesulfonyltyrosine isopropyl ester, N-benzyloxycarbonyl-O-benzenesulfonyltyrosine t-butyl ester, N-benzyloxycarbonyl-O-benzenesulfonyltyrosine benzyl ester,
N-(t-butyloxycarbonyl)-O-(p-toluenesulfonyl)-m-tyrosine methyl ester, N-(t-butyloxycarbonyl)-O-(p-toluenesulfonyl)-m-tyrosine ethyl ester, N-(t-butyloxycarbonyl)-O-(p-toluenesulfonyl)-m-tyrosine isopropyl ester, N-(t-butyloxycarbonyl)-O-(p-toluenesulfonyl)-m-tyrosine t-butyl ester, N-(t-butyloxycarbonyl)-O-(p-toluenesulfonyl)-m-tyrosine benzyl ester,
N-(t-butyloxycarbonyl)-O-methanesulfonyl-m-tyrosine methyl ester, N-(t-butyloxycarbonyl)-O-methanesulfonyl-m-tyrosine ethyl ester, N-(t-butyloxycarbonyl)-O-methanesulfonyl-m-tyrosine isopropyl ester, N-(t-butyloxycarbonyl)-O-methanesulfonyl-m-tyrosine t-butyl ester, N-(t-butyloxycarbonyl)-O-methanesulfonyl-m-tyrosine benzyl ester,
N-(t-butyloxycarbonyl)-O-benzenesulfonyl-m-tyrosine methyl ester, N-(t-butyloxycarbonyl)-O-benzenesulfonyl-m-tyrosine ethyl ester, N-(t-butyloxycarbonyl)-O-benzenesulfonyl-m-tyrosine isopropyl ester, N-(t-butyloxycarbonyl)-O-benzenesulfonyl-m-tyrosine t-butyl ester, N-(t-butyloxycarbonyl)-O-benzenesulfonyl-m-tyrosine benzyl ester,
N-acetyl-O-(p-toluenesulfonyl)-m-tyrosine methyl ester, N-acetyl-O-(p-toluenesulfonyl)-m-tyrosine ethyl ester, N-acetyl-O-(p-toluenesulfonyl)-m-tyrosine isopropyl ester, N-acetyl-O-(p-toluenesulfonyl)-m-tyrosine t-butyl ester, N-acetyl-O-(p-toluenesulfonyl)-m-tyrosine benzyl ester, N-acetyl-O-methanesulfonyl-m-tyrosine methyl ester, N-acetyl-O-methanesulfonyl-m-tyrosine ethyl ester, N-acetyl-O-methanesulfonyl-m-tyrosine isopropyl ester, N-acetyl-O-methanesulfonyl-m-tyrosine t-butyl ester, N-acetyl-O-methanesulfonyl-m-tyrosine benzyl ester, N-acetyl-O-benzenesulfonyl-m-tyrosine methyl ester, N-acetyl-O-benzenesulfonyl-m-tyrosine ethyl ester, N-acetyl-O-benzenesulfonyl-m-tyrosine isopropyl ester, N-acetyl-O-benzenesulfonyl-m-tyrosine t-butyl ester, N-acetyl-O-benzenesulfonyl-m-tyrosine benzyl ester,
N-benzyl-O-(p-toluenesulfonyl)-m-tyrosine methyl ester, N-benzyl-O-(p-toluenesulfonyl)-m-tyrosine ethyl ester, N-benzyl-O-(p-toluenesulfonyl)-m-tyrosine isopropyl ester, N-benzyl-O-(p-toluenesulfonyl)-m-tyrosine t-butyl ester, N-benzyl-O-(p-toluenesulfonyl)-m-tyrosine benzyl ester, N-benzyl-O-methanesulfonyl-m-tyrosine methyl ester, N-benzyl-O-methanesulfonyl-m-tyrosine ethyl ester, N-benzyl-O-methanesulfonyl-m-tyrosine isopropyl ester, N-benzyl-O-methanesulfonyl-m-tyrosine t-butyl ester, N-benzyl-O-methanesulfonyl-m-tyrosine benzyl ester, N-benzyl-O-benzenesulfonyl-m-tyrosine methyl ester, N-benzyl-O-benzenesulfonyl-m-tyrosine ethyl ester, N-benzyl-O-benzenesulfonyl-m-tyrosine isopropyl ester, N-benzyl-O-benzenesulfonyl-m-tyrosine t-butyl ester, N-benzyl-O-benzenesulfonyl-m-tyrosine benzyl ester,
N-(9-fluorenylmethoxycarbonyl)-O-(p-toluenesulfonyl)-m-tyrosine methyl ester, N-(9-fluorenylmethoxycarbonyl)-O-(p-toluenesulfonyl)-m-tyrosine ethyl ester, N-(9-fluorenylmethoxycarbonyl)-O-(p-toluenesulfonyl)-m-tyrosine isopropyl ester, N-(9-fluorenylmethoxycarbonyl)-O-(p-toluenesulfonyl)-m-tyrosine t-butyl ester, N-(9-fluorenylmethoxycarbonyl)-O-(p-toluenesulfonyl)-m-tyrosine benzyl ester, N-(9-fluorenylmethoxycarbonyl)-O-methanesulfonyl-m-tyrosine methyl ester, N-(9-fluorenylmethoxycarbonyl)-O-methanesulfonyl-m-tyrosine ethyl ester, N-(9-fluorenylmethoxycarbonyl)-O-methanesulfonyl-m-tyrosine isopropyl ester, N-(9-fluorenylmethoxycarbonyl)-O-methanesulfonyl-m-tyrosine t-butyl ester, N-(9-fluorenylmethoxycarbonyl)-O-methanesulfonyl-m-tyrosine benzyl ester, N-(9-fluorenylmethoxycarbonyl)-O-benzenesulfonyl-m-tyrosine methyl ester, N-(9-fluorenylmethoxycarbonyl)-O-benzenesulfonyl-m-tyrosine ethyl ester, N-(9-fluorenylmethoxycarbonyl)-O-benzenesulfonyl-m-tyrosine isopropyl ester, N-(9-fluorenylmethoxycarbonyl)-O-benzenesulfonyl-m-tyrosine t-butyl ester, N-(9-fluorenylmethoxycarbonyl)-O-benzenesulfonyl-m-tyrosine benzyl ester,
N-benzyloxycarbonyl-O-(p-toluenesulfonyl)-m-tyrosine methyl ester, N-benzyloxycarbonyl-O-(p-toluenesulfonyl)-m-tyrosine ethyl ester, N-benzyloxycarbonyl-O-(p-toluenesulfonyl)-m-tyrosine isopropyl ester, N-benzyloxycarbonyl-O-(p-toluenesulfonyl)-m-tyrosine t-butyl ester, N-benzyloxycarbonyl-O-(p-toluenesulfonyl)-m-tyrosine benzyl ester, N-benzyloxycarbonyl-O-methanesulfonyl-m-tyrosine methyl ester, N-benzyloxycarbonyl-O-methanesulfonyl-m-tyrosine ethyl ester, N-benzyloxycarbonyl-O-methanesulfonyl-m-tyrosine isopropyl ester, N-benzyloxycarbonyl-O-methanesulfonyl-m-tyrosine t-butyl ester, N-benzyloxycarbonyl-4-mesylphenylglycine benzyl ester, N-benzyloxycarbonyl-O-benzenesulfonyl-m-tyrosine methyl ester, N-benzyloxycarbonyl-O-benzenesulfonyl-m-tyrosine ethyl ester, N-benzyloxycarbonyl-O-benzenesulfonyl-m-tyrosine isopropyl ester, N-benzyloxycarbonyl-O-benzenesulfonyl-m-tyrosine t-butyl ester, N-benzyloxycarbonyl-O-benzenesulfonyl-m-tyrosine benzyl ester,
N-(t-butyloxycarbonyl)-O-(p-toluenesulfonyl)-o-tyrosine methyl ester, N-(t-butyloxycarbonyl)-O-(p-toluenesulfonyl)-O-tyrosine ethyl ester, N-(t-butyloxycarbonyl)-O-(p-toluenesulfonyl)-O-tyrosine isopropyl ester, N-(t-butyloxycarbonyl)-O-(p-toluenesulfonyl)-O-tyrosine t-butyl ester, N-(t-butyloxycarbonyl)-O-(p-toluenesulfonyl)-O-tyrosine benzyl ester, N-(t-butyloxycarbonyl)-O-methanesulfonyl-O-tyrosine methyl ester, N-(t-butyloxycarbonyl)-O-methanesulfonyl-O-tyrosine ethyl ester,
N-(t-butyloxycarbonyl)-O-methanesulfonyl-O-tyrosine isopropyl ester, N-(t-butyloxycarbonyl)-O-methanesulfonyl-O-tyrosine t-butyl ester, N-(t-butyloxycarbonyl)-O-methanesulfonyl-O-tyrosine benzyl ester, N-(t-butyloxycarbonyl)-O-benzenesulfonyl-O-tyrosine methyl ester,
N-(t-butyloxycarbonyl)-O-benzenesulfonyl-O-tyrosine ethyl ester, N-(t-butyloxycarbonyl)-O-benzenesulfonyl-O-tyrosine isopropyl ester, N-(t-butyloxycarbonyl)-O-benzenesulfonyl-O-tyrosine t-butyl ester, N-(t-butyloxycarbonyl)-O-benzenesulfonyl-O-tyrosine benzyl ester,
N-acetyl-O-(p-toluenesulfonyl)-O-tyrosine methyl ester, N-acetyl-O-(p-toluenesulfonyl)-O-tyrosine ethyl ester, N-acetyl-O-(p-toluenesulfonyl)-O-tyrosine isopropyl ester, N-acetyl-O-(p-toluenesulfonyl)-O-tyrosine t-butyl ester, N-acetyl-O-(p-toluenesulfonyl)-O-tyrosine benzyl ester, N-acetyl-O-methanesulfonyl-O-tyrosine methyl ester, N-acetyl-O-methanesulfonyl-O-tyrosine ethyl ester, N-acetyl-O-methanesulfonyl-O-tyrosine isopropyl ester, N-acetyl-O-methanesulfonyl-O-tyrosine t-butyl ester, N-acetyl-O-methanesulfonyl-O-tyrosine benzyl ester, N-acetyl-O-benzenesulfonyl-O-tyrosine methyl ester, N-acetyl-O-benzenesulfonyl-O-tyrosine ethyl ester, N-acetyl-O-benzenesulfonyl-O-tyrosine isopropyl ester, N-acetyl-O-benzenesulfonyl-O-tyrosine t-butyl ester, N-acetyl-O-benzenesulfonyl-O-tyrosine benzyl ester, N-benzyl-O-(p-toluenesulfonyl)-O-tyrosine methyl ester, N-benzyl-O-(p-toluenesulfonyl)-O-tyrosine ethyl ester, N-benzyl-O-(p-toluenesulfonyl)-O-tyrosine isopropyl ester, N-benzyl-O-(p-toluenesulfonyl)-O-tyrosine t-butyl ester, N-benzyl-O-(p-toluenesulfonyl)-O-tyrosine benzyl ester, N-benzyl-O-methanesulfonyl-O-tyrosine methyl ester, N-benzyl-O-methanesulfonyl-O-tyrosine ethyl ester, N-benzyl-O-methanesulfonyl-O-tyrosine isopropyl ester, N-benzyl-O-methanesulfonyl-O-tyrosine t-butyl ester, N-benzyl-O-methanesulfonyl-O-tyrosine benzyl ester, N-benzyl-O-benzenesulfonyl-O-tyrosine methyl ester, N-benzyl-O-benzenesulfonyl-O-tyrosine ethyl ester, N-benzyl-O-benzenesulfonyl-O-tyrosine isopropyl ester, N-benzyl-O-benzenesulfonyl-O-tyrosine t-butyl ester, N-benzyl-O-benzenesulfonyl-O-tyrosine benzyl ester, N-(9-fluorenylmethoxycarbonyl)-O-(p-toluenesulfonyl)-O-tyrosine methyl ester, N-(9-fluorenylmethoxycarbonyl)-O-(p-toluenesulfonyl)-O-tyrosine ethyl ester, N-(9-fluorenylmethoxycarbonyl)-O-(p-toluenesulfonyl)-O-tyrosine isopropyl ester, N-(9-fluorenylmethoxycarbonyl)-O-(p-toluenesulfonyl)-O-tyrosine t-butyl ester, N-(9-fluorenylmethoxycarbonyl)-O-(p-toluenesulfonyl)-O-tyrosine benzyl ester, N-(9-fluorenylmethoxycarbonyl)-O-methanesulfonyl-O-tyrosine methyl ester, N-(9-fluorenylmethoxycarbonyl)-O-methanesulfonyl-O-tyrosine ethyl ester, N-(9-fluorenylmethoxycarbonyl)-O-methanesulfonyl-O-tyrosine isopropyl ester, N-(9-fluorenylmethoxycarbonyl)-O-methanesulfonyl-O-tyrosine t-butyl ester, N-(9-fluorenylmethoxycarbonyl)-O-methanesulfonyl-O-tyrosine benzyl ester, N-(9-fluorenylmethoxycarbonyl)-O-benzenesulfonyl-O-tyrosine methyl ester, N-(9-fluorenylmethoxycarbonyl)-O-benzenesulfonyl-O-tyrosine ethyl ester, N-(9-fluorenylmethoxycarbonyl)-O-benzenesulfonyl-O-tyrosine isopropyl ester, N-(9-fluorenylmethoxycarbonyl)-O-benzenesulfonyl-O-tyrosine t-butyl ester, N-(9-fluorenylmethoxycarbonyl)-O-benzenesulfonyl-O-tyrosine benzyl ester, N-benzyloxycarbonyl-O-(p-toluenesulfonyl)-O-tyrosine methyl ester, N-benzyloxycarbonyl-O-(p-toluenesulfonyl)-O-tyrosine ethyl ester, N-benzyloxycarbonyl-O-(p-toluenesulfonyl)-O-tyrosine isopropyl ester, N-benzyloxycarbonyl-O-(p-toluenesulfonyl)-O-tyrosine t-butyl ester, N-benzyloxycarbonyl-O-(p-toluenesulfonyl)-O-tyrosine benzyl ester, N-benzyloxycarbonyl-O-methanesulfonyl-O-tyrosine methyl ester, N-benzyloxycarbonyl-O-methanesulfonyl-O-tyrosine ethyl ester, N-benzyloxycarbonyl-O-methanesulfonyl-O-tyrosine isopropyl ester, N-benzyloxycarbonyl-O-methanesulfonyl-O-tyrosine t-butyl ester, N-benzyloxycarbonyl-4-mesylphenylglycine benzyl ester, N-benzyloxycarbonyl-O-benzenesulfonyl-O-tyrosine methyl ester, N-benzyloxycarbonyl-O-benzenesulfonyl-O-tyrosine ethyl ester, N-benzyloxycarbonyl-O-benzenesulfonyl-O-tyrosine isopropyl ester, N-benzyloxycarbonyl-O-benzenesulfonyl-O-tyrosine t-butyl ester, N-benzyloxycarbonyl-O-benzenesulfonyl-O-tyrosine benzyl ester, N-(t-butyloxycarbonyl)-2-(4-(p-toluenesulfonyloxy)phenyl)glycine methyl ester, N-(t-butyloxycarbonyl)-2-(4-(p-toluenesulfonyloxy)phenyl)glycine ethyl ester, N-(t-butyloxycarbonyl)-2-(4-(p-toluenesulfonyloxy)phenyl)glycine isopropyl ester, N-(t-butyloxycarbonyl)-2-(4-(p-toluenesulfonyloxy)phenyl)glycine t-butyl ester, N-(t-butyloxycarbonyl)-2-(4-(p-toluenesulfonyloxy)phenyl)glycine benzyl ester, N-(t-butyloxycarbonyl)-2-(4-methanesulfonyloxyphenyl)glycine methyl ester, N-(t-butyloxycarbonyl)-2-(4-methanesulfonyloxyphenyl)glycine ethyl ester, N-(t-butyloxycarbonyl)-2-(4-methanesulfonyloxyphenyl)glycine isopropyl ester, N-(t-butyloxycarbonyl)-2-(4-methanesulfonyloxyphenyl)glycine t-butyl ester, N-(t-butyloxycarbonyl)-2-(4-methanesulfonyloxyphenyl)glycine benzyl ester, N-(t-butyloxycarbonyl)-2-(4-benzenesulfonyloxyphenyl)glycine methyl ester, N-(t-butyloxycarbonyl)-2-(4-benzenesulfonyloxyphenyl)glycine ethyl ester, N-(t-butyloxycarbonyl)-2-(4-benzenesulfonyloxyphenyl)glycine isopropyl ester, N-(t-butyloxycarbonyl)-2-(4-benzenesulfonyloxyphenyl)glycine-t-butyl ester, N-(t-butyloxycarbonyl)-2-(4-benzenesulfonyloxyphenyl)glycine benzyl ester, N-acetyl-2-(4-(p-toluenesulfonyloxy)phenyl)glycine methyl ester, N-acetyl-2-(4-(p-toluenesulfonyloxy)phenyl)glycine ethyl ester, N-2-(4-(p-toluenesulfonyloxy)phenyl)glycine isopropyl ester, N-2-(4-(p-toluenesulfonyloxy)phenyl)glycine t-butyl ester, N-acetyl-2-(4-(p-toluenesulfonyloxy)phenyl)glycine benzyl ester, N-acetyl-2-(4-methanesulfonyloxyphenyl)glycine methyl ester, N-acetyl-2-(4-methanesulfonyloxyphenyl)glycine ethyl ester, N-acetyl-2-(4-methanesulfonyloxyphenyl)glycine isopropyl ester, N-acetyl-2-(4-methanesulfonyloxyphenyl)glycine t-butyl ester, N-acetyl-2-(4-methanesulfonyloxyphenyl)glycine benzyl ester, N-acetyl-2-(4-benzenesulfonyloxyphenyl)glycine methyl ester, N-acetyl-2-(4-benzenesulfonyloxyphenyl)glycine ethyl ester, N-acetyl-2-(4-benzenesulfonyloxyphenyl)glycine isopropyl ester, N-acetyl-2-(4-benzenesulfonyloxyphenyl)glycine t-butyl ester, N-acetyl-2-(4-benzenesulfonyloxyphenyl)glycine benzyl ester, N-benzyl-2-(4-(p-toluenesulfonyloxy)phenyl)glycine methyl ester, N-benzyl-2-(4-(p-toluenesulfonyloxy)phenyl)glycine ethyl ester, N-benzyl-2-(4-(p-toluenesulfonyloxy)phenyl)glycine isopropyl ester, N-benzyl-2-(4-(p-toluenesulfonyloxy)phenyl)glycine t-butyl ester, N-benzyl-2-(4-(p-toluenesulfonyloxy)phenyl)glycine benzyl ester, N-benzyl-2-(4-methanesulfonyloxyphenyl)glycine methyl ester, N-benzyl-2-(4-methanesulfonyloxyphenyl)glycine ethyl ester, N-benzyl-2-(4-methanesulfonyloxyphenyl)glycine isopropyl ester, N-benzyl-2-(4-methanesulfonyloxyphenyl)glycine t-butyl ester, N-benzyl-2-(4-methanesulfonyloxyphenyl)glycine benzyl ester, N-benzyl-2-(4-benzenesulfonyloxyphenyl)glycine methyl ester, N-benzyl-2-(4-benzenesulfonyloxyphenyl)glycine ethyl ester, N-benzyl-2-(4-benzenesulfonyloxyphenyl)glycine isopropyl ester, N-benzyl-2-(4-benzenesulfonyloxyphenyl)glycine t-butyl ester, N-benzyl-2-(4-benzenesulfonyloxyphenyl)glycine benzyl ester, N-(9-fluorenylmethoxycarbonyl)-2-(4-(p-toluenesulfonyloxy)phenyl)glycine methyl ester, N-(9-fluorenylmethoxycarbonyl)-2-(4-(p-toluenesulfonyloxy)phenyl)

glycine ethyl ester, N-(9-fluorenylmethoxycarbonyl)-2-(4-(p-toluenesulfonyloxy)phenyl)glycine isopropyl ester, N-(9-fluorenylmethoxycarbonyl)-2-(4-(p-toluenesulfonyloxy)phenyl)glycine t-butyl ester, N-(9-fluorenylmethoxycarbonyl)-2-(4-(p-toluenesulfonyloxy)phenyl)glycine benzyl ester, N-(9-fluorenylmethoxycarbonyl)-2-(4-methanesulfonyloxyphenyl)glycine methyl ester, N-(9-fluorenylmethoxycarbonyl)-2-(4-methanesulfonyloxyphenyl) glycine ethyl ester, N-(9-fluorenylmethoxycarbonyl)-2-(4-methanesulfonyloxyphenyl)glycine isopropyl ester, N-(9-fluorenylmethoxycarbonyl)-2-(4-methanesulfonyloxyphenyl)glycine t-butyl ester, N-(9-fluorenylmethoxycarbonyl)-2-(4-methanesulfonyloxyphenyl)glycine benzyl ester, N-(9-fluorenylmethoxycarbonyl)-2-(4-benzenesulfonyloxyphenyl)glycine methyl ester, N-(9-fluorenylmethoxycarbonyl)-2-(4-benzenesulfonyloxyphenyl)glycine ethyl ester, N-(9-fluorenylmethoxycarbonyl)-2-(4-benzenesulfonyloxyphenyl)glycine isopropyl ester, N-(9-fluorenylmethoxycarbonyl)-2-(4-benzenesulfonyloxyphenyl)glycine t-butyl ester, N-(9-fluorenylmethoxycarbonyl)-2-(4-(p-benzenesulfonyloxyphenyl)glycine benzyl ester, N-benzyloxycarbonyl-2-(4-(p-toluenesulfonyloxy)phenyl) glycine methyl ester, N-benzyloxycarbonyl-2-(4-(p-toluenesulfonyloxy)phenyl)glycine ethyl ester, N-benzyloxycarbonyl-2-(4-(p-toluenesulfonyloxy)phenyl)glycine isopropyl ester, N-benzyloxycarbonyl-2-(4-(p-toluenesulfonyloxy)phenyl)glycine t-butyl ester, N-benzyloxycarbonyl-2-(4-(p-toluenesulfonyloxy)phenyl)glycine benzyl ester, N-benzyloxycarbonyl-2-(4-methanesulfonyloxyphenyl)glycine methyl ester, N-benzyloxycarbonyl-2-(4-methanesulfonyloxyphenyl) glycine ethyl ester, N-benzyloxycarbonyl-2-(4-methanesulfonyloxyphenyl)glycine isopropyl ester, N-benzyloxycarbonyl-2-(4-methanesulfonyloxyphenyl)glycine t-butyl ester, N-benzyloxycarbonyl-2-(4-methanesulfonyloxyphenyl)glycine benzyl ester, N-benzyloxycarbonyl-2-(4-benzenesulfonyloxyphenyl)glycine methyl ester, N-benzyloxycarbonyl-2-(4-benzenesulfonyloxyphenyl)glycine ethyl ester, N-benzyloxycarbonyl-2-(4-benzenesulfonyloxyphenyl)glycine isopropyl ester, N-benzyloxycarbonyl-2-(4-benzenesulfonyloxyphenyl)glycine t-butyl ester, N-benzyloxycarbonyl-2-(4-benzenesulfonyloxyphenyl) glycine benzyl ester, N-(t-butyloxycarbonyl)-3-amino-3-(4-(p-toluenesulfonyloxy)phenyl)propanoic acid methyl ester, N-(t-butyloxycarbonyl)-3-amino-3-(4-(p-toluenesulfonyloxy)phenyl) propanoic acid ethyl ester, N-(t-butyloxycarbonyl)-3-amino-3-(4-(p-toluenesulfonyloxy)phenyl)propanoic acid isopropyl ester, N-(t-butyloxycarbonyl)-3-amino-3-(4-(p-toluenesulfonyloxy)phenyl)propanoic acid t-butyl ester, N-(t-butyloxycarbonyl)-3-amino-3-(4-(p-toluenesulfonyloxy)phenyl) propanoic acid benzyl ester, N-(t-butyloxycarbonyl)-3-amino-3-(4-methanesulfonyloxyphenyl)propanoic acid methyl ester, N-(t-butyloxycarbonyl)-3-amino-3-(4-methanesulfonyloxyphenyl)propanoic acid ethyl ester, N-(t-butyloxycarbonyl)-3-amino-3-(4-methanesulfonyloxyphenyl)propanoic acid isopropyl ester, N-(t-butyloxycarbonyl)-3-amino-3-(4-methanesulfonyloxyphenyl)propanoic acid t-butyl ester, N-(t-butyloxycarbonyl)-3-amino-3-(4-methanesulfonyloxyphenyl)propanoic acid benzyl ester, N-(t-butyloxycarbonyl)-3-amino-3-(4-benzenesulfonyloxyphenyl)propanoic acid methyl ester, N-(t-butyloxycarbonyl)-3-amino-3-(4-benzenesulfonyloxyphenyl)propanoic acid ethyl ester, N-(t-butyloxycarbonyl)-3-amino-3-(4-benzenesulfonyloxyphenyl)propanoic acid isopropyl ester, N-(t-butyloxycarbonyl)-3-amino-3-(4-benzenesulfonyloxyphenyl)propanoic acid t-butyl ester, N-(t-butyloxycarbonyl)-3-amino-3-(4-benzenesulfonyloxyphenyl)propanoic acid benzyl ester, N-acetyl-3-amino-3-(4-(p-toluenesulfonyloxy)phenyl)propanoic acid methyl ester, N-acetyl-3-amino-3-(4-(p-toluenesulfonyloxy)phenyl)propanoic acid ethyl ester, N-3-amino-3-(4-(p-toluenesulfonyloxy)phenyl)propanoic acid isopropyl ester, N-3-amino-3-(4-(p-toluenesulfonyloxy)phenyl)propanoic acid t-butyl ester, N-acetyl-3-amino-3-(4-(p-toluenesulfonyloxy)phenyl)propanoic acid benzyl ester, N-acetyl-3-amino-3-(4-methanesulfonyloxyphenyl)propanoic acid methyl ester, N-acetyl-3-amino-3-(4-methanesulfonyloxyphenyl)propanoic acid ethyl ester, N-acetyl-3-amino-3-(4-methanesulfonyloxyphenyl)propanoic acid isopropyl ester, N-acetyl-3-amino-3-(4-methanesulfonyloxyphenyl) propanoic acid t-butyl ester, N-acetyl-3-amino-3-(4-methanesulfonyloxyphenyl)propanoic acid benzyl ester, N-acetyl-3-amino-3-(4-benzenesulfonyloxyphenyl)propanoic acid methyl ester, N-acetyl-3-amino-3-(4-benzenesulfonyloxyphenyl)propanoic acid ethyl ester, N-acetyl-3-amino-3-(4-benzenesulfonyloxyphenyl)propanoic acid isopropyl ester, N-acetyl-3-amino-3-(4-benzenesulfonyloxyphenyl)propanoic acid t-butyl ester, N-acetyl-3-amino-3-(4-benzenesulfonyloxyphenyl)propanoic acid benzyl ester, N-benzyl-3-amino-3-(4-(p-toluenesulfonyloxy)phenyl)propanoic acid methyl ester, N-benzyl-3-amino-3-(4-(p-toluenesulfonyloxy)phenyl)propanoic acid ethyl ester, N-benzyl-3-amino-3-(4-(p-toluenesulfonyloxy)phenyl) propanoic acid isopropyl ester, N-benzyl-3-amino-3-(4-(p-toluenesulfonyloxy)phenyl)propanoic acid t-butyl ester, N-benzyl-3-amino-3-(4-(p-toluenesulfonyloxy)phenyl)propanoic acid benzyl ester, N-benzyl-3-amino-3-(4-methanesulfonyloxyphenyl)propanoic acid methyl ester, N-benzyl-3-amino-3-(4-methanesulfonyloxyphenyl)propanoic acid ethyl ester, N-benzyl-3-amino-3-(4-methanesulfonyloxyphenyl)propanoic acid isopropyl ester, N-benzyl-3-amino-3-(4-methanesulfonyloxyphenyl)propanoic acid t-butyl ester, N-benzyl-3-amino-3-(4-methanesulfonyloxyphenyl)propanoic acid benzyl ester, N-benzyl-3-amino-3-(4-benzenesulfonyloxyphenyl)propanoic acid methyl ester, N-benzyl-3-amino-3-(4-benzenesulfonyloxyphenyl)propanoic acid ethyl ester, N-benzyl-3-amino-3-(4-benzenesulfonyloxyphenyl)propanoic acid isopropyl ester, N-benzyl-3-amino-3-(4-benzenesulfonyloxyphenyl)propanoic acid t-butyl ester, N-benzyl-3-amino-3-(4-benzenesulfonyloxyphenyl)propanoic acid benzyl ester, N-(9-fluorenylmethoxycarbonyl)-3-amino-3-(4-(p-toluenesulfonyloxy)phenyl)propanoic acid methyl ester, N-(9-fluorenylmethoxycarbonyl)-3-amino-3-(4-(p-toluenesulfonyloxy)phenyl)propanoic acid ethyl ester, N-(9-fluorenylmethoxycarbonyl)-3-amino-3-(4-(p-toluenesulfonyloxy)phenyl)propanoic acid isopropyl ester, N-(9-fluorenylmethoxycarbonyl)-3-amino-3-(4-(p-toluenesulfonyloxy)phenyl)propanoic acid t-butyl ester, N-(9-fluorenylmethoxycarbonyl)-3-amino-3-(4-(p-toluenesulfonyloxy)phenyl)propanoic acid benzyl ester, N-(9-fluorenylmethoxycarbonyl)-3-amino-3-(4-methanesulfonyloxyphenyl)propanoic acid methyl ester, N-(9-fluorenylmethoxycarbonyl)-3-amino-3-(4-methanesulfonyloxyphenyl)propanoic acid ethyl ester, N-(9-fluorenylmethoxycarbonyl)-3-amino-3-(4-methanesulfonyloxyphenyl)propanoic acid isopropyl ester, N-(9-fluorenylmethoxycarbonyl)-3-amino-3-(4-methanesulfonyloxyphenyl)propanoic acid t-butyl ester, N-(9-fluorenylmethoxycarbonyl)-3-amino-3-(4-methanesulfonyloxyphenyl)propanoic acid benzyl ester, N-(9-fluorenylmethoxycarbonyl)-3-amino-3-(4-benzenesulfonyloxyphenyl)propanoic acid methyl ester, N-(9-fluorenylmethoxycarbonyl)-3-amino-3-(4-benzenesulfonyloxyphenyl)propanoic acid ethyl ester, N-(9-fluorenylmethoxycarbonyl)-3-amino-3-(4-benzenesulfonyloxyphenyl)propanoic acid isopropyl ester, N-(9-fluorenylmethoxycarbonyl)-3-amino-3-(4-benzenesulfonyloxyphenyl)propanoic acid t-butyl ester, N-(9-fluorenylmethoxycarbonyl)-3-amino-3-(4-benzenesulfonyloxyphenyl)propanoic acid benzyl ester, N-benzyloxycarbonyl-3-amino-3-(4-(p-toluenesulfonyloxy)phenyl)propanoic acid methyl ester, N-benzyloxycarbonyl-3-amino-3-(4-(p-toluenesulfonyloxy)phenyl)propanoic acid ethyl ester, N-benzyloxycarbonyl-3-amino-3-(4-(p-toluenesulfonyloxy)phenyl)propanoic acid isopropyl ester, N-benzyloxycarbonyl-3-amino-3-(4-(p-toluenesulfonyloxy)phenyl)propanoic acid t-butyl ester, N-benzyloxycarbonyl-3-amino-3-(4-(p-toluenesulfonyloxy)phenyl)propanoic acid benzyl ester, N-benzyloxycarbonyl-3-amino-3-(4-methanesulfonyloxyphenyl)propanoic acid methyl ester, N-benzyloxycarbonyl-3-amino-3-(4-methanesulfonyloxyphenyl)propanoic acid ethyl ester, N-benzyloxycarbonyl-3-amino-3-(4-methanesulfonyloxyphenyl)propanoic acid isopropyl ester, N-benzyloxycarbonyl-3-amino-3-(4-methanesulfonyloxyphenyl)propanoic acid t-butyl ester, N-benzyloxycarbonyl-3-amino-3-(4-methanesulfonyloxyphenyl)propanoic acid benzyl ester, N-benzyloxycarbonyl-3-amino-3-(4-benzenesulfonyloxyphenyl)propanoic acid methyl ester, N-benzyloxycarbonyl-3-amino-3-(4-benzenesulfonyloxyphenyl)propanoic acid ethyl ester, N-benzyloxycarbonyl-3-amino-3-(4-benzenesulfonyloxyphenyl)propanoic acid isopropyl ester, N-benzyloxycarbonyl-3-amino-3-(4-benzenesulfonyloxyphenyl)propanoic acid t-butyl ester, N-benzyloxycarbonyl-3-amino-3-(4-benzenesulfonyloxyphenyl)propanoic acid benzyl ester, N-(t-butyloxycarbonyl)-4-amino-3-(4-(p-toluenesulfonyloxy)phenyl)butanoic acid methyl ester, N-(t-butyloxycarbonyl)-4-amino-3-(4-(p-toluenesulfonyloxy)phenyl)butanoic acid ethyl ester, N-(t-butyloxycarbonyl)-4-amino-3-(4-(p-toluenesulfonyloxy)phenyl)butanoic acid isopropyl ester, N-(t-butyloxycarbonyl)-4-amino-3-(4-(p-toluenesulfonyloxy)phenyl)butanoic acid t-butyl ester, N-(t-butyloxycarbonyl)-4-amino-3-(4-(p-toluenesulfonyloxy)phenyl)butanoic acid benzyl ester, N-(t-butyloxycarbonyl)-4-amino-3-(4-methanesulfonyloxyphenyl)butanoic acid methyl ester, N-(t-butyloxycarbonyl)-4-amino-3-(4-methanesulfonyloxyphenyl)butanoic acid ethyl ester, N-(t-butyloxycarbonyl)-4-amino-3-(4-methanesulfonyloxyphenyl)butanoic acid isopropyl ester, N-(t-butyloxycarbonyl)-4-amino-3-(4-methanesulfonyloxyphenyl)butanoic acid t-butyl ester, N-(t-butyloxycarbonyl)-4-amino-3-(4-methanesulfonyloxyphenyl)butanoic acid benzyl ester, N-(t-butyloxycarbonyl)-4-amino-3-(4-benzenesulfonyloxyphenyl)butanoic acid methyl ester, N-(t-butyloxycarbonyl)-4-amino-3-(4-benzenesulfonyloxyphenyl)butanoic acid ethyl ester, N-(t-butyloxycarbonyl)-4-amino-3-(4-benzenesulfonyloxyphenyl)butanoic acid isopropyl ester, N-(t-butyloxycarbonyl)-4-amino-3-(4-benzenesulfonyloxyphenyl)butanoic acid t-butyl ester, N-(t-butyloxycarbonyl)-4-amino-3-(4-benzenesulfonyloxyphenyl)butanoic acid benzyl ester, N-acetyl-4-amino-3-(4-(p-toluenesulfonyloxy)phenyl)butanoic acid methyl ester, N-acetyl-4-amino-3-(4-(p-toluenesulfonyloxy)phenyl)butanoic acid ethyl ester, N-4-amino-3-(4-(p-toluenesulfonyloxy)phenyl)butanoic acid isopropyl ester, N-4-amino-3-(4-(p-toluenesulfonyloxy)phenyl)butanoic acid t-butyl ester, N-acetyl-4-amino-3-(4-(p-toluenesulfonyloxy)phenyl)butanoic acid benzyl ester, N-acetyl-4-amino-3-(4-methanesulfonyloxyphenyl)butanoic acid methyl ester, N-acetyl-4-amino-3-(4-methanesulfonyloxyphenyl)butanoic acid ethyl ester, N-acetyl-4-amino-3-(4-methanesulfonyloxyphenyl)butanoic acid isopropyl ester, N-acetyl-4-amino-3-(4-methanesulfonyloxyphenyl)butanoic acid t-butyl ester, N-acetyl-4-amino-3-(4-methanesulfonyloxyphenyl)butanoic acid benzyl ester, N-acetyl-4-amino-3-(4-benzenesulfonyloxyphenyl)butanoic acid methyl ester, N-acetyl-4-amino-3-(4-benzenesulfonyloxyphenyl)butanoic acid ethyl ester, N-acetyl-4-amino-3-(4-benzenesulfonyloxyphenyl)butanoic acid isopropyl ester, N-acetyl-4-amino-3-(4-benzenesulfonyloxyphenyl)butanoic acid t-butyl ester, N-acetyl-4-amino-3-(4-benzenesulfonyloxyphenyl)butanoic acid benzyl ester, N-benzyl-4-amino-3-(4-(p-toluenesulfonyloxy)phenyl)butanoic acid methyl ester, N-benzyl-4-amino-3-(4-(p-toluenesulfonyloxy)phenyl)butanoic acid ethyl ester, N-benzyl-4-amino-3-(4-(p-toluenesulfonyloxy)phenyl)butanoic acid isopropyl ester, N-benzyl-4-amino-3-(4-(p-toluenesulfonyloxy)phenyl)butanoic acid t-butyl ester, N-benzyl-4-amino-3-(4-(p-toluenesulfonyloxy)phenyl)butanoic acid benzyl ester, N-benzyl-4-amino-3-(4-methanesulfonyloxyphenyl)butanoic acid methyl ester, N-benzyl-4-amino-3-(4-methanesulfonyloxyphenyl)butanoic acid ethyl ester, N-benzyl-4-amino-3-(4-methanesulfonyloxyphenyl)butanoic acid isopropyl ester, N-benzyl-4-amino-3-(4-methanesulfonyloxyphenyl)butanoic acid t-butyl ester, N-benzyl-4-amino-3-(4-methanesulfonyloxyphenyl)butanoic acid benzyl ester, N-benzyl-4-amino-3-(4-benzenesulfonyloxyphenyl)butanoic acid methyl ester, N-benzyl-4-amino-3-(4-benzenesulfonyloxyphenyl)butanoic acid ethyl ester, N-benzyl-4-amino-3-(4-benzenesulfonyloxyphenyl)butanoic acid isopropyl ester, N-benzyl-4-amino-3-(4-benzenesulfonyloxyphenyl)butanoic acid t-butyl ester, N-benzyl-4-amino-3-(4-benzenesulfonyloxyphenyl)butanoic acid benzyl ester, N-(9-fluorenylmethoxycarbonyl)-4-amino-3-(4-(p-toluenesulfonyloxy)phenyl)butanoic acid methyl ester, N-(9-fluorenylmethoxycarbonyl)-4-amino-3-(4-(p-toluenesulfonyloxy)phenyl)butanoic acid ethyl ester, N-(9-fluorenylmethoxycarbonyl)-4-amino-3-(4-(p-toluenesulfonyloxy)phenyl)butanoic acid isopropyl ester, N-(9-fluorenylmethoxycarbonyl)-4-amino-3-(4-(p-toluenesulfonyloxy)phenyl)butanoic acid t-butyl ester, N-(9-fluorenylmethoxycarbonyl)-4-amino-3-(4-(p-toluenesulfonyloxy)phenyl)butanoic acid benzyl ester, N-(9-fluorenylmethoxycarbonyl)-4-amino-3-(4-methanesulfonyloxyphenyl)butanoic acid methyl ester, N-(9-fluorenylmethoxycarbonyl)-4-amino-3-(4-methanesulfonyloxyphenyl)butanoic acid ethyl ester, N-(9-fluorenylmethoxycarbonyl)-4-amino-3-(4-methanesulfonyloxyphenyl)butanoic acid isopropyl ester, N-(9-fluorenylmethoxycarbonyl)-4-amino-3-(4-methanesulfonyloxyphenyl)butanoic acid t-butyl ester, N-(9-fluorenylmethoxycarbonyl)-4-amino-3-(4-methanesulfonyloxyphenyl)butanoic acid benzyl ester, N-(9-fluorenylmethoxycarbonyl)-4-amino-3-(4-benzenesulfonyloxyphenyl)butanoic acid methyl ester, N-(9-fluorenylmethoxycarbonyl)-4-amino-3-(4-benzenesulfonyloxyphenyl)butanoic acid ethyl ester, N-(9-fluorenylmethoxycarbonyl)-4-amino-3-(4-benzenesulfonyloxyphenyl)butanoic acid isopropyl ester, N-(9-fluorenylmethoxycarbonyl)-4-amino-3-(4-benzenesulfonyloxyphenyl)butanoic acid t-butyl ester, N-(9-fluorenylmethoxycarbonyl)-4-amino-3-(4-benzenesulfonyloxyphenyl)butanoic acid benzyl ester, N-benzyloxycarbonyl-4-amino-3-(4-(p-toluenesulfonyloxy)phenyl)butanoic acid methyl ester, N-benzyloxycarbonyl-4-amino-3-(4-(p-toluenesulfonyloxy)phenyl)butanoic acid ethyl ester, N-benzyloxycarbonyl-4-amino-3-(4-(p-toluenesulfonyloxy)phenyl)butanoic acid isopropyl ester, N-benzyloxycarbonyl-4-amino-3-(4-(p-toluenesulfonyloxy)phenyl)butanoic acid t-butyl ester, N-benzyloxycarbonyl-4-amino-3-(4-(p-toluenesulfonyloxy)phenyl)butanoic acid benzyl ester, N-benzyloxycarbonyl-4-amino-3-(4-methanesulfonyloxyphenyl)butanoic acid methyl ester, N-benzyloxycarbonyl-4-amino-3-(4-methanesulfonyloxyphenyl)butanoic acid ethyl ester, N-benzyloxycarbonyl-4-amino-3-(4-methanesulfonyloxyphenyl)butanoic acid isopropyl ester, N-benzyloxycarbonyl-4-amino-3-(4-methanesulfonyloxyphenyl)butanoic acid t-butyl ester, N-benzyloxycarbonyl-4-amino-3-(4-methanesulfonyloxyphenyl)butanoic acid benzyl ester, N-benzyloxycarbonyl-4-amino-3-(4-benzenesulfonyloxyphenyl)butanoic acid methyl ester, N-benzyloxycarbonyl-4-amino-3-(4-benzenesulfonyloxyphenyl)butanoic acid ethyl ester, N-benzyloxycarbonyl-4-amino-3-(4-benzenesulfonyloxyphenyl)butanoic acid isopropyl ester, N-benzyloxycarbonyl-4-amino-3-(4-benzenesulfonyloxyphenyl)butanoic acid t-butyl ester, N-benzyloxycarbonyl-4-amino-3-(4-benzenesulfonyloxyphenyl)butanoic acid benzyl ester, N-(t-butyloxycarbonyl)-4-amino-3-(3-(p-toluenesulfonyloxy)phenyl)butanoic acid methyl ester, N-(t-butyloxycarbonyl)-4-amino-3-(3-(p-toluenesulfonyloxy)phenyl)butanoic acid ethyl ester, N-(t-butyloxycarbonyl)-4-amino-3-(3-(p-toluenesulfonyloxy)phenyl)butanoic acid isopropyl ester, N-(t-butyloxycarbonyl)-4-amino-3-(3-(p-toluenesulfonyloxy)phenyl)butanoic acid t-butyl ester, N-(t-butyloxycarbonyl)-4-amino-3-(3-(p-toluenesulfonyloxy)phenyl)butanoic acid benzyl ester, N-(t-butyloxycarbonyl)-4-amino-3-(3-methanesulfonyloxyphenyl)butanoic acid methyl ester, N-(t-butyloxycarbonyl)-4-amino-3-(3-methanesulfonyloxyphenyl)butanoic acid ethyl ester, N-(t-butyloxycarbonyl)-4-amino-3-(3-methanesulfonyloxyphenyl)butanoic acid isopropyl ester, N-(t-butyloxycarbonyl)-4-amino-3-(3-methanesulfonyloxyphenyl)butanoic acid t-butyl ester, N-(t-butyloxycarbonyl)-4-amino-3-(3-methanesulfonyloxyphenyl)butanoic acid benzyl ester, N-(t-butyloxycarbonyl)-4-amino-3-(3-benzenesulfonyloxyphenyl)butanoic acid methyl ester, N-(t-butyloxycarbonyl)-4-amino-3-(3-benzenesulfonyloxyphenyl)butanoic acid ethyl ester, N-(t-butyloxycarbonyl)-4-amino-3-(3-benzenesulfonyloxyphenyl)butanoic acid isopropyl ester, N-(t-butyloxycarbonyl)-4-amino-3-(3-benzenesulfonyloxyphenyl)butanoic acid t-butyl ester, N-(t-butyloxycarbonyl)-4-amino-3-(3-benzenesulfonyloxyphenyl)butanoic acid benzyl ester, N-acetyl-4-amino-3-(3-(p-toluenesulfonyloxy)phenyl)butanoic acid methyl ester, N-acetyl-4-amino-3-(3-(p-toluenesulfonyloxy)phenyl)butanoic acid ethyl ester, N-4-amino-3-(3-(p-toluenesulfonyloxy)phenyl)butanoic acid isopropyl ester, N-4-amino-3-(3-(p-toluenesulfonyloxy)phenyl)butanoic acid t-butyl ester, N-acetyl-4-amino-3-(3-(p-toluenesulfonyloxy)phenyl)butanoic acid benzyl ester, N-acetyl-4-amino-3-(3-methanesulfonyloxyphenyl)butanoic acid methyl ester, N-acetyl-4-amino-3-(3-methanesulfonyloxyphenyl)butanoic acid ethyl ester, N-acetyl-4-amino-3-(3-methanesulfonyloxyphenyl)butanoic acid isopropyl ester, N-acetyl-4-amino-3-(3-methanesulfonyloxyphenyl)butanoic acid t-butyl ester, N-acetyl-4-amino-3-(3-methanesulfonyloxyphenyl)butanoic acid benzyl ester, N-acetyl-4-amino-3-(3-benzenesulfonyloxyphenyl)butanoic acid methyl ester, N-acetyl-4-amino-3-(3-benzenesulfonyloxyphenyl)butanoic acid ethyl ester, N-acetyl-4-amino-3-(3-benzenesulfonyloxyphenyl)butanoic acid isopropyl ester, N-acetyl-4-amino-3-(3-benzenesulfonyloxyphenyl)butanoic acid t-butyl ester, N-acetyl-4-amino-3-(3-benzenesulfonyloxyphenyl)butanoic acid benzyl ester, N-benzyl-4-amino-3-(3-(p-toluenesulfonyloxy)phenyl)butanoic acid methyl ester, N-benzyl-4-amino-3-(3-(p-toluenesulfonyloxy)phenyl)butanoic acid ethyl ester, N-benzyl-4-amino-3-(3-(p-toluenesulfonyloxy)phenyl)butanoic acid isopropyl ester, N-benzyl-4-amino-3-(3-(p-toluenesulfonyloxy)phenyl)butanoic acid t-butyl ester, N-benzyl-4-amino-3-(3-(p-toluenesulfonyloxy)phenyl)butanoic acid benzyl ester, N-benzyl-4-amino-3-(3-methanesulfonyloxyphenyl)butanoic acid methyl ester, N-benzyl-4-amino-3-(3-methanesulfonyloxyphenyl)butanoic acid ethyl ester, N-benzyl-4-amino-3-(3-methanesulfonyloxyphenyl)butanoic acid isopropyl ester, N-benzyl-4-amino-3-(3-methanesulfonyloxyphenyl)butanoic acid t-butyl ester, N-benzyl-4-amino-3-(3-methanesulfonyloxyphenyl)butanoic acid benzyl ester, N-benzyl-4-amino-3-(3-benzenesulfonyloxyphenyl)butanoic acid methyl ester, N-benzyl-4-amino-3-(3-benzenesulfonyloxyphenyl)butanoic acid ethyl ester, N-benzyl-4-amino-3-(3-benzenesulfonyloxyphenyl)butanoic acid isopropyl ester, N-benzyl-4-amino-3-(3-benzenesulfonyloxyphenyl)butanoic acid t-butyl ester, N-benzyl-4-amino-3-(3-benzenesulfonyloxyphenyl)butanoic acid benzyl ester, N-(9-fluorenylmethoxycarbonyl)-4-amino-3-(3-(p-toluenesulfonyloxy)phenyl)butanoic acid methyl ester, N-(9-fluorenylmethoxycarbonyl)-4-amino-3-(3-(p-toluenesulfonyloxy)phenyl)butanoic acid ethyl ester, N-(9-fluorenylmethoxycarbonyl)-4-amino-3-(3-(p-toluenesulfonyloxy)phenyl)butanoic acid isopropyl ester, N-(9-fluorenylmethoxycarbonyl)-4-amino-3-(3-(p-toluenesulfonyloxy)phenyl)butanoic acid t-butyl ester, N-(9-fluorenylmethoxycarbonyl)-4-amino-3-(3-(p-toluenesulfonyloxy)phenyl)butanoic acid benzyl ester, N-(9-fluorenylmethoxycarbonyl)-4-amino-3-(3-methanesulfonyloxyphenyl)butanoic acid methyl ester, N-(9-fluorenylmethoxycarbonyl)-4-amino-3-(3-methanesulfonyloxyphenyl)butanoic acid ethyl ester, N-(9-fluorenylmethoxycarbonyl)-4-amino-3-(3-methanesulfonyloxyphenyl)butanoic acid isopropyl ester, N-(9-fluorenylmethoxycarbonyl)-4-amino-3-(3-methanesulfonyloxyphenyl)butanoic acid t-butyl ester, N-(9-fluorenylmethoxycarbonyl)-4-amino-3-(3-methanesulfonyloxyphenyl)butanoic acid benzyl ester, N-(9-fluorenylmethoxycarbonyl)-4-amino-3-(3-benzenesulfonyloxyphenyl)butanoic acid methyl ester, N-(9-fluorenylmethoxycarbonyl)-4-amino-3-(3-benzenesulfonyloxyphenyl)butanoic acid ethyl ester, N-(9-fluorenylmethoxycarbonyl)-4-amino-3-(3-benzenesulfonyloxyphenyl)butanoic acid isopropyl ester, N-(9-fluorenylmethoxycarbonyl)-4-amino-3-(3-benzenesulfonyloxyphenyl)butanoic acid t-butyl ester, N-(9-fluorenylmethoxycarbonyl)-4-amino-3-(3-benzenesulfonyloxyphenyl)butanoic acid benzyl ester, N-benzyloxycarbonyl-4-amino-3-(3-(p-toluenesulfonyloxy)phenyl)butanoic acid methyl ester, N-benzyloxycarbonyl-4-amino-3-(3-(p-toluenesulfonyloxy)phenyl)butanoic acid ethyl ester, N-benzyloxycarbonyl-4-amino-3-(3-(p-toluenesulfonyloxy)phenyl)butanoic acid isopropyl ester, N-benzyloxycarbonyl-4-amino-3-(3-(p-toluenesulfonyloxy)phenyl)butanoic acid t-butyl ester, N-benzyloxycarbonyl-4-amino-3-(3-(p-toluenesulfonyloxy)phenyl)butanoic acid benzyl ester, N-benzyloxycarbonyl-4-amino-3-(3-methanesulfonyloxyphenyl)butanoic acid methyl ester, N-benzyloxycarbonyl-4-amino-3-(3-methanesulfonyloxyphenyl)butanoic acid ethyl ester, N-benzyloxycarbonyl-4-amino-3-(3-methanesulfonyloxyphenyl)butanoic acid isopropyl ester, N-benzyloxycarbonyl-4-amino-3-(3-methanesulfonyloxyphenyl)butanoic acid t-butyl ester, N-benzyloxycarbonyl-4-amino-3-(3-methanesulfonyloxyphenyl)butanoic acid benzyl ester, N-benzyloxycarbonyl-4-amino-3-(3-benzenesulfonyloxyphenyl)butanoic acid methyl ester, N-benzyloxycarbonyl-4-amino-3-(3-benzenesulfonyloxyphenyl)butanoic acid ethyl ester, N-benzyloxycarbonyl-4-amino-3-(3-benzenesulfonyloxyphenyl)butanoic acid isopropyl ester, N-benzyloxycarbonyl-4-amino-3-(3-benzenesulfonyloxyphenyl)butanoic acid t-butyl ester, N-benzyloxycarbonyl-4-amino-3-(3-benzenesulfonyloxyphenyl)butanoic acid benzyl ester, N-(t-butyloxycarbonyl)-3-amino-2-(4-(p-toluenesulfonyloxy)phenyl)propanoic acid methyl ester, N-(t-butyloxycarbonyl)-3-amino-2-(4-(p-toluenesulfonyloxy)phenyl)propanoic acid ethyl ester, N-(t-butyloxycarbonyl)-3-amino-2-(4-(p-toluenesulfonyloxy)phenyl)propanoic acid isopropyl ester, N-(t-butyloxycarbonyl)-3-amino-2-(4-(p-toluenesulfonyloxy)phenyl)propanoic acid t-butyl ester, N-(t-butyloxycarbonyl)-3-amino-2-(4-(p-toluenesulfonyloxy)phenyl)propanoic acid benzyl ester, N-(t-butyloxycarbonyl)-3-amino-2-(4-methanesulfonyloxyphenyl)propanoic acid methyl ester, N-(t-butyloxycarbonyl)-3-amino-2-(4-methanesulfonyloxyphenyl)propanoic acid ethyl ester, N-(t-butyloxycarbonyl)-3-amino-2-(4-methanesulfonyloxyphenyl)propanoic acid isopropyl ester, N-(t-butyloxycarbonyl)-3-amino-2-(4-methanesulfonyloxyphenyl)propanoic acid t-butyl ester, N-(t-butyloxycarbonyl)-3-amino-2-(4-methanesulfonyloxyphenyl)propanoic acid benzyl ester, N-(t-butyloxycarbonyl)-3-amino-2-(4-benzenesulfonyloxyphenyl)propanoic acid methyl ester, N-(t-butyloxycarbonyl)-3-amino-2-(4-benzenesulfonyloxyphenyl)propanoic acid ethyl ester, N-(t-butyloxycarbonyl)-3-amino-2-(4-benzenesulfonyloxyphenyl)propanoic acid isopropyl ester, N-(t-butyloxycarbonyl)-3-amino-2-(4-benzenesulfonyloxyphenyl)propanoic acid t-butyl ester, N-(t-butyloxycarbonyl)-3-amino-2-(4-benzenesulfonyloxyphenyl)propanoic acid benzyl ester, N-acetyl-3-amino-2-(4-(p-toluenesulfonyloxy)phenyl)propanoic acid methyl ester, N-acetyl-3-amino-2-(4-(p-toluenesulfonyloxy)phenyl)propanoic acid ethyl ester, N-3-amino-2-(4-(p-toluenesulfonyloxy)phenyl)propanoic acid isopropyl ester, N-3-amino-2-(4-(p-toluenesulfonyloxy)phenyl)propanoic acid t-butyl ester, N-acetyl-3-amino-2-(4-(p-toluenesulfonyloxy)phenyl)propanoic acid benzyl ester, N-acetyl-3-amino-2-(4-methanesulfonyloxyphenyl)propanoic acid methyl ester, N-acetyl-3-amino-2-(4-methanesulfonyloxyphenyl)propanoic acid ethyl ester, N-acetyl-3-amino-2-(4-methanesulfonyloxyphenyl)propanoic acid isopropyl ester, N-acetyl-3-amino-2-(4-methanesulfonyloxyphenyl)propanoic acid t-butyl ester, N-acetyl-3-amino-2-(4-methanesulfonyloxyphenyl)propanoic acid benzyl ester, N-acetyl-3-amino-2-(4-benzenesulfonyloxyphenyl)propanoic acid methyl ester, N-acetyl-3-amino-2-(4-benzenesulfonyloxyphenyl)propanoic acid ethyl ester, N-acetyl-3-amino-2-(4-benzenesulfonyloxyphenyl)propanoic acid isopropyl ester, N-acetyl-3-amino-2-(4-benzenesulfonyloxyphenyl)propanoic acid t-butyl ester, N-acetyl-3-amino-2-(4-benzenesulfonyloxyphenyl)propanoic acid benzyl ester, N-benzyl-3-amino-2-(4-(p-toluenesulfonyloxy)phenyl)propanoic acid methyl ester, N-benzyl-3-amino-2-(4-(p-toluenesulfonyloxy)phenyl)propanoic acid ethyl ester, N-benzyl-3-amino-2-(4-(p-toluenesulfonyloxy)phenyl)propanoic acid isopropyl ester, N-benzyl-3-amino-2-(4-(p-toluenesulfonyloxy)phenyl)propanoic acid t-butyl ester, N-benzyl-3-amino-2-(4-(p-toluenesulfonyloxy)phenyl)propanoic acid benzyl ester, N-benzyl-3-amino-2-(4-methanesulfonyloxyphenyl)propanoic acid methyl ester, N-benzyl-3-amino-2-(4-methanesulfonyloxyphenyl)propanoic acid ethyl ester, N-benzyl-3-amino-2-(4-methanesulfonyloxyphenyl)propanoic acid isopropyl ester, N-benzyl-3-amino-2-(4-methanesulfonyloxyphenyl)propanoic acid t-butyl ester, N-benzyl-3-amino-2-(4-methanesulfonyloxyphenyl)propanoic acid benzyl ester, N-benzyl-3-amino-2-(4-benzenesulfonyloxyphenyl)propanoic acid methyl ester, N-benzyl-3-amino-2-(4-benzenesulfonyloxyphenyl)propanoic acid ethyl ester, N-benzyl-3-amino-2-(4-benzenesulfonyloxyphenyl)propanoic acid isopropyl ester, N-benzyl-3-amino-2-(4-benzenesulfonyloxyphenyl)propanoic acid t-butyl ester, N-benzyl-3-amino-2-(4-benzenesulfonyloxyphenyl)propanoic acid benzyl ester, N-(9-fluorenylmethoxycarbonyl)-3-amino-2-(4-(p-toluenesulfonyloxy)phenyl)propanoic acid methyl ester, N-(9-fluorenylmethoxycarbonyl)-3-amino-2-(4-(p-toluenesulfonyloxy)phenyl)propanoic acid ethyl ester, N-(9-fluorenylmethoxycarbonyl)-3-amino-2-(4-(p-toluenesulfonyloxy)phenyl)propanoic acid isopropyl ester, N-(9-fluorenylmethoxycarbonyl)-3-amino-2-(4-(p-toluenesulfonyloxy)phenyl)propanoic acid t-butyl ester, N-(9-fluorenylmethoxycarbonyl)-3-amino-2-(4-(p-toluenesulfonyloxy)phenyl)propanoic acid benzyl ester, N-(9-fluorenylmethoxycarbonyl)-3-amino-2-(4-methanesulfonyloxyphenyl)propanoic acid methyl ester, N-(9-fluorenylmethoxycarbonyl)-3-amino-2-(4-methanesulfonyloxyphenyl)propanoic acid ethyl ester, N-(9-fluorenylmethoxycarbonyl)-3-amino-2-(4-methanesulfonyloxyphenyl)propanoic acid isopropyl ester, N-(9-fluorenylmethoxycarbonyl)-3-amino-2-(4-methanesulfonyloxyphenyl)propanoic acid t-butyl ester, N-(9-fluorenylmethoxycarbonyl)-3-amino-2-(4-methanesulfonyloxyphenyl)propanoic acid benzyl ester, N-(9-fluorenylmethoxycarbonyl)-3-amino-2-(4-benzenesulfonyloxyphenyl)propanoic acid methyl ester, N-(9-fluorenylmethoxycarbonyl)-3-amino-2-(4-benzenesulfonyloxyphenyl)propanoic acid ethyl ester, N-(9-fluorenylmethoxycarbonyl)-3-amino-2-(4-benzenesulfonyloxyphenyl)propanoic acid isopropyl ester, N-(9-fluorenylmethoxycarbonyl)-3-amino-2-(4-benzenesulfonyloxyphenyl)propanoic acid t-butyl ester, N-(9-fluorenylmethoxycarbonyl)-3-amino-2-(4-benzenesulfonyloxyphenyl)propanoic acid benzyl ester, N-benzyloxycarbonyl-3-amino-2-(4-(p-toluenesulfonyloxy)phenyl)propanoic acid methyl ester, N-benzyloxycarbonyl-3-amino-2-(4-(p-toluenesulfonyloxy)phenyl)propanoic acid ethyl ester, N-benzyloxycarbonyl-3-amino-2-(4-(p-toluenesulfonyloxy)phenyl)propanoic acid isopropyl ester, N-benzyloxycarbonyl-3-amino-2-(4-(p-toluenesulfonyloxy)phenyl)propanoic acid t-butyl ester, N-benzyloxycarbonyl-3-amino-2-(4-(p-toluenesulfonyloxy)phenyl)propanoic acid benzyl ester, N-benzyloxycarbonyl-3-amino-2-(4-methanesulfonyloxyphenyl)propanoic acid methyl ester, N-benzyloxycarbonyl-3-amino-2-(4-methanesulfonyloxyphenyl)propanoic acid ethyl ester, N-benzyloxycarbonyl-3-amino-2-(4-methanesulfonyloxyphenyl)propanoic acid isopropyl ester, N-benzyloxycarbonyl-3-amino-2-(4-methanesulfonyloxyphenyl)propanoic acid t-butyl ester, N-benzyloxycarbonyl-3-amino-2-(4-methanesulfonyloxyphenyl)propanoic acid benzyl ester, N-benzyloxycarbonyl-3-amino-2-(4-benzenesulfonyloxyphenyl)propanoic acid methyl ester, N-benzyloxycarbonyl-3-amino-2-(4-benzenesulfonyloxyphenyl)propanoic acid ethyl ester, N-benzyloxycarbonyl-3-amino-2-(4-benzenesulfonyloxyphenyl)propanoic acid isopropyl ester, N-benzyloxycarbonyl-3-amino-2-(4-benzenesulfonyloxyphenyl)propanoic acid t-butyl ester, N-benzyloxycarbonyl-3-amino-2-(4-benzenesulfonyloxyphenyl)propanoic acid benzyl ester, N-(t-butyloxycarbonyl)-3-amino-2-(3-(p-toluenesulfonyloxy)phenyl)propanoic acid methyl ester, N-(t-butyloxycarbonyl)-3-amino-2-(3-(p-toluenesulfonyloxy)phenyl)propanoic acid ethyl ester, N-(t-butyloxycarbonyl)-3-amino-2-(3-(p-toluenesulfonyloxy)phenyl)propanoic acid isopropyl ester, N-(t-butyloxycarbonyl)-3-amino-2-(3-(p-toluenesulfonyloxy)phenyl)propanoic acid t-butyl ester, N-(t-butyloxycarbonyl)-3-amino-2-(3-(p-toluenesulfonyloxy)phenyl)propanoic acid benzyl ester, N-(t-butyloxycarbonyl)-3-amino-2-(3-methanesulfonyloxyphenyl)propanoic acid methyl ester, N-(t-butyloxycarbonyl)-3-amino-2-(3-methanesulfonyloxyphenyl)propanoic acid ethyl ester, N-(t-butyloxycarbonyl)-3-amino-2-(3-methanesulfonyloxyphenyl)propanoic acid isopropyl ester, N-(t-butyloxycarbonyl)-3-amino-2-(3-methanesulfonyloxyphenyl)propanoic acid t-butyl ester, N-(t-butyloxycarbonyl)-3-amino-2-(3-methanesulfonyloxyphenyl)propanoic acid benzyl ester, N-(t-butyloxycarbonyl)-3-amino-2-(3-benzenesulfonyloxyphenyl)propanoic acid methyl ester, N-(t-butyloxycarbonyl)-3-amino-2-(3-benzenesulfonyloxyphenyl)propanoic acid ethyl ester, N-(t-butyloxycarbonyl)-3-amino-2-(3-benzenesulfonyloxyphenyl)propanoic acid isopropyl ester, N-(t-butyloxycarbonyl)-3-amino-2-(3-benzenesulfonyloxyphenyl)propanoic acid t-butyl ester, N-(t-butyloxycarbonyl)-3-amino-2-(3-benzenesulfonyloxyphenyl)propanoic acid benzyl ester, N-acetyl-3-amino-2-(3-(p-toluenesulfonyloxy)phenyl)propanoic acid methyl ester, N-acetyl-3-amino-2-(3-(p-toluenesulfonyloxy)phenyl)propanoic acid ethyl ester, N-3-amino-2-(3-(p-toluenesulfonyloxy)phenyl)propanoic acid isopropyl ester, N-3-amino-2-(3-(p-toluenesulfonyloxy)phenyl)propanoic acid t-butyl ester, N-acetyl-3-amino-2-(3-(p-toluenesulfonyloxy)phenyl)propanoic acid benzyl ester, N-acetyl-3-amino-2-(3-methanesulfonyloxyphenyl)propanoic acid methyl ester, N-acetyl-3-amino-2-(3-methanesulfonyloxyphenyl)propanoic acid ethyl ester, N-acetyl-3-amino-2-(3-methanesulfonyloxyphenyl)propanoic acid isopropyl ester, N-acetyl-3-amino-2-(3-methanesulfonyloxyphenyl)propanoic acid t-butyl ester, N-acetyl-3-amino-2-(3-methanesulfonyloxyphenyl)propanoic acid benzyl ester, N-acetyl-3-amino-2-(3-benzenesulfonyloxyphenyl)propanoic acid methyl ester, N-acetyl-3-amino-2-(3-benzenesulfonyloxyphenyl)propanoic acid ethyl ester, N-acetyl-3-amino-2-(3-benzenesulfonyloxyphenyl)propanoic acid isopropyl ester, N-acetyl-3-amino-2-(3-benzenesulfonyloxyphenyl)propanoic acid t-butyl ester, N-acetyl-3-amino-2-(3-benzenesulfonyloxyphenyl)propanoic acid benzyl ester, N-benzyl-3-amino-2-(3-(p-toluenesulfonyloxy)phenyl)propanoic acid methyl ester, N-benzyl-3-amino-2-(3-(p-toluenesulfonyloxy)phenyl)propanoic acid ethyl ester, N-benzyl-3-amino-2-(3-(p-toluenesulfonyloxy)phenyl)propanoic acid isopropyl ester, N-benzyl-3-amino-2-(3-(p-toluenesulfonyloxy)phenyl)propanoic acid t-butyl ester, N-benzyl-3-amino-2-(3-(p-toluenesulfonyloxy)phenyl)propanoic acid benzyl ester, N-benzyl-3-amino-2-(3-methanesulfonyloxyphenyl)propanoic acid methyl ester, N-benzyl-3-amino-2-(3-methanesulfonyloxyphenyl)propanoic acid ethyl ester, N-benzyl-3-amino-2-(3-methanesulfonyloxyphenyl)propanoic acid isopropyl ester, N-benzyl-3-amino-2-(3-methanesulfonyloxyphenyl)propanoic acid t-butyl ester, N-benzyl-3-amino-2-(3-methanesulfonyloxyphenyl)propanoic acid benzyl ester, N-benzyl-3-amino-2-(3-benzenesulfonyloxyphenyl)propanoic acid methyl ester, N-benzyl-3-amino-2-(3-benzenesulfonyloxyphenyl)propanoic acid ethyl ester, N-benzyl-3-amino-2-(3-benzenesulfonyloxyphenyl)propanoic acid isopropyl ester, N-benzyl-3-amino-2-(3-benzenesulfonyloxyphenyl)propanoic acid t-butyl ester, N-benzyl-3-amino-2-(3-benzenesulfonyloxyphenyl)propanoic acid benzyl ester, N-(9-fluorenylmethoxycarbonyl)-3-amino-2-(3-(p-toluenesulfonyloxy)phenyl)propanoic acid methyl ester, N-(9-fluorenylmethoxycarbonyl)-3-amino-2-(3-(p-toluenesulfonyloxy)phenyl)propanoic acid ethyl ester, N-(9-fluorenylmethoxycarbonyl)-3-amino-2-(3-(p-toluenesulfonyloxy)phenyl)propanoic acid isopropyl ester, N-(9-fluorenylmethoxycarbonyl)-3-amino-2-(3-(p-toluenesulfonyloxy)phenyl)propanoic acid t-butyl ester, N-(9-fluorenylmethoxycarbonyl)-3-amino-2-(3-(p-toluenesulfonyloxy)phenyl)propanoic acid benzyl ester, N-(9-fluorenylmethoxycarbonyl)-3-amino-2-(3-methanesulfonyloxyphenyl)propanoic acid methyl ester, N-(9-fluorenylmethoxycarbonyl)-3-amino-2-(3-methanesulfonyloxyphenyl)propanoic acid ethyl ester, N-(9-fluorenylmethoxycarbonyl)-3-amino-2-(3-methanesulfonyloxyphenyl)propanoic acid isopropyl ester, N-(9-fluorenylmethoxycarbonyl)-3-amino-2-(3-methanesulfonyloxyphenyl)propanoic acid t-butyl ester, N-(9-fluorenylmethoxycarbonyl)-3-amino-2-(3-methanesulfonyloxyphenyl)propanoic acid benzyl ester, N-(9-fluorenylmethoxycarbonyl)-3-amino-2-(3-benzenesulfonyloxyphenyl)propanoic acid methyl ester, N-(9-fluorenylmethoxycarbonyl)-3-amino-2-(3-benzenesulfonyloxyphenyl)propanoic acid ethyl ester, N-(9-fluorenylmethoxycarbonyl)-3-amino-2-(3-benzenesulfonyloxyphenyl)propanoic acid isopropyl ester, N-(9-fluorenylmethoxycarbonyl)-3-amino-2-(3-benzenesulfonyloxyphenyl)propanoic acid t-butyl ester, N-(9-fluorenylmethoxycarbonyl)-3-amino-2-(3-benzenesulfonyloxyphenyl)propanoic acid benzyl ester, N-benzyloxycarbonyl-3-amino-2-(3-(p-toluenesulfonyloxy)phenyl)propanoic acid methyl ester, N-benzyloxycarbonyl-3-amino-2-(3-(p-toluenesulfonyloxy)phenyl)propanoic acid ethyl ester, N-benzyloxycarbonyl-3-amino-2-(3-(p-toluenesulfonyloxy)phenyl)propanoic acid isopropyl ester,
N-benzyloxycarbonyl-3-amino-2-(3-(p-toluenesulfonyloxy)phenyl)propanoic acid t-butyl ester, N-benzyloxycarbonyl-3-amino-2-(3-(p-toluenesulfonyloxy)phenyl)propanoic acid benzyl ester, N-benzyloxycarbonyl-3-amino-2-(3-methanesulfonyloxyphenyl)propanoic acid methyl ester, N-benzyloxycarbonyl-3-amino-2-(3-methanesulfonyloxyphenyl)propanoic acid ethyl ester, N-benzyloxycarbonyl-3-amino-2-(3-methanesulfonyloxyphenyl)propanoic acid isopropyl ester, N-benzyloxycarbonyl-3-amino-2-(3-methanesulfonyloxyphenyl)propanoic acid t-butyl ester, N-benzyloxycarbonyl-3-amino-2-(3-methanesulfonyloxyphenyl)propanoic acid benzyl ester, N-benzyloxycarbonyl-3-amino-2-(3-benzenesulfonyloxyphenyl)propanoic acid methyl ester, N-benzyloxycarbonyl-3-amino-2-(3-benzenesulfonyloxyphenyl)propanoic acid ethyl ester, N-benzyloxycarbonyl-3-amino-2-(3-benzenesulfonyloxyphenyl)propanoic acid isopropyl ester, N-benzyloxycarbonyl-3-amino-2-(3-benzenesulfonyloxyphenyl)propanoic acid t-butyl ester, N-benzyloxycarbonyl-3-amino-2-(3-benzenesulfonyloxyphenyl)propanoic acid benzyl ester,
N-(t-butyloxycarbonyl)-3-amino-4-(4-(p-toluenesulfonyloxy)phenyl)butanoic acid methyl ester, N-(t-butyloxycarbonyl)-3-amino-4-(4-(p-toluenesulfonyloxy)phenyl)butanoic acid ethyl ester, N-(t-butyloxycarbonyl)-3-amino-4-(4-(p-toluenesulfonyloxy)phenyl)butanoic acid isopropyl ester, N-(t-butyloxycarbonyl)-3-amino-4-(4-(p-toluenesulfonyloxy)phenyl)butanoic acid t-butyl ester, N-(t-butyloxycarbonyl)-3-amino-4-(4-(p-toluenesulfonyloxy)phenyl)butanoic acid benzyl ester, N-(t-butyloxycarbonyl)-3-amino-4-(4-methanesulfonyloxyphenyl)butanoic acid methyl ester, N-(t-butyloxycarbonyl)-3-amino-4-(4-methanesulfonyloxyphenyl)butanoic acid ethyl ester, N-(t-butyloxycarbonyl)-3-amino-4-(4-methanesulfonyloxyphenyl)butanoic acid isopropyl ester, N-(t-butyloxycarbonyl)-3-amino-4-(4-methanesulfonyloxyphenyl)butanoic acid t-butyl ester, N-(t-butyloxycarbonyl)-3-amino-4-(4-methanesulfonyloxyphenyl)butanoic acid benzyl ester, N-(t-butyloxycarbonyl)-3-amino-4-(4-benzenesulfonyloxyphenyl)butanoic acid methyl ester, N-(t-butyloxycarbonyl)-3-amino-4-(4-benzenesulfonyloxyphenyl)butanoic acid ethyl ester, N-(t-butyloxycarbonyl)-3-amino-4-(4-benzenesulfonyloxyphenyl)butanoic acid isopropyl ester, N-(t-butyloxycarbonyl)-3-amino-4-(4-benzenesulfonyloxyphenyl)butanoic acid t-butyl ester, N-(t-butyloxycarbonyl)-3-amino-4-(4-benzenesulfonyloxyphenyl)butanoic acid benzyl ester,
N-acetyl-3-amino-4-(4-(p-toluenesulfonyloxy)phenyl)butanoic acid methyl ester, N-acetyl-3-amino-4-(4-(p-toluenesulfonyloxy)phenyl)butanoic acid ethyl ester, N-3-amino-4-(4-(p-toluenesulfonyloxy)phenyl)butanoic acid isopropyl ester, N-3-amino-4-(4-(p-toluenesulfonyloxy)phenyl)butanoic acid t-butyl ester, N-acetyl-3-amino-4-(4-(p-toluenesulfonyloxy)phenyl)butanoic acid benzyl ester, N-acetyl-3-amino-4-(4-methanesulfonyloxyphenyl)butanoic acid methyl ester, N-acetyl-3-amino-4-(4-methanesulfonyloxyphenyl)butanoic acid ethyl ester, N-acetyl-3-amino-4-(4-methanesulfonyloxyphenyl)butanoic acid isopropyl ester, N-acetyl-3-amino-4-(4-methanesulfonyloxyphenyl)butanoic acid t-butyl ester, N-acetyl-3-amino-4-(4-methanesulfonyloxyphenyl)butanoic acid benzyl ester, N-acetyl-3-amino-4-(4-benzenesulfonyloxyphenyl)butanoic acid methyl ester, N-acetyl-3-amino-4-(4-benzenesulfonyloxyphenyl)butanoic acid ethyl ester, N-acetyl-3-amino-4-(4-benzenesulfonyloxyphenyl)butanoic acid isopropyl ester, N-acetyl-3-amino-4-(4-benzenesulfonyloxyphenyl)butanoic acid t-butyl ester, N-acetyl-3-amino-4-(4-benzenesulfonyloxyphenyl)butanoic acid benzyl ester,
N-benzyl-3-amino-4-(4-(p-toluenesulfonyloxy)phenyl)butanoic acid methyl ester, N-benzyl-3-amino-4-(4-(p-toluenesulfonyloxy)phenyl)butanoic acid ethyl ester, N-benzyl-3-amino-4-(4-(p-toluenesulfonyloxy)phenyl)butanoic acid isopropyl ester, N-benzyl-3-amino-4-(4-(p-toluenesulfonyloxy)phenyl)butanoic acid t-butyl ester, N-benzyl-3-amino-4-(4-(p-toluenesulfonyloxy)phenyl)butanoic acid benzyl ester, N-benzyl-3-amino-4-(4-methanesulfonyloxyphenyl)butanoic acid methyl ester, N-benzyl-3-amino-4-(4-methanesulfonyloxyphenyl)butanoic acid ethyl ester, N-benzyl-3-amino-4-(4-methanesulfonyloxyphenyl)butanoic acid isopropyl ester, N-benzyl-3-amino-4-(4-methanesulfonyloxyphenyl)butanoic acid t-butyl ester, N-benzyl-3-amino-4-(4-methanesulfonyloxyphenyl)butanoic acid benzyl ester, N-benzyl-3-amino-4-(4-benzenesulfonyloxyphenyl)butanoic acid methyl ester, N-benzyl-3-amino-4-(4-benzenesulfonyloxyphenyl)butanoic acid ethyl ester, N-benzyl-3-amino-4-(4-benzenesulfonyloxyphenyl)butanoic acid isopropyl ester, N-benzyl-3-amino-4-(4-benzenesulfonyloxyphenyl)butanoic acid t-butyl ester, N-benzyl-3-amino-4-(4-benzenesulfonyloxyphenyl)butanoic acid benzyl ester,
N-(9-fluorenylmethoxycarbonyl)-3-amino-4-(4-(p-toluenesulfonyloxy)phenyl)butanoic acid methyl ester, N-(9-fluorenylmethoxycarbonyl)-3-amino-4-(4-(p-toluenesulfonyloxy)phenyl)butanoic acid ethyl ester, N-(9-fluorenylmethoxycarbonyl)-3-amino-4-(4-(p-toluenesulfonyloxy)phenyl)butanoic acid isopropyl ester, N-(9-fluorenylmethoxycarbonyl)-3-amino-4-(4-(p-toluenesulfonyloxy)phenyl)butanoic acid t-butyl ester, N-(9-fluorenylmethoxycarbonyl)-3-amino-4-(4-(p-toluenesulfonyloxy)phenyl)butanoic acid benzyl ester, N-(9-fluorenylmethoxycarbonyl)-3-amino-4-(4-methanesulfonyloxyphenyl)butanoic acid methyl ester, N-(9-fluorenylmethoxycarbonyl)-3-amino-4-(4-methanesulfonyloxyphenyl)butanoic acid ethyl ester, N-(9-fluorenylmethoxycarbonyl)-3-amino-4-(4-methanesulfonyloxyphenyl)butanoic acid isopropyl ester, N-(9-fluorenylmethoxycarbonyl)-3-amino-4-(4-methanesulfonyloxyphenyl)butanoic acid t-butyl ester, N-(9-fluorenylmethoxycarbonyl)-3-amino-4-(4-methanesulfonyloxyphenyl)butanoic acid benzyl ester, N-(9-fluorenylmethoxycarbonyl)-3-amino-4-(4-benzenesulfonyloxyphenyl)butanoic acid methyl ester, N-(9-fluorenylmethoxycarbonyl)-3-amino-4-(4-benzenesulfonyloxyphenyl)butanoic acid ethyl ester, N-(9-fluorenylmethoxycarbonyl)-3-amino-4-(4-benzenesulfonyloxyphenyl)butanoic acid isopropyl ester, N-(9-fluorenylmethoxycarbonyl)-3-amino-4-(4-benzenesulfonyloxyphenyl)butanoic acid t-butyl ester, N-(9-fluorenylmethoxycarbonyl)-3-amino-4-(4-benzenesulfonyloxyphenyl)butanoic acid benzyl ester,
N-benzyloxycarbonyl-3-amino-4-(4-(p-toluenesulfonyloxy)phenyl)butanoic acid methyl ester, N-benzyloxycarbonyl-3-amino-4-(4-(p-toluenesulfonyloxy)phenyl)butanoic acid ethyl ester, N-benzyloxycarbonyl-3-amino-4-(4-(p-toluenesulfonyloxy)phenyl)butanoic acid isopropyl ester, N-benzyloxycarbonyl-3-amino-4-(4-(p-toluenesulfonyloxy)phenyl)butanoic acid t-butyl ester, N-benzyloxycarbonyl-3-amino-4-(4-(p-toluenesulfonyloxy)phenyl)butanoic acid benzyl ester, N-benzyloxycarbonyl-3-amino-4-(4-methanesulfonyloxyphenyl)butanoic acid methyl ester, N-benzyloxycarbonyl-3-amino-4-(4-methanesulfonyloxyphenyl)butanoic acid ethyl ester, N-benzyloxycarbonyl-3-amino-4-(4-methanesulfonyloxyphenyl)butanoic acid isopropyl ester, N-benzyloxycarbonyl-3-amino-4-(4-methanesulfonyloxyphenyl)butanoic acid t-butyl ester, N-benzyloxycarbonyl-3-amino-4-(4-methanesulfonyloxyphenyl)butanoic acid benzyl ester, N-benzyloxycarbonyl-3-amino-4-(4-benzenesulfonyloxyphenyl)butanoic acid methyl ester, N-benzyloxycarbonyl-3-amino-4-(4-benzenesulfonyloxyphenyl)butanoic acid ethyl ester, N-benzyloxycarbonyl-3-amino-4-(4-benzenesulfonyloxyphenyl)butanoic acid isopropyl ester, N-benzyloxycarbonyl-3-amino-4-(4-benzenesulfonyloxyphenyl)butanoic acid t-butyl ester, N-benzyloxycarbonyl-3-amino-4-(4-benzenesulfonyloxyphenyl)butanoic acid benzyl ester, N-(t-butyloxycarbonyl)-2-aminomethyl-3-(4-(p-toluenesulfonyloxy)phenyl)propanoic acid methyl ester, N-(t-butyloxycarbonyl)-2-aminomethyl-3-(4-(p-toluenesulfonyloxy)phenyl)propanoic acid ethyl ester, N-(t-butyloxycarbonyl)-2-aminomethyl-3-(4-(p-toluenesulfonyloxy)phenyl)propanoic acid isopropyl ester, N-(t-butyloxycarbonyl)-2-aminomethyl-3-(4-(p-toluenesulfonyloxy)phenyl)propanoic acid t-butyl ester, N-(t-butyloxycarbonyl)-2-aminomethyl-3-(4-(p-toluenesulfonyloxy)phenyl)propanoic acid benzyl ester, N-(t-butyloxycarbonyl)-2-aminomethyl-3-(4-methanesulfonyloxyphenyl)propanoic acid methyl ester, N-(t-butyloxycarbonyl)-2-aminomethyl-3-(4-methanesulfonyloxyphenyl)propanoic acid ethyl ester, N-(t-butyloxycarbonyl)-2-aminomethyl-3-(4-methanesulfonyloxyphenyl)propanoic acid isopropyl ester, N-(t-butyloxycarbonyl)-2-aminomethyl-3-(4-methanesulfonyloxyphenyl)propanoic acid t-butyl ester, N-(t-butyloxycarbonyl)-2-aminomethyl-3-(4-methanesulfonyloxyphenyl)propanoic acid benzyl ester, N-(t-butyloxycarbonyl)-2-aminomethyl-3-(4-benzenesulfonyloxyphenyl)propanoic acid methyl ester, N-(t-butyloxycarbonyl)-2-aminomethyl-3-(4-benzenesulfonyloxyphenyl)propanoic acid ethyl ester, N-(t-butyloxycarbonyl)-2-aminomethyl-3-(4-benzenesulfonyloxyphenyl)propanoic acid isopropyl ester, N-(t-butyloxycarbonyl)-2-aminomethyl-3-(4-benzenesulfonyloxyphenyl)propanoic acid t-butyl ester, N-(t-butyloxycarbonyl)-2-aminomethyl-3-(4-benzenesulfonyloxyphenyl)propanoic acid benzyl ester, N-acetyl-2-aminomethyl-3-(4-(p-toluenesulfonyloxy)phenyl)propanoic acid methyl ester, N-acetyl-2-aminomethyl-3-(4-(p-toluenesulfonyloxy)phenyl)propanoic acid ethyl ester, N-2-aminomethyl-3-(4-(p-toluenesulfonyloxy)phenyl)propanoic acid isopropyl ester, N-2-aminomethyl-3-(4-(p-toluenesulfonyloxy)phenyl)propanoic acid t-butyl ester, N-acetyl-2-aminomethyl-3-(4-(p-toluenesulfonyloxy)phenyl)propanoic acid benzyl ester, N-acetyl-2-aminomethyl-3-(4-methanesulfonyloxyphenyl)propanoic acid methyl ester, N-acetyl-2-aminomethyl-3-(4-methanesulfonyloxyphenyl)propanoic acid ethyl ester, N-acetyl-2-aminomethyl-3-(4-methanesulfonyloxyphenyl)propanoic acid isopropyl ester, N-acetyl-2-aminomethyl-3-(4-methanesulfonyloxyphenyl)propanoic acid t-butyl ester, N-acetyl-2-aminomethyl-3-(4-methanesulfonyloxyphenyl)propanoic acid benzyl ester, N-acetyl-2-aminomethyl-3-(4-benzenesulfonyloxyphenyl)propanoic acid methyl ester, N-acetyl-2-aminomethyl-3-(4-benzenesulfonyloxyphenyl)propanoic acid ethyl ester, N-acetyl-2-aminomethyl-3-(4-benzenesulfonyloxyphenyl)propanoic acid isopropyl ester, N-acetyl-2-aminomethyl-3-(4-benzenesulfonyloxyphenyl)propanoic acid t-butyl ester, N-acetyl-2-aminomethyl-3-(4-benzenesulfonyloxyphenyl)propanoic acid benzyl ester, N-benzyl-2-aminomethyl-3-(4-(p-toluenesulfonyloxy)phenyl)propanoic acid methyl ester, N-benzyl-2-aminomethyl-3-(4-(p-toluenesulfonyloxy)phenyl)propanoic acid ethyl ester, N-benzyl-2-aminomethyl-3-(4-(p-toluenesulfonyloxy)phenyl)propanoic acid isopropyl ester, N-benzyl-2-aminomethyl-3-(4-(p-toluenesulfonyloxy)phenyl)propanoic acid t-butyl ester, N-benzyl-2-aminomethyl-3-(4-(p-toluenesulfonyloxy)phenyl)propanoic acid benzyl ester, N-benzyl-2-aminomethyl-3-(4-methanesulfonyloxyphenyl)propanoic acid methyl ester, N-benzyl-2-aminomethyl-3-(4-methanesulfonyloxyphenyl)propanoic acid ethyl ester, N-benzyl-2-aminomethyl-3-(4-methanesulfonyloxyphenyl)propanoic acid isopropyl ester, N-benzyl-2-aminomethyl-3-(4-methanesulfonyloxyphenyl)propanoic acid t-butyl ester, N-benzyl-2-aminomethyl-3-(4-methanesulfonyloxyphenyl)propanoic acid benzyl ester, N-benzyl-2-aminomethyl-3-(4-benzenesulfonyloxyphenyl)propanoic acid methyl ester, N-benzyl-2-aminomethyl-3-(4-benzenesulfonyloxyphenyl)propanoic acid ethyl ester, N-benzyl-2-aminomethyl-3-(4-benzenesulfonyloxyphenyl)propanoic acid isopropyl ester, N-benzyl-2-aminomethyl-3-(4-benzenesulfonyloxyphenyl)propanoic acid t-butyl ester, N-benzyl-2-aminomethyl-3-(4-benzenesulfonyloxyphenyl)propanoic acid benzyl ester, N-(9-fluorenylmethoxycarbonyl)-2-aminomethyl-3-(4-(p-toluenesulfonyloxy)phenyl)propanoic acid methyl ester, N-(9-fluorenylmethoxycarbonyl)-2-aminomethyl-3-(4-(p-toluenesulfonyloxy)phenyl)propanoic acid ethyl ester, N-(9-fluorenylmethoxycarbonyl)-2-aminomethyl-3-(4-(p-toluenesulfonyloxy)phenyl)propanoic acid isopropyl ester, N-(9-fluorenylmethoxycarbonyl)-2-aminomethyl-3-(4-(p-toluenesulfonyloxy)phenyl)propanoic acid t-butyl ester, N-(9-fluorenylmethoxycarbonyl)-2-aminomethyl-3-(4-(p-toluenesulfonyloxy)phenyl)propanoic acid benzyl ester, N-(9-fluorenylmethoxycarbonyl)-2-aminomethyl-3-(4-methanesulfonyloxyphenyl)propanoic acid methyl ester, N-(9-fluorenylmethoxycarbonyl)-2-aminomethyl-3-(4-methanesulfonyloxyphenyl)propanoic acid ethyl ester, N-(9-fluorenylmethoxycarbonyl)-2-aminomethyl-3-(4-methanesulfonyloxyphenyl)propanoic acid isopropyl ester, N-(9-fluorenylmethoxycarbonyl)-2-aminomethyl-3-(4-methanesulfonyloxyphenyl)propanoic acid t-butyl ester, N-(9-fluorenylmethoxycarbonyl)-2-aminomethyl-3-(4-methanesulfonyloxyphenyl)propanoic acid benzyl ester, N-(9-fluorenylmethoxycarbonyl)-2-aminomethyl-3-(4-benzenesulfonyloxyphenyl)propanoic acid methyl ester, N-(9-fluorenylmethoxycarbonyl)-2-aminomethyl-3-(4-benzenesulfonyloxyphenyl)propanoic acid ethyl ester, N-(9-fluorenylmethoxycarbonyl)-2-aminomethyl-3-(4-benzenesulfonyloxyphenyl)propanoic acid isopropyl ester, N-(9-fluorenylmethoxycarbonyl)-2-aminomethyl-3-(4-benzenesulfonyloxyphenyl)propanoic acid t-butyl ester, N-(9-fluorenylmethoxycarbonyl)-2-aminomethyl-3-(4-benzenesulfonyloxyphenyl)propanoic acid benzyl ester, N-benzyloxycarbonyl-2-aminomethyl-3-(4-(p-toluenesulfonyloxy)phenyl)propanoic acid methyl ester, N-benzyloxycarbonyl-2-aminomethyl-3-(4-(p-toluenesulfonyloxy)phenyl)propanoic acid ethyl ester, N-benzyloxycarbonyl-2-aminomethyl-3-(4-(p-toluenesulfonyloxy)phenyl)propanoic acid isopropyl ester, N-benzyloxycarbonyl-2-aminomethyl-3-(4-(p-toluenesulfonyloxy)phenyl)propanoic acid t-butyl ester, N-benzyloxycarbonyl-2-aminomethyl-3-(4-(p-toluenesulfonyloxy)phenyl)propanoic acid benzyl ester, N-benzyloxycarbonyl-2-aminomethyl-3-(4-methanesulfonyloxyphenyl)propanoic acid methyl ester, N-benzyloxycarbonyl-2-aminomethyl-3-(4-methanesulfonyloxyphenyl)propanoic acid ethyl ester, N-benzyloxycarbonyl-2-aminomethyl-3-(4-methanesulfonyloxyphenyl)propanoic acid isopropyl ester, N-benzyloxycarbonyl-2-aminomethyl-3-(4-methanesulfonyloxyphenyl)propanoic acid t-butyl ester, N-benzyloxycarbonyl-2-aminomethyl-3-(4-methanesulfonyloxyphenyl)propanoic acid benzyl ester, N-benzyloxycarbonyl-2-aminomethyl-3-(4-benzenesulfonyloxyphenyl)propanoic acid methyl ester, N-benzyloxycarbonyl-2-aminomethyl-3-(4-benzenesulfonyloxyphenyl)propanoic acid ethyl ester, N-benzyloxycarbonyl-2-aminomethyl-3-(4-benzenesulfonyloxyphenyl)propanoic acid isopropyl ester, N-benzyloxycarbonyl-2-aminomethyl-3-(4-benzenesulfonyloxyphenyl)propanoic acid t-butyl ester, N-benzyloxycarbonyl-2-aminomethyl-3-(4-benzenesulfonyloxyphenyl)propanoic acid benzyl ester, N-(t-butyloxycarbonyl)-3-aminomethyl-4-(4-(p-toluenesulfonyloxy)phenyl)butanoic acid methyl ester, N-(t-butyloxycarbonyl)-3-aminomethyl-4-(4-(p-toluenesulfonyloxy)phenyl)butanoic acid ethyl ester, N-(t-butyloxycarbonyl)-3-aminomethyl-4-(4-(p-toluenesulfonyloxy)phenyl)butanoic acid isopropyl ester, N-(t-butyloxycarbonyl)-3-aminomethyl-4-(4-(p-toluenesulfonyloxy)phenyl)butanoic acid t-butyl ester, N-(t-butyloxycarbonyl)-3-aminomethyl-4-(4-(p-toluenesulfonyloxy)phenyl)butanoic acid benzyl ester, N-(t-butyloxycarbonyl)-3-aminomethyl-4-(4-methanesulfonyloxyphenyl)butanoic acid methyl ester, N-(t-butyloxycarbonyl)-3-aminomethyl-4-(4-methanesulfonyloxyphenyl)butanoic acid ethyl ester, N-(t-butyloxycarbonyl)-3-aminomethyl-4-(4-methanesulfonyloxyphenyl)butanoic acid isopropyl ester, N-(t-butyloxycarbonyl)-3-aminomethyl-4-(4-methanesulfonyloxyphenyl)butanoic acid t-butyl ester, N-(t-butyloxycarbonyl)-3-aminomethyl-4-(4-methanesulfonyloxyphenyl)butanoic acid benzyl ester, N-(t-butyloxycarbonyl)-3-aminomethyl-4-(4-benzenesulfonyloxyphenyl)butanoic acid methyl ester, N-(t-butyloxycarbonyl)-3-aminomethyl-4-(4-benzenesulfonyloxyphenyl)butanoic acid ethyl ester, N-(t-butyloxycarbonyl)-3-aminomethyl-4-(4-benzenesulfonyloxyphenyl)butanoic acid isopropyl ester, N-(t-butyloxycarbonyl)-3-aminomethyl-4-(4-benzenesulfonyloxyphenyl)butanoic acid t-butyl ester, N-(t-butyloxycarbonyl)-3-aminomethyl-4-(4-benzenesulfonyloxyphenyl)butanoic acid benzyl ester, N-acetyl-3-aminomethyl-4-(4-(p-toluenesulfonyloxy)phenyl)butanoic acid methyl ester, N-acetyl-3-aminomethyl-4-(4-(p-toluenesulfonyloxy)phenyl)butanoic acid ethyl ester, N-3-aminomethyl-4-(4-(p-toluenesulfonyloxy)phenyl)butanoic acid isopropyl ester, N-3-aminomethyl-4-(4-(p-toluenesulfonyloxy)phenyl)butanoic acid t-butyl ester, N-acetyl-3-aminomethyl-4-(4-(p-toluenesulfonyloxy)phenyl)butanoic acid benzyl ester, N-acetyl-3-aminomethyl-4-(4-methanesulfonyloxyphenyl)butanoic acid methyl ester, N-acetyl-3-aminomethyl-4-(4-methanesulfonyloxyphenyl)butanoic acid ethyl ester, N-acetyl-3-aminomethyl-4-(4-methanesulfonyloxyphenyl)butanoic acid isopropyl ester, N-acetyl-3-aminomethyl-4-(4-methanesulfonyloxyphenyl)butanoic acid t-butyl ester, N-acetyl-3-aminomethyl-4-(4-methanesulfonyloxyphenyl)butanoic acid benzyl ester, N-acetyl-3-aminomethyl-4-(4-benzenesulfonyloxyphenyl)butanoic acid methyl ester, N-acetyl-3-aminomethyl-4-(4-benzenesulfonyloxyphenyl)butanoic acid ethyl ester, N-acetyl-3-aminomethyl-4-(4-benzenesulfonyloxyphenyl)butanoic acid isopropyl ester, N-acetyl-3-aminomethyl-4-(4-benzenesulfonyloxyphenyl)butanoic acid t-butyl ester, N-acetyl-3-aminomethyl-4-(4-benzenesulfonyloxyphenyl)butanoic acid benzyl ester, N-benzyl-3-aminomethyl-4-(4-(p-toluenesulfonyloxy)phenyl)butanoic acid methyl ester, N-benzyl-3-aminomethyl-4-(4-(p-toluenesulfonyloxy)phenyl)butanoic acid ethyl ester, N-benzyl-3-aminomethyl-4-(4-(p-toluenesulfonyloxy)phenyl)butanoic acid isopropyl ester, N-benzyl-3-aminomethyl-4-(4-(p-toluenesulfonyloxy)phenyl)butanoic acid t-butyl ester, N-benzyl-3-aminomethyl-4-(4-(p-toluenesulfonyloxy)phenyl)butanoic acid benzyl ester, N-benzyl-3-aminomethyl-4-(4-methanesulfonyloxyphenyl)butanoic acid methyl ester, N-benzyl-3-aminomethyl-4-(4-methanesulfonyloxyphenyl)butanoic acid ethyl ester, N-benzyl-3-aminomethyl-4-(4-methanesulfonyloxyphenyl)butanoic acid isopropyl ester, N-benzyl-3-aminomethyl-4-(4-methanesulfonyloxyphenyl)butanoic acid t-butyl ester, N-benzyl-3-aminomethyl-4-(4-methanesulfonyloxyphenyl)butanoic acid benzyl ester, N-benzyl-3-aminomethyl-4-(4-benzenesulfonyloxyphenyl)butanoic acid methyl ester, N-benzyl-3-aminomethyl-4-(4-benzenesulfonyloxyphenyl)butanoic acid ethyl ester, N-benzyl-3-aminomethyl-4-(4-benzenesulfonyloxyphenyl)butanoic acid isopropyl ester, N-benzyl-3-aminomethyl-4-(4-benzenesulfonyloxyphenyl)butanoic acid t-butyl ester, N-benzyl-3-aminomethyl-4-(4-benzenesulfonyloxyphenyl)butanoic acid benzyl ester, N-(9-fluorenylmethoxycarbonyl)-3-aminomethyl-4-(4-(p-toluenesulfonyloxy)phenyl)butanoic acid methyl ester, N-(9-fluorenylmethoxycarbonyl)-3-aminomethyl-4-(4-(p-toluenesulfonyloxy)phenyl)butanoic acid ethyl ester, N-(9-fluorenylmethoxycarbonyl)-3-aminomethyl-4-(4-(p-toluenesulfonyloxy)phenyl)butanoic acid isopropyl ester, N-(9-fluorenylmethoxycarbonyl)-3-aminomethyl-4-(4-(p-toluenesulfonyloxy)phenyl)butanoic acid t-butyl ester, N-(9-fluorenylmethoxycarbonyl)-3-aminomethyl-4-(4-(p-toluenesulfonyloxy)phenyl)butanoic acid benzyl ester, N-(9-fluorenylmethoxycarbonyl)-3-aminomethyl-4-(4-methanesulfonyloxyphenyl)butanoic acid methyl ester, N-(9-fluorenylmethoxycarbonyl)-3-aminomethyl-4-(4-methanesulfonyloxyphenyl)butanoic acid ethyl ester, N-(9-fluorenylmethoxycarbonyl)-3-aminomethyl-4-(4-methanesulfonyloxyphenyl)butanoic acid isopropyl ester, N-(9-fluorenylmethoxycarbonyl)-3-aminomethyl-4-(4-methanesulfonyloxyphenyl)butanoic acid t-butyl ester, N-(9-fluorenylmethoxycarbonyl)-3-aminomethyl-4-(4-methanesulfonyloxyphenyl)butanoic acid benzyl ester, N-(9-fluorenylmethoxycarbonyl)-3-aminomethyl-4-(4-benzenesulfonyloxyphenyl)butanoic acid methyl ester, N-(9-fluorenylmethoxycarbonyl)-3-aminomethyl-4-(4-benzenesulfonyloxyphenyl)butanoic acid ethyl ester, N-(9-fluorenylmethoxycarbonyl)-3-aminomethyl-4-(4-benzenesulfonyloxyphenyl)butanoic acid isopropyl ester, N-(9-fluorenylmethoxycarbonyl)-3-aminomethyl-4-(4-benzenesulfonyloxyphenyl)butanoic acid t-butyl ester, N-(9-fluorenylmethoxycarbonyl)-3-aminomethyl-4-(4-benzenesulfonyloxyphenyl)butanoic acid benzyl ester, N-benzyloxycarbonyl-3-aminomethyl-4-(4-(p-toluenesulfonyloxy)phenyl)butanoic acid methyl ester, N-benzyloxycarbonyl-3-aminomethyl-4-(4-(p-toluenesulfonyloxy)phenyl)butanoic acid ethyl ester, N-benzyloxycarbonyl-3-aminomethyl-4-(4-(p-toluenesulfonyloxy)phenyl)butanoic acid isopropyl ester, N-benzyloxycarbonyl-3-aminomethyl-4-(4-(p-toluenesulfonyloxy)phenyl)butanoic acid t-butyl ester, N-benzyloxycarbonyl-3-aminomethyl-4-(4-(p-toluenesulfonyloxy)phenyl)butanoic acid benzyl ester, N-benzyloxycarbonyl-3-aminomethyl-4-(4-methanesulfonyloxyphenyl)butanoic acid methyl ester, N-benzyloxycarbonyl-3-aminomethyl-4-(4-methanesulfonyloxyphenyl)butanoic acid ethyl ester, N-benzyloxycarbonyl-3-aminomethyl-4-(4-methanesulfonyloxyphenyl)butanoic acid isopropyl ester, N-benzyloxycarbonyl-3-aminomethyl-4-(4-methanesulfonyloxyphenyl)butanoic acid t-butyl ester, N-benzyloxycarbonyl-3-aminomethyl-4-(4-methanesulfonyloxyphenyl)butanoic acid benzyl ester, N-benzyloxycarbonyl-3-aminomethyl-4-(4-benzenesulfonyloxyphenyl)butanoic acid methyl ester, N-benzyloxycarbonyl-3-aminomethyl-4-(4-benzenesulfonyloxyphenyl)butanoic acid ethyl ester, N-benzyloxycarbonyl-3-aminomethyl-4-(4-benzenesulfonyloxyphenyl)butanoic acid isopropyl ester, N-benzyloxycarbonyl-3-aminomethyl-4-(4-benzenesulfonyloxyphenyl)butanoic acid t-butyl ester, N-benzyloxycarbonyl-3-aminomethyl-4-(4-benzenesulfonyloxyphenyl)butanoic acid benzyl ester, etc.

Furthermore, the above-mentioned compounds wherein the hydrogen on the aromatic ring is substituted with a fluorine atom, an alkyl group, a cycloalkyl group, a hydroxyl group, an alkoxyl group, an aryloxy group, an alkylthio group, an arylthio group, a cyano group, a nitro group, a protected amino group, a substituted or unsubstituted sulfonamide group, a formyl group, a carboxyl group, an alkylcarbonyl group, an arylcarbonyl group, an alkoxycarbonyl group, an aryloxycarbonyl group, a substituted or unsubstituted carbamoyl group, a substituted or unsubstituted heterocyclic group, or a substituted or unsubstituted aryl group as mentioned above, are included.

The unsubstituted aryl group represented by $R^3$ in the organic boron compound (2) and boroxine ring compound (3) includes, but not specifically limited to, a monocyclic to tricyclic aryl group consisting of 6 to 14 carbon atoms. Examples of such aryl group include a phenyl group, a naphthyl group, an anthracenyl group, a phenanthryl group, an indenyl group and a fluorenyl group. Furthermore, the unsubstituted heteroaryl group represented by $R^3$ includes, but not specifically limited to, a 5- to 7-membered aromatic heterocyclic group containing 1 to 3 heteroatoms selected from 0 to 3 nitrogen atoms, 0 to 2 oxygen atoms and 0 to 2 sulfur atoms. Examples of such heteroaryl group include a pyridyl group, a furyl group, a thienyl group, a pyrrolyl group and imidazolyl group.

The substituents for the substituted aryl group or substituted heteroaryl group represented by $R^3$ include one or more identical or different substituents. Specific examples thereof include a fluorine atom; substituted or unsubstituted alkyl groups such as a methyl group, an ethyl group, an i-propyl group, a trifluoromethyl group, a cycloalkyl group or alkylaminoalkyl groups such as a dimethylaminomethyl group; protected hydroxyl groups; alkoxy groups such as a methoxy group, an ethoxy group or a t-butoxy group; a phenoxy group; alkylthio groups such as a methylthio group; arylthio groups such as a phenylthio group; a cyano group; a nitro group; alkyl-substituted amino groups such as a dimethylamino group or a cyclohexylamino group; acylamino groups such as a t-butoxycarbonylamino group or an acetoxyamino group; protected amino groups such as imide groups such as a phthalimide group; sulfonamide groups such as a benzenesulfonamide group or a methanesulfonamide group; a imino group; a formyl group; a carboxyl group; substituted or unsubstituted alkoxycarbonyl groups such as a methoxycarboxyl group; substituted or unsubstituted aryloxycarbonyl groups such as a p-methoxyphenoxycarbonyl group; unsubstituted or substituted carbamoyl groups such as a carbamoyl group or a N-phenylcarbamoyl group; substituted or unsubstituted heterocyclic groups such as a pyridyl group, a furyl group or thienyl group; and substituted or unsubstituted aryl groups such as a phenyl group or a naphthyl group of these substituents, two substituents on the adjacent carbon atoms may be bound each other and taken together with $R^3$ to form a fused ring.

Specific examples of the organic boron compound of the formula (2) of the present invention include phenylboronic acid, 2-methylphenylboronic acid, 3-methylphenylboronic acid, 4-methylphenylboronic acid, 2,3-dimethylphenylboronic acid, 2,4-dimethylphenylboronic acid, 2,5-dimethylphenylboronic acid, 2,6-dlmethylphenylboronic acid, 2,4,6-trimethylphenylboronic acid, 2,3,5,6-tetramethylphenylboronic acid, 2-ethylphenylboronic acid, 4-n-propylphenylboronic acid, 4-isopropylphenylboronic acid, 4-n-butylphenylboronic acid, 4-t-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-fluorenylboronic acid, 9-phenanthrenylboronic acid, 9-anthracenylboronic acid, 1-pyrenylboronic acid, 2-trifluoromethylphenylboronic acid, 3-trifluoromethylphenylboronic acid, 4-trifluorophenylboronic acid, 3,5-bis(trifluoromethyl)phenylboronic acid, 2-methoxyphenylboronic acid, 3-methoxyphenylboronic acid, 4-methoxyphenylboronic acid, 2,5-dimethoxyphenylboronic acid, 2,6-dimethoxyphenylboronic acid, 4,5-dimethoxyphenylboronic acid, 2,4-dimethoxyphenylboronic acid, 2-ethoxyphenylboronic acid, 3-ethoxyphenylboronic acid, 4-ethoxyphenylboronic acid, 4-phenoxyboronic acid, 3,4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 2,6-difluorophenylboronic acid, 4,5-difluorophenylboronic acid, 3,5-difluorophenylboronic acid, 2-formylphenylboronic acid, 3-formylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 3-nitrophenylboronic acid, 3-acetylphenylboronic acid, 4-acetylphenylboronic acid, 3-trifluoroacetylphenylboronic acid, 4-trifluoroacetylphenylboronic acid, 4-methylthiophenylboronic acid, 4-vinylphenylboronic acid, 3-carboxyphenylboronic acid, 4-carboxyphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-diethylamino)phenylboronic acid, 3-(N,N-diethylamino)phenylboronic acid, 4-(N,N-diethylamino)phenylboronic acid, 2-(N,N-dimethylaminomethyl)phenylboronic acid, furan-2-boronic acid, furan-3-boronic acid, 2-formylfuranboronic acid, 3-formylfuran-2-boronic acid, dibenzofuran-4-boronic acid, benzofuran-2-boronic acid, thiophene-2-boronic acid, thiophene-3-boronic acid, 5-methylthiophene-2-boronic acid, 5-chlorothiophene-2-boronic acid, 4-methylthiophene-2-boronic acid, 5-methylthiophene-2-boronic acid, 2-acetylthiophene-5-boronic acid, 3-formylthiophene-2-boronic acid, 5-methylthiophene-2-boronic acid, benzothiophene-2-boronic acid, dibenzothiophene-4-boronic acid, pyrazole-4-boronic acid, 3-methylpyrazole-4-boronic acid, 3,5-dimethylpyrazole-4-boronic acid, 3-nitro-1,2,4-triazole-5-boronic acid, thiazole-2-boronic acid, pyridine-3-boronic acid, pyridine-4-boronic acid, pyrimidine-5-boronic acid, quinoline-8-boronic acid, isoquinoline-4-boronic acid, 1,4-benzenebis (boronic acid), and pinacol esters and catechol esters of these boronic acids.

In the reaction, the amount used of the organic boron compound of the formula (2) is usually from 1 mol to 10 mol, preferably not more than 3 mol, relative to 1 mol of the aromatic sulfonic acid ester compound of the formula (1).

The nickel catalyst used may be zerovalent or divalent. Alternatively, a divalent nickel catalyst may be previously reduced to zerovalence by using a reducing agent before use. The zerovalent catalyst includes bis(1,5-cyclooctadiene) nickel(0) and tetrakis(triphenylphosphine)nickel(0). The divalent catalyst includes nickel halide metal compounds (II) such as nickel(II) chloride, nickel(II) bromide and nickel(II) iodide, nickel(II) nitrate, nickel(II) acetate, bis(triphenylphosphine)nickel(II) dichloride, and nickel(II) bisacetylacetonate. These nickel catalysts may optionally contain a ligand. Alternatively, a ligand may be added to the reaction mixture independently. Such a ligand includes phosphorus-containing compounds, for example, triarylphosphines such as triphenylphosphine, trialkylphosphines such as tricyclohexylphosphine or tri-t-butylphosphine, bis(diphenylphosphino)ferrocene, etc.

The reducing agent used for previously reducing the divalent nickel to zerovalence includes, but not limited to, sodium borohydride, lithium aluminum hydride, sodium hydride, di-isobutylaluminum hydride, alkyl Grignard's reagents, alkyl lithiums, alkyl aluminums, and zinc metals. In this case, a divalent nickel catalyst, a ligand, a reducing agent and optionally a suitable solvent that does not react with the reducing agent are mixed to prepare a catalyst, but order thereof is not specifically limited.

The nickel catalyst may be completely dissolved or suspended in the reaction mixture. The nickel catalyst may be used directly, or may be carried by a substance that does not dissolve in a solvent used in the reaction, such as carbon, silica or alumina.

In the reaction, the amount used of the nickel catalyst is usually from 0.00001 mol to 1 mol, preferably not more than 0.2 mol, relative to 1 mol of the aromatic sulfonic acid ester compound of the formula (1). The amount used of the ligand is usually from 0.1 mol to 10 mol, preferably from 0.5 mol to 5 mol relative to 1 mol of the nickel catalyst.

In the present invention, a base is usually used. Such a base includes hydroxide, carbonate, phosphate, carboxylate and alkoxide of an alkali metal or alkaline earth metal, and alkali metal hydrogencarbonate and alkali metal fluoride. Such salts of alkali metal and alkaline earth metal include inorganic bases such as lithium carbonate, sodium carbonate, potassium carbonate, cesium carbonate, calcium carbonate, barium carbonate, lithium phosphate, sodium phosphate and potassium phosphate, preferably cesium carbonate. The base further includes tertiary amine compounds such as trimethylamine, triethylamine, N,N-dimethylbenzylamine and N,N-diethylaniline.

The amount used of the base is usually from 0.1 to 20 mol, preferably 1 to 5 mol, relative to 1 mol of the aromatic sulfonic acid ester compound of the formula (1). Furthermore, two or more of the bases may be used in combination.

In the reaction, a solvent is usually used. Organic solvents, water, or mixtures thereof may be used as a solvent.

The organic solvent includes alcohol solvents such as methanol and ethanol, aprotic solvents such as N-methylpyrrolidone, N,N-dimethylformamide, dimethylsulfoxide and acetonitrile, ether solvents such as diethyl ether, di-isopropyl ether, diethylene glycol dimethyl ether, 1,4-dioxane and tetrahydrofuran, aromatic hydrocarbons such as benzene, toluene and xylene, aliphatic hydrocarbons such as hexane and heptane. These solvents may be used alone or in a combination of two or more. The amount used of the solvent is usually from 0.5 to 200 parts by weight, preferably from 1 to 10 parts by weight, relative to 1 part by weight of the aromatic sulfonic acid ester compound of the formula (1).

In the preparation process of the present invention, the aromatic sulfonic acid ester compound of formula (1), organic boron compound of the formula (2), nickel catalyst, ligand, base and, if necessary, a solvent may be mixed in any order. However, in the case wherein a reducing agent is used and the agent may react with the aromatic amino acid derivative or organic boron compound, it is preferable that the above materials are added in the order whereby the reaction of the reducing agent with the aromatic amino acid derivative or organic boron compound can be avoided. For example, it is preferable that an aromatic amino acid derivative, an organic boron compound, a base and optionally a suitable solvent are mixed previously in any order and then to the mixture, a mixture prepared from a nickel catalyst, a ligand and a reducing agent is added; or to a mixture prepared from a nickel catalyst, a ligand and a reducing agent, an aromatic amino acid derivative, an organic boron compound, a base and optionally a suitable solvent are added in any order. In addition, in this case, a compound in which a ligand is coordinated to a nickel catalyst may be used instead of a ligand and a nickel catalyst.

The reaction temperature is usually 70° C. or below, preferably in the range of room temperature to 50° C.

After the reaction, insoluble substances in the system are removed by filtration etc., if necessary, and a usual post-treatment is carried out to give the desired optically active biaryl compound of the following formula (4):

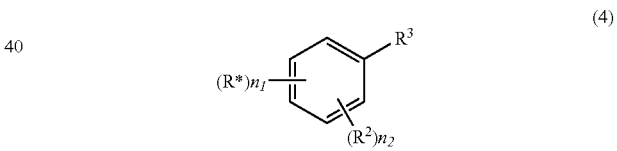

(4)

wherein $R^*$, $R^2$, $R^3$, $n_1$, $n_2$ and * are as defined hereinabove, with fine optical purity.

Particularly, when the optically active amino acid compound of the formula (1a) is used as a starting compound, the optically active biaryl amino acid compound of the following formula (4a):

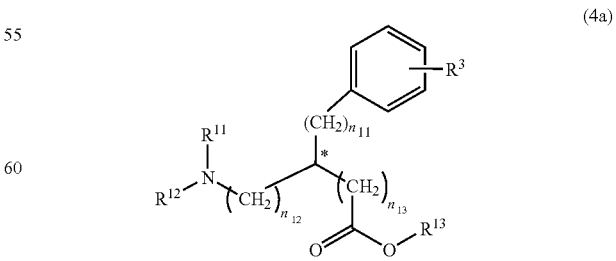

(4a)

wherein $R^3$, $R^{11}$, $R^{12}$, $R^{13}$, $n_{11}$, $n_{12}$, $n_{13}$ and * are as defined hereinabove, can be obtained with fine optical purity. Not only the optically active amino acid compounds (1a) and (4a) but also compositions comprising the optically active compound of the formula (1a) or (4a) and an enantiomer thereof in any ratio (inclusive of a racemate) can be prepared similarly to the optically active compounds.

EXAMPLES

The following examples explain the present invention more particularly, but they do not limit the present invention.

Example 1

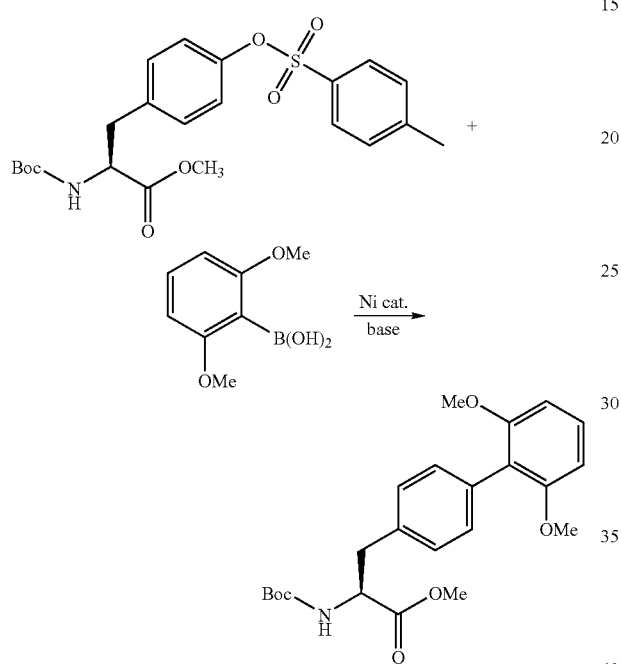

Under a nitrogen atmosphere, (L)-N-(t-butyloxycarbonyl)-O-(p-toluenesulfonyl)tyrosine methyl ester (0.94 g, 2.0 mmol), 2,6-dimethoxyphenylboronic acid (0.55 g, 3.0 mmol), cesium carbonate (1.32 g, 4.0 mmol), tricyclohexylphosphine (0.059 g, 0.2 mmol) and bis(1,5-cyclooctadiene)nickel (0.028 g, 0.1 mmol) were mixed in dioxane (2 ml). The reaction mixture was heated to 50° C. and then stirred at the same temperature for 15 hrs. After the reaction was completed, the mixture was left to cool to room temperature and insoluble substances were filtered off. The filtrate was subjected to liquid chromatography to analyze (L)-N-(t-butyloxycarbonyl)-4-(2,6-dimethoxyphenyl)phenylalanine methyl ester in the filtrate. As the result, the reaction yield was 100% and the optical purity of the product was 99.8% ee.

Example 2

Under a nitrogen atmosphere, (L)-N-(t-butyloxycarbonyl)-O-(p-toluenesulfonyl)tyrosine methyl ester (0.94 g, 2.0 mmol), 2,6-dimethoxyphenylboronic acid (0.55 g, 3.0 mmol), potassium phosphate (0.86 g, 4.1 mmol), tricyclohexylphosphine (0.059 g, 0.2 mmol) and bis(1,5-cyclooctadiene)nickel (0.027 g, 0.1 mmol) were mixed in THF (3 ml). The reaction mixture was heated to 50° C. and then stirred at the same temperature for 15 hrs. After the reaction was completed, the mixture was left to cool to room temperature and insoluble substances were filtered off. The filtrate was subjected to liquid chromatography to analyze (L)-N-(t-butyloxycarbonyl)-4-(2,6-dimethoxyphenyl)phenylalanine methyl ester in the filtrate. As the result, the reaction yield was 94%.

Example 3

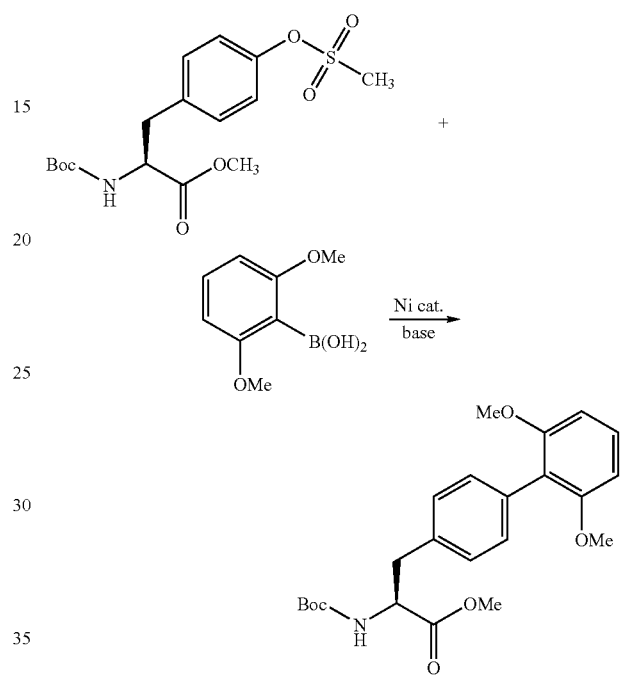

Under a nitrogen atmosphere, (L)-N-(t-butyloxycarbonyl)-O-methanesulfonyltyrosine methyl ester (1.45 g, 4.0 mmol), 2,6-dimethoxyphenylboronic acid (1.1 g, 6.0 mmol), cesium carbonate (2.6 g, 8.0 mmol), tricyclohexylphosphine (0.12 g, 0.4 mmol) and bis(1,5-cyclooctadiene)nickel (0.055 g, 0.2 mmol) were mixed in dioxane (4 ml). The reaction mixture was heated to 50° C. and then stirred at the same temperature for 5 hrs. After the reaction was completed, the mixture was left to cool to room temperature and insoluble substances were filtered off. The filtrate was subjected to liquid chromatography to analyze (L)-N-(t-butyloxycarbonyl)-4-(2,6-dimethoxyphenyl)phenylalanine methyl ester in the filtrate. As the result, the reaction yield was 95%.

Example 4

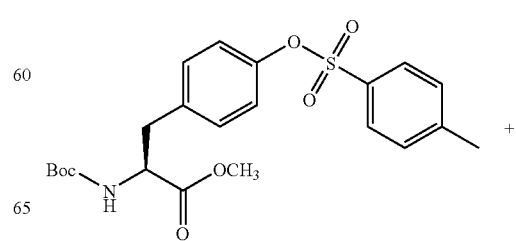

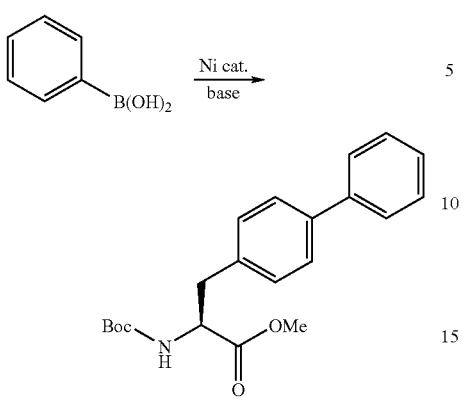

Under a nitrogen atmosphere, (L)-N-(t-butyloxycarbonyl)-O-(p-toluenesulfonyl)tyrosine methyl ester (0.45 g, 1.0 mmol), cesium carbonate (0.65 g, 2.0 mmol), tricyclohexylphosphine (0.059 g, 0.2 mmol) and bis(1,5-cyclooctadiene)nickel (0.028 g, 0.1 mmol) were mixed in dioxane (1 ml) which had been previously mixed with a mixture (0.24 g, 2.0 mmol) of phenylboronic acid and a boroxine ring compound thereof and water (0.03 g). The reaction mixture was heated to 50° C. and then stirred at the same temperature for 9 hrs. After the reaction was completed, the mixture was left to cool to room temperature and insoluble substances were filtered off. The filtrate was subjected to column chromatography purification to obtain (L)-N-(t-butyloxycarbonyl)-4-phenylphenylalanine methyl ester (0.33 g, yield 95%) as white crystals.

Example 5

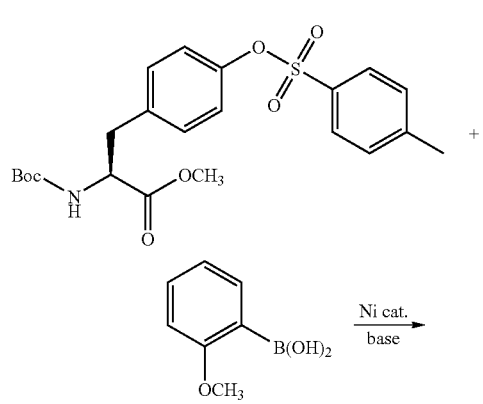

Under a nitrogen atmosphere, (L)-N-(t-butyloxycarbonyl)-O-(p-toluenesulfonyl)tyrosine methyl ester (0.45 g, 1.0 mmol), cesium carbonate (0.65 g, 2.0 mmol), tricyclohexylphosphine (0.059 g, 0.2 mmol), bis(1,5-cyclooctadiene)nickel (0.028 g, 0.1 mmol) and 2-methoxyphenylboronic acid (0.32 g, 2.0 mmol) were mixed in dioxane (2 ml). The reaction mixture was heated to 70° C. and then stirred at the same temperature for 3 hrs. After the reaction was completed, the mixture was left to cool to room temperature and insoluble substances were filtered off. The filtrate was subjected to column chromatography purification to obtain (L)-N-(t-butyloxycarbonyl)-4-(2-methoxyphenyl)phenylalanine methyl ester (0.38 g, yield 98%) as pale yellow oil.

Example 6

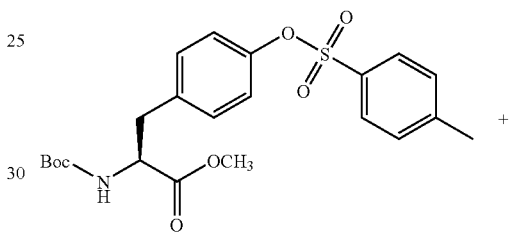

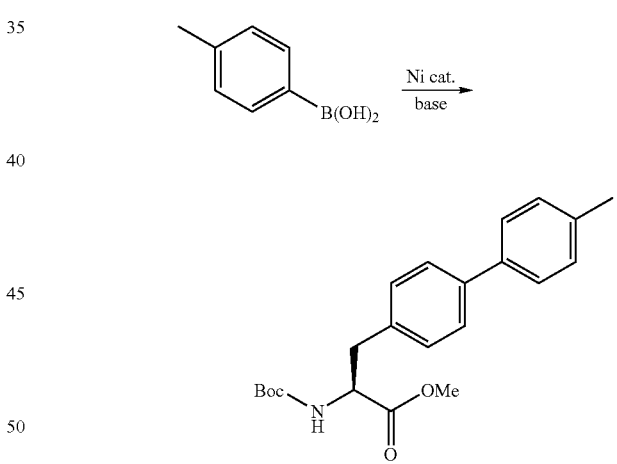

Under a nitrogen atmosphere, (L)-N-(t-butyloxycarbonyl)-O-(p-toluenesulfonyl)tyrosine methyl ester (0.45 g, 1.0 mmol), cesium carbonate (0.65 g, 2.0 mmol), tricyclohexylphosphine (0.059 g, 0.2 mmol) and bis(1,5-cyclooctadiene)nickel (0.028 g, 0.1 mmol) were mixed in dioxane (1 ml) which had been previously mixed with a mixture (0.28 g, 2.0 mmol) of 4-methylphenylboronic acid and a boroxine ring compound thereof and water (0.03 g). The reaction mixture was heated to 70° C. and then stirred at the same temperature for 3 hrs. After the reaction was completed, the mixture was left to cool to room temperature and insoluble substances were filtered off. The filtrate was subjected to column chromatography purification to obtain (L)-N-(t-butyloxycarbonyl)-4-(4-methylphenyl)phenylalanine methyl ester (0.33 g, yield 89%) as white crystals.

Example 7

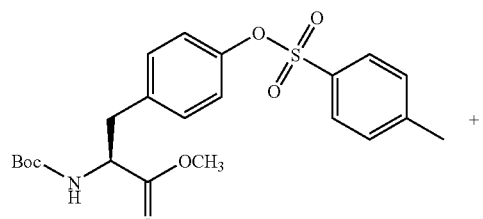

+

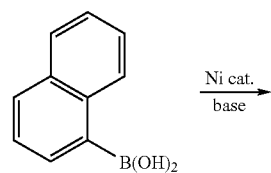

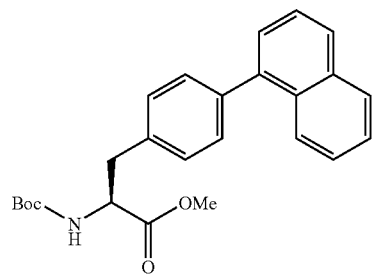

Under a nitrogen atmosphere, (L)-N-(t-butyloxycarbonyl)-O-(p-toluenesulfonyl)tyrosine methyl ester (0.45 g, 1.0 mmol), cesium carbonate (0.65 g, 2.0 mmol), tricyclohexylphosphine (0.059 g, 0.2 mmol) and bis(1,5-cyclooctadiene) nickel (0.028 g, 0.1 mmol) were mixed in dioxane (1.25 ml) which had been previously mixed with a mixture (0.34 g, 2.0 mmol) of 1-naphthylboronic acid and a boroxine ring compound thereof and water (0.02 g). The reaction mixture was heated to 70° C. and then stirred at the same temperature for 4 hrs. After the reaction was completed, the mixture was left to cool to room temperature and insoluble substances were filtered off. The filtrate was subjected to column chromatography purification to obtain (L)-N-(t-butyloxycarbonyl)-4-(1-naphthyl)phenylalanine methyl ester (0.39 g, yield 96%) as white crystals.

Example 8

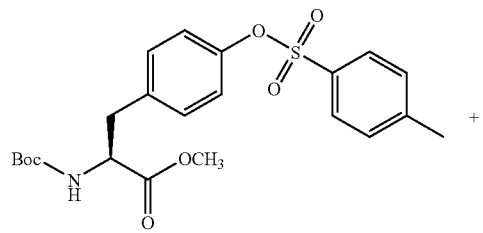

+

-continued

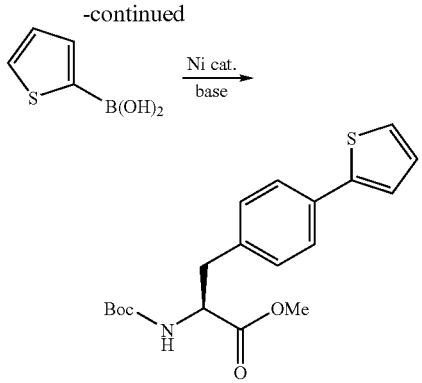

Under a nitrogen atmosphere, (L)-N-(t-butyloxycarbonyl)-O-(p-toluenesulfonyl)tyrosine methyl ester (0.45 g, 1.0 mmol), cesium carbonate (0.65 g, 2.0 mmol), tricyclohexylphosphine (0.059 g, 0.2 mmol) and bis(1,5-cyclooctadiene) nickel (0.028 g, 0.1 mmol) were mixed in dioxane (1.5 ml) which had been previously mixed with a mixture (0.26 g, 2.0 mmol) of 2-thiopheneboronic acid and a boroxine ring compound thereof and water (0.03 g). The reaction mixture was heated to 50° C. and then stirred at the same temperature for 7 hrs. After the reaction was completed, the mixture was left to cool to room temperature and insoluble substances were filtered off. The filtrate was subjected to column chromatography purification to obtain (L)-N-(t-butyloxycarbonyl)-4-(thiophen-2-yl)phenylalanine methyl ester (0.20 g, yield 56%) as pale yellow crystals.

Example 9

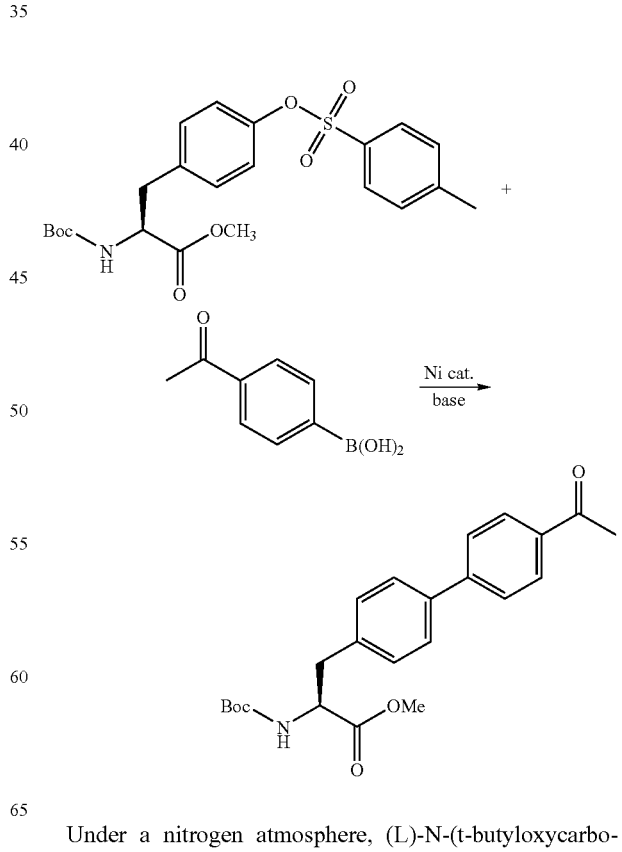

Under a nitrogen atmosphere, (L)-N-(t-butyloxycarbonyl)-O-(p-toluenesulfonyl)tyrosine methyl ester (0.45 g, 1.0 mmol), cesium carbonate (0.65 g, 2.0 mmol), tricyclohexylphosphine (0.059 g, 0.2 mmol) and bis(1,5-cyclooctadiene) nickel (0.028 g, 0.1 mmol) were mixed in dioxane (1 ml) which had been previously mixed with a mixture (0.33 g, 2.0 mmol) of 4-acetylphenylboronic acid and a boroxine ring compound thereof and water (0.02 g). The reaction mixture was heated to 70° C. and then stirred at the same temperature for 8 hrs. After the reaction was completed, the mixture was left to cool to room temperature and insoluble substances were filtered off. The filtrate was subjected to column chromatography purification to obtain (L)-N-(t-butyloxycarbonyl)-4-(4-acetylphenyl)phenylalanine methyl ester (0.33 g, yield 89%) as white crystals.

Example 10

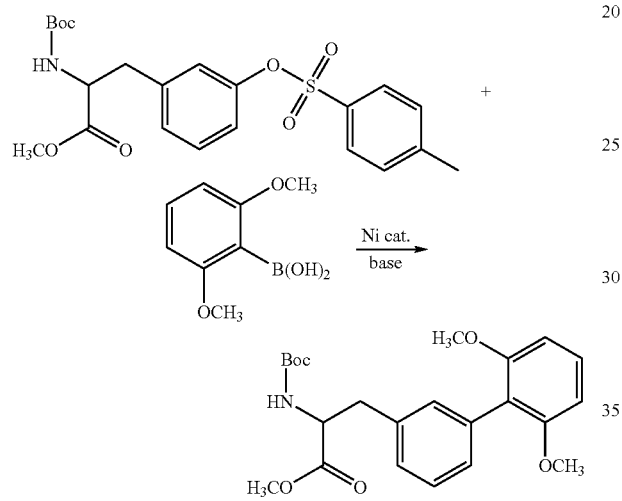

Under a nitrogen atmosphere, N-(t-butyloxycarbonyl)-O-(p-toluenesulfonyl)-m-tyrosine methyl ester (0.45 g, 1.0 mmol), cesium carbonate (0.65 g, 2.0 mmol), tricyclohexylphosphine (0.059 g, 0.2 mmol), bis(1,5-cyclooctadiene) nickel (0.028 g, 0.1 mmol) and 2,6-dimethoxyphenylboronic acid (0.36 g, 2.0 mmol) were mixed in dioxane (1 ml). The reaction mixture was heated to 60° C. and then stirred at the same temperature for 2 hrs. After the reaction was completed, the mixture was left to cool to room temperature and insoluble substances were filtered off. The filtrate was subjected to column chromatography purification to obtain N-(t-butyloxycarbonyl)-3-(2,6-dimethoxyphenyl)phenylalanine methyl ester (0.39 g, yield 93%) as white crystals.

Example 11

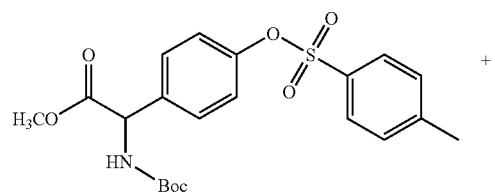

-continued

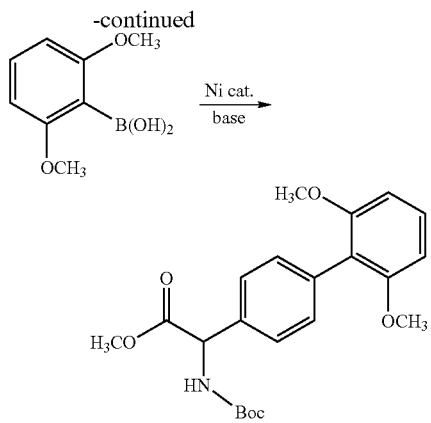

Under a nitrogen atmosphere, methyl N-(t-butyloxycarbonyl)-2-amino-2-(4-toluenesulfonyloxyphenyl)acetate (0.44 g, 1.0 mmol), cesium carbonate (0.65 g, 2.0 mmol), tricyclohexylphosphine (0.059 g, 0.2 mmol), bis(1,5-cyclooctadiene) nickel (0.028 g, 0.1 mmol) and 2,6-dimethoxyphenylboronic acid (0.36 g, 2.0 mmol) were mixed in dioxane (1 ml). The reaction mixture was heated to 70° C. and then stirred at the same temperature for 9 hrs. After the reaction was completed, the mixture was left to cool to room temperature and insoluble substances were filtered off. The filtrate was subjected to column chromatography purification to obtain methyl N-(t-butyloxycarbonyl)-2-amino-2-[4-(2,6-dimethoxyphenyl)phenyl]acetate (0.29 g, yield 72%) as pale yellow oil.

Example 12

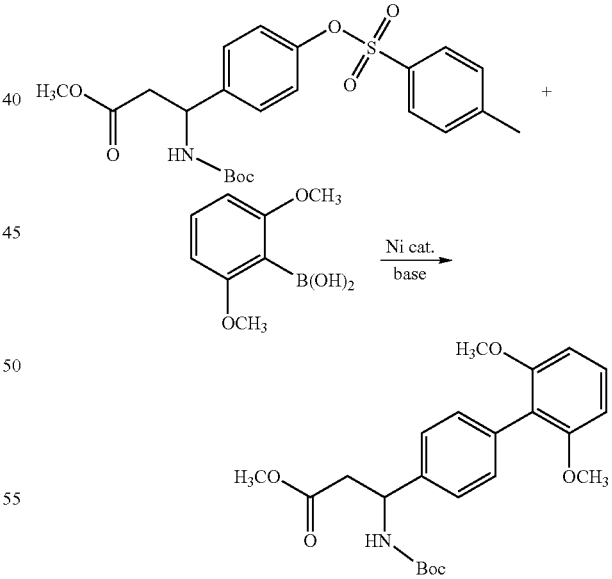

Under a nitrogen atmosphere, methyl N-(t-butyloxycarbonyl)-3-amino-3-(4-toluenesulfonyloxyphenyl)propionate (0.45 g, 1.0 mmol), cesium carbonate (0.65 g, 2.0 mmol), tricyclohexylphosphine (0.059 g, 0.2 mmol), bis(1,5-cyclooctadiene)nickel (0.028 g, 0.1 mmol) and 2,6-dimethoxyphenylboronic acid (0.36 g, 2.0 mmol) were mixed in dioxane (1 ml). The reaction mixture was heated to 50° C. and then stirred at the same temperature for 2 hrs. After the reaction was completed, the mixture was left to cool to room temperature and insoluble substances were filtered off. The filtrate was subjected to column chromatography purification to obtain methyl N-(t-butyloxycarbonyl)-3-amino-3-[4-(2,6-dimethoxyphenyl)phenyl]propionate (0.34 g, yield 83%) as colorless oil.

Comparative Example 1

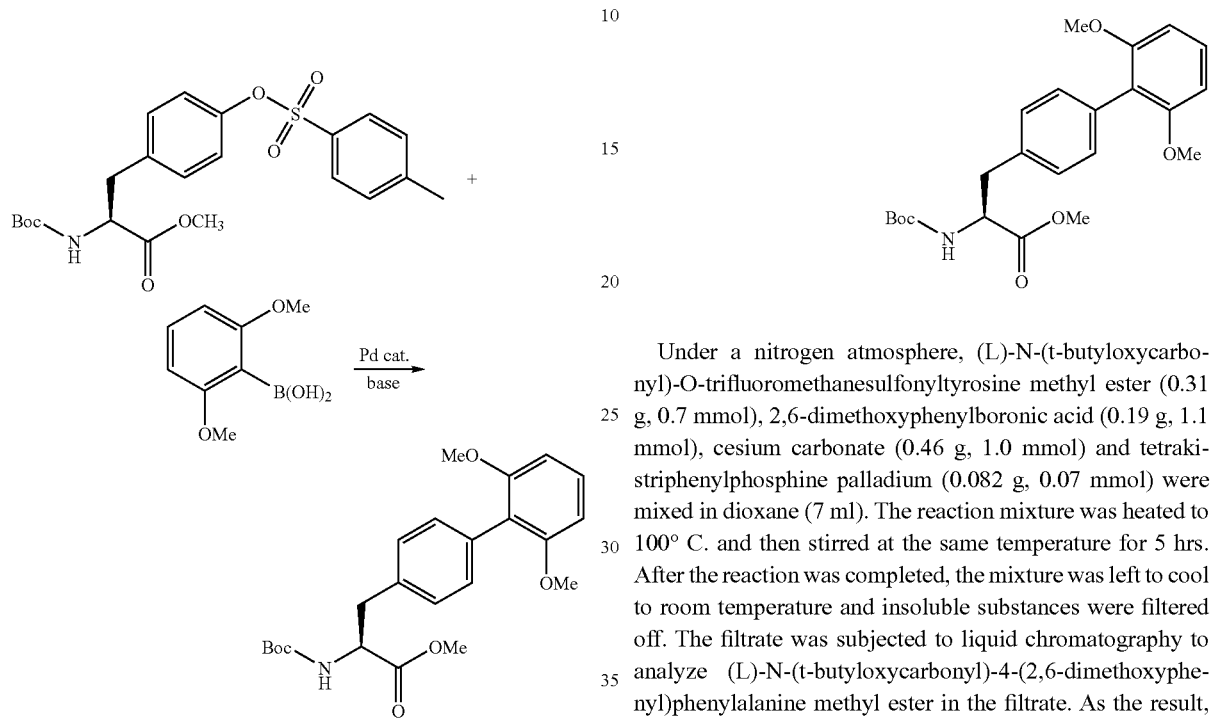

Under a nitrogen atmosphere, (L)-N-(t-butyloxycarbonyl)-O-(p-toluenesulfonyl)tyrosine methyl ester (0.90 g, 2.0 mmol), 2,6-dimethoxyphenylboronic acid (0.55 g, 3.0 mmol), cesium carbonate (1.30 g, 4.0 mmol) and tetrakis(triphenylphosphine)palladium (0.23 g, 0.2 mmol) were mixed in dioxane (2 ml). The reaction mixture was heated to 50° C. and then stirred at the same temperature for 5 hrs. After the reaction was completed, the mixture was left to cool to room temperature and insoluble substances were filtered off. The filtrate was subjected to liquid chromatography to analyze (L)-N-(t-butyloxycarbonyl)-4-(2,6-dimethoxyphenyl)phenylalanine methyl ester in the filtrate. As the result, the reaction yield was 0% and the recovery percentage of the starting material was 96%.

Comparative Example 2

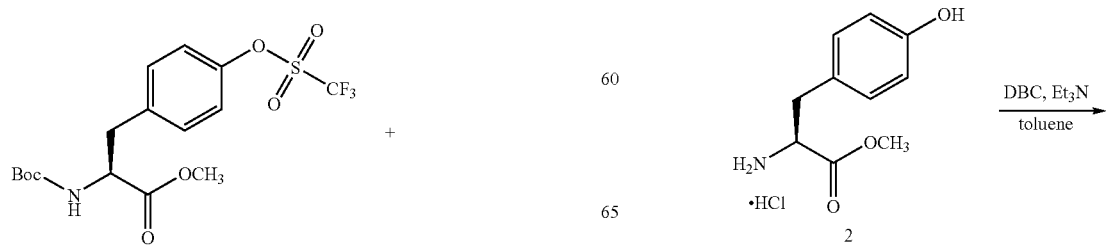

Under a nitrogen atmosphere, (L)-N-(t-butyloxycarbonyl)-O-trifluoromethanesulfonyltyrosine methyl ester (0.31 g, 0.7 mmol), 2,6-dimethoxyphenylboronic acid (0.19 g, 1.1 mmol), cesium carbonate (0.46 g, 1.0 mmol) and tetrakistriphenylphosphine palladium (0.082 g, 0.07 mmol) were mixed in dioxane (7 ml). The reaction mixture was heated to 100° C. and then stirred at the same temperature for 5 hrs. After the reaction was completed, the mixture was left to cool to room temperature and insoluble substances were filtered off. The filtrate was subjected to liquid chromatography to analyze (L)-N-(t-butyloxycarbonyl)-4-(2,6-dimethoxyphenyl)phenylalanine methyl ester in the filtrate. As the result, the reaction yield was 63% and the recovery percentage of the starting material was 0%. Furthermore, the optical purity of the product was 79.5% ee.

Example 13

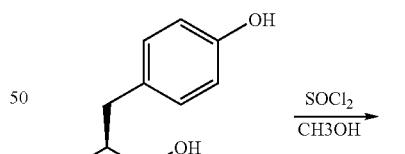

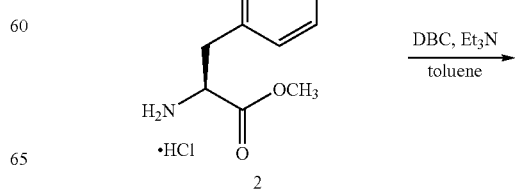

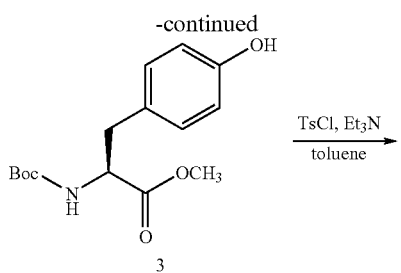

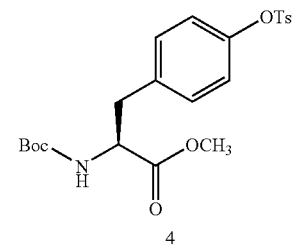

Protection of a Carboxylic Acid Moiety (Synthesis of Compound 2)

L-tyrosine 1 (181.2 g, 1.0 mol) was suspended in methanol (1268 g), and thionyl chloride (428.3 g, 3.6 mol) was added dropwise thereto at 40° C. over 2 hrs. After further keeping at 40° C. for 3 hrs, the reaction mass was concentrated to about one third of the volume under reduced pressure. To the concentrate mass was added dropwise toluene (1268 g) at 40° C. over 1.5 hrs. After keeping at 0° C. for 1 hr, precipitates were filtered and dried under reduced pressure to give L-tyrosine methyl ester hydrochloride 2 (208.7 g, yield 90.1%) as white crystals.

Protection of an Amino Group (Synthesis of Compound 3)

L-tyrosine methyl ester hydrochloride 2 (104.3 g, 0.45 mol) and di-t-butylcarbonate (DBC, 98.2 g, 0.45 mol) were suspended in toluene (521.3 g), and triethylamine (50.1 g, 0.495 mol) was added dropwise thereto at 20° C. over 1.5 hrs. After further keeping at 20° C. for 4 hrs, the reaction mass was washed with 5% hydrochloric acid (328.1 g) and 5% aqueous sodium bicarbonate (378.1 g). The toluene solution thus obtained was dried over suitable amount of magnesium sulfate and then concentrated to about a half of the volume under reduced pressure. To the concentrate was added dropwise n-hexane (329.5 g) at room temperature over 1 hr. After keeping at 0° C. overnight, precipitates were filtered and dried under reduced pressure to give N-Boc-L-tyrosine methyl ester 3 (126.9 g, yield 99.5%) as white crystals.

Tosylation of an Aromatic Hydroxyl Group (Synthesis of Compound 4)

N-Boc-L-tyrosine methyl ester 3 (103 g, 0.35 mol) and tosyl chloride (66.7 g, 0.35 mol) were dissolved in toluene (517 g) and then cooled to 0° C. To the mixture was added dropwise triethylamine (35.5 g, 0.35 mol) at 0° C. over 90 min. The mixture was further kept at 0° C. for 4 hrs. The reaction mass was washed with 5% hydrochloric acid (255 g) and 5% aqueous sodium bicarbonate (294 g) and then concentrated at 35° C. under reduced pressure until the weight of the toluene layer reached to 243 g. After cooling to −10° C., to the concentrate was added dropwise n-hexane (310 g) over 3 hrs. Deposited crystals was filtered and dried to give N-Boc-O-tosyl L-tyrosine methyl ester 4 (147 g, yield 92%) as white crystals.

Melting point: 78.8 to 79.5° C.

$^1$H-NMR δ (CDCl$_3$)

1.41 (9H, s), 2.45 (3H, s), 2.95-3.13 (2H, m), 3.69 (3H, s), 4.51-4.58 (1H, m), 4.99 (1H, d), 6.90 (2H, d), 7.05 (2H, d), 7.31 (2H, d), 7.68 (2H, d)

Example 14

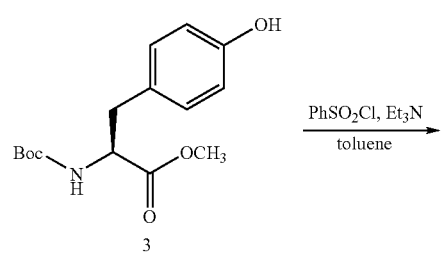

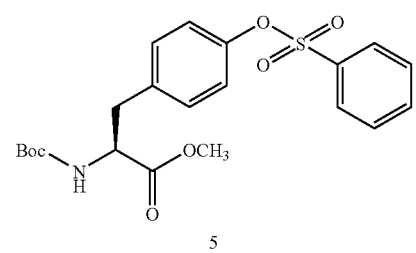

Benzenesulfonic Acid Esterification of an Aromatic Hydroxyl Group (Synthesis of Compound 5)

N-Boc-L-tyrosine methyl ester 3 (3.0 g, 0.01 mol) and benzenesulfonyl chloride (1.8 g, 0.01 mol) were dissolved in toluene (14.8 g) and then cooled to 0° C. To the mixture was added dropwise triethylamine (1.0 g, 0.01 mol) at 0° C. over 35 min. The mixture was further kept at 0° C. for 3 hrs. The reaction mass was washed with 5% hydrochloric acid (7.3 g) and 5% aqueous sodium bicarbonate (8.4 g) and then concentrated under reduced pressure with a rotary evaporator to give N-Boc-O-benzenesulfonyl-L-tyrosine methyl ester 5 (4.35 g, yield 100%) as white solid.

$^1$H-NMR δ (CDCl$_3$)

1.41 (9H, s), 2.95-3.12 (2H, m), 3.68 (3H, s), 4.51-4.58 (1H, m), 4.95-4.97 (1H, d), 6.90 (2H, d), 7.05 (2H, d), 7.50-7.55 (2H, m), 7.64-7.67 (1H, m), 7.80-7.83 (2H, m)

Example 15

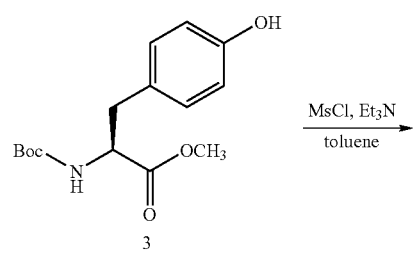

-continued

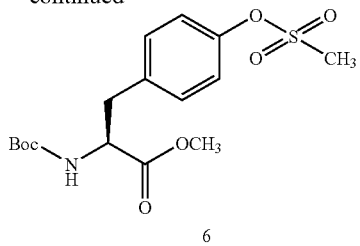

6

Mesylation of an Aromatic Hydroxyl Group (Synthesis of Compound 6)

N-Boc-L-tyrosine methyl ester 3 (29.5 g, 0.1 mol) and triethylamine (20.2 g, 0.2 mol) were dissolved in toluene (147.7 g) and then cooled to 0° C. To the mixture was added dropwise methanesulfonyl chloride (13.8 g, 0.12 mol) at 0° C. over 40 min. The mixture was further kept at 0° C. for 25 min. The reaction mass was washed with 5% hydrochloric acid (72.9 g) and 5% aqueous sodium bicarbonate (84.0 g), dried over magnesium sulfate, and then concentrated under reduced pressure with a rotary evaporator. After crystallization from the concentrate mass with n-hexane, precipitated crystals were collected by filtration and dried to give N-Boc-O-methanesulfonyl-L-tyrosine methyl ester 6 (36.0 g, yield 96%) as white crystals.

$^1$H-NMR δ (CDCl$_3$)

1.41 (9H, s), 2.99-3.19 (5H, m), 3.72 (3H, s), 3.69 (3H, s), 4.55-4.62 (1H, m), 5.01 (1H, d), 7.17-7.24 (4H, m)

Example 16

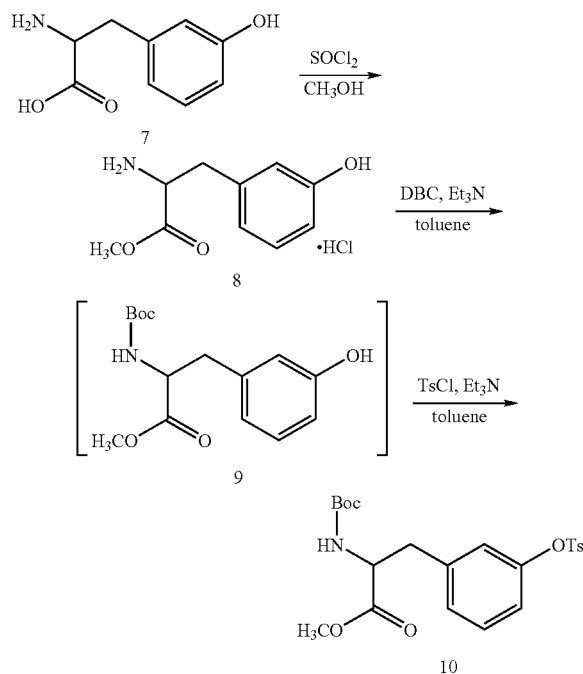

Protection of a Carboxylic Acid Moiety (Synthesis of Compound 8)

m-Tyrosine 7 (5.0 g, 27.6 mmol) was suspended in methanol (50 ml), and thionyl chloride (2.4 ml, 33.1 mmol) was added dropwise thereto at 50° C. over 0.5 hrs. The mixture was further kept at 50° C. for 3 hrs. The solvent was distilled off under reduced pressure, and toluene and ethyl acetate were added to the residue. A resulting solid was collected by filtration and dried under vacuum to give m-tyrosine methyl ester hydrochloride 8 (6.4 g, yield 100%).

Protection of an Amino Group (Synthesis of Compound 9)

m-Tyrosine methyl ester hydrochloride 8 (6.4 g, 27.6 mmol) and di-t-butylcarbonate (DBC, 6.3 g, 29.0 mmol) were suspended in toluene (40 ml), and triethylamine (4.2 ml, 30.4 mmol) was added dropwise thereto at 23° C. or below over 0.5 hrs. The mixture was further kept at 20° C. for 0.5 hrs to give a solution of N-Boc-m-tyrosine methyl ester 9 in toluene.

Tosylation of an Aromatic Hydroxyl Group (Synthesis of Compound 10)

Subsequently, a solution (15 ml) of tosyl chloride (TsCl, 5.3 g, 27.6 mmol) in toluene was added dropwise to the above solution at 20° C. over 0.5 hrs. After cooling to 0° C., to the mixture was added dropwise triethylamine (3.9 ml, 27.6 mmol) over 0.5 hrs. After keeping at 0° C. to room temperature for 3 hrs, the reaction mixture was washed with 5% hydrochloric acid (80 ml), 5% aqueous sodium bicarbonate (80 ml), water (80 ml) and saturated brine (80 ml), and dried over anhydrous magnesium sulfate. The solvent was distilled off under reduced pressure. The residue was purified by silica gel column chromatography (hexane/ethyl acetate=4/1 to 7/2) to give N-Boc-O-tosyl m-tyrosine methyl ester 10 (10.4 g, yield 83.8% from compound 8) as white crystals.

$^1$H-NMR δ (CDCl$_3$)

1.43 (9H, s), 2.45 (3H, s), 3.03 (2H, m), 3.71 (3H, s), 4.51 (1H, dd), 4.95 (1H, dd), 6.78 to 7.21 (4H, m), 7.30 to 7.70 (4H, m)

Example 17

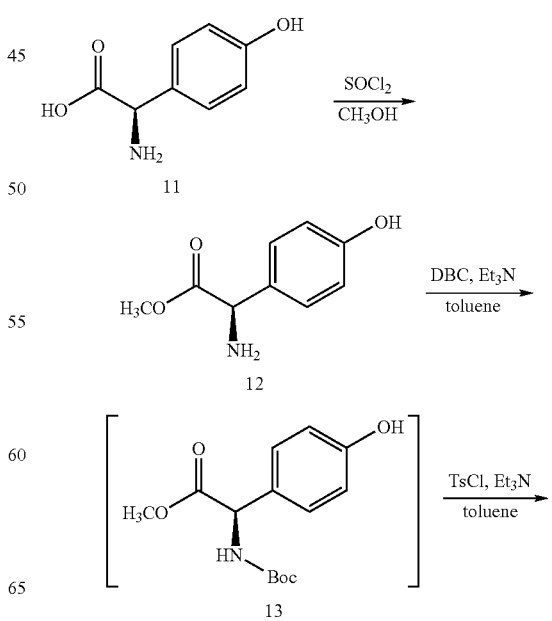

-continued

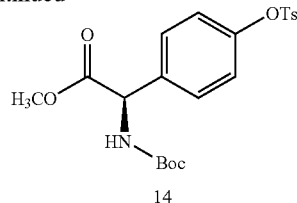

14

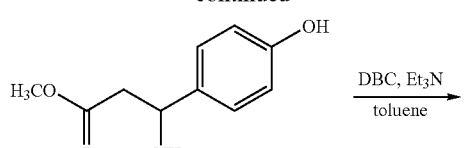

16

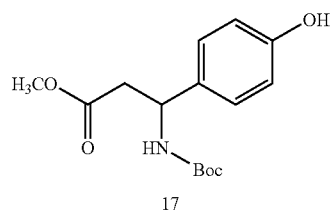

17

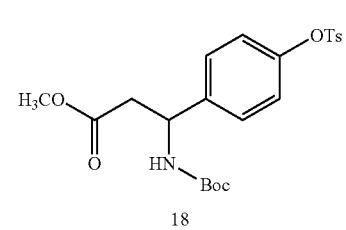

18

Protection of a Carboxylic Acid Moiety (Synthesis of Compound 12)

D-4-Hydroxyphenylglycine 11 (10.1 g, 60.4 mmol) was suspended in methanol (100 ml), and thionyl chloride (5.2 ml, 72.5 mmol) was added dropwise thereto at 50° C. over 0.5 hrs. After further keeping at 50° C. for 3 hrs, the solvent was distilled off under reduced pressure, and toluene and ethyl acetate were added to the residue. A resulting solid was collected by filtration and dried in vacuo to give D-4-hydroxyphenylglycine methyl ester hydrochloride 12 (12.5 g, yield 95.3%).

Protection of Amino Group (Synthesis of Compound 13)

D-4-Hydroxyphenylglycine methyl ester hydrochloride 12 (12.0 g, 54.0 mmol) and di-t-butylcarbonate (DBC, 12.4 g, 56.7 mmol) were suspended in toluene (75 ml), and triethylamine (8.2 ml, 59.0 mmol) was added dropwise thereto at 23° C. or below over 0.5 hrs. The mixture was further kept at 20° C. for 0.5 hrs to give a solution of N-Boc-D-4-hydroxyphenylglycine methyl ester 13 in toluene.

Tosylation of an Aromatic Hydroxyl Group (Synthesis of Compound 14)

Subsequently, a solution (30 ml) of tosyl chloride (TsCl, 10.3 g, 54.0 mmol) in toluene was added dropwise to the above solution at 20° C. over 0.5 hrs, and then cooled to 0° C. To the mixture was added dropwise triethylamine (7.5 ml, 54.0 mmol) over 0.5 hrs. After keeping at 0° C. to room temperature for 3 hrs, the reaction mixture was washed with 5% hydrochloric acid (160 ml), 5% aqueous sodium bicarbonate (160 ml), water (160 ml) and saturated brine (160 ml), and dried over anhydrous magnesium sulfate. The solvent was distilled off under reduced pressure. The residue was purified by silica gel column chromatography (hexane/ethyl acetate=4/1) to give N-Boc-D-4-tosylphenylglycine methyl ester 14 (17.7 g, yield 75.3% from compound 12) as white crystals.

$^1$H-NMR δ (CDCl$_3$)

1.42 (9H, s), 2.45 (3H, s), 3.72 (3H, s), 5.29 (1H, d), 5.55 (1H, d), 6.95 to 7.72 (8H, m)

Example 18

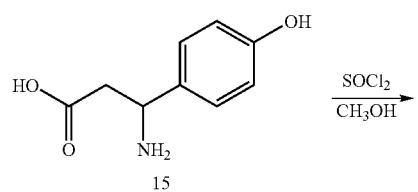

15

Protection of a Carboxylic Acid Moiety (Synthesis of Compound 16)

3-Amino-3-(4-hydroxyphenyl)propionic acid (150.91 g, 5 mmol) was suspended in methanol (2 ml), and thionyl chloride (0.43 ml, 6 mmol) was added dropwise thereto at 40° C. over 37 min. After further keeping at 40° C. for 2 hrs, the solvent was distilled off under reduced pressure to give oil (1.32 g). The oil was directly used in the next step without purification.

Protection of an Amino Group (Synthesis of Compound 17)

The oily substance obtained in the above step and di-t-butylcarbonate (DBC, 1.15 g, 5 mmol) were suspended in toluene (6.7 ml), and triethylamine (4.6 ml, 6 mmol) was added dropwise thereto at 20° C. or below over 10 min. The mixture was further kept at 16° C. overnight to give a solution of N-(t-butyloxycarbonyl)-3-amino-3-(4-hydroxyphenyl)propionic acid methyl ester hydrochloride 17 in toluene.

Tosylation of an Aromatic Hydroxyl Group (Synthesis of Compound 18)

Subsequently, a solution (2.7 ml) of tosyl chloride (TsCl, 0.95 g, 5 mmol) in toluene was added to the above solution at 13° C. and cooled to −10° C. To the mixture was added dropwise triethylamine (0.7 ml, 5 mmol) over 10 min. After keeping at −10° C. to 0° C. for 3 hrs, to the reaction mixture was added 5% hydrochloric acid (20 ml), and the mixture was extracted with ethyl acetate (15 ml×3), washed with water (20 ml) and saturated brine (20 ml), and dried over anhydrous magnesium sulfate. The solvent was distilled off under reduced pressure. The residue was purified by silica gel column chromatography (hexane/ethyl acetate=2/1) to give N-(t-butyloxycarbonyl)-3-amino-3-(4-(p-toluenesulfonyloxy)phenyl)propionic acid methyl ester 18 (1.63 g, yield 72.7% from compound 15) as white crystals.

$^1$H-NMR δ (CDCl$_3$)
1.42 (9H, s), 2.45 (3H, s), 2.74 (2H, brs) 3.63 (3H, s), 5.01 (1H, brs), 5.48 (1H, brs), 6.85 to 7.76 (8H, m)

INDUSTRIAL APPLICABILITY

According to the process of the present invention, an optically active biaryl compound, which is useful as intermediates for medicaments, agrochemicals, etc., can be produced at low cost and in high yield.

The invention claimed is:

1. An optically active compound of the formula (1a):

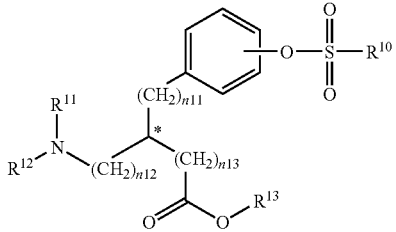

wherein
R$^{10}$ is a substituted or unsubstituted alkyl or aryl group,
R$^{11}$ is a protecting group for an amino group,
R$^{12}$ is a protecting group for an amino group, or a hydrogen atom,
R$^{13}$ is a substituted or unsubstituted alkyl group, or either R$^{11}$ or R$^{12}$ and R$^{13}$ are taken together to form a protecting group for amino acid,
n$_{11}$, n$_{12}$ and n$_{13}$ are each independently an integer of 0 or 1,
the carbon atom marked with * is an asymmetric carbon atom,
provided that R$^{10}$ is not a trifluoromethyl group, a nonafluorobutyl group or a pentafluorophenyl group.

2. A composition comprising the optically active compound of the formula (1a) according to claim 1 and an enantiomer thereof in any ratio.

3. The compound according to claim 1, wherein R$^{11}$ is a carbamate-type amino-protecting group, an amide-type amino-protecting group or an N-alkyl type amino-protecting group, and R$^{12}$ is a hydrogen atom.

4. The compound according to claim 1, wherein R$^{11}$ is an acetyl group, a trifluoroacetyl group, a benzyl group, a t-butyloxycarbonyl group, a 9-fluorenylmethoxycarbonyl group or a benzyloxycarbonyl group, and R$^{12}$ is a hydrogen atom.

5. The compound according to any one of claims 1 to 4, wherein R$^{13}$ is an alkyl group having 1 to 4 carbons or a benzyl group.

6. The compound according to any one of claims 1 to 5, wherein R$^{10}$ is a methyl group, a phenyl group, a p-nitrophenyl group or a p-methylphenyl group.

* * * * *